US009422322B2

(12) United States Patent
Dyatkina et al.

(10) Patent No.: US 9,422,322 B2
(45) Date of Patent: Aug. 23, 2016

(54) SUBSTITUTED NUCLEOSIDES, NUCLEOTIDES AND ANALOGS THEREOF

(71) Applicant: Alios BioPharma, Inc., South San Francisco, CA (US)

(72) Inventors: Natalia Dyatkina, Mountain View, CA (US); Guangyi Wang, Carlsbad, CA (US); Leonid Beigelman, San Mateo, CA (US); Vivek Kumar Rajwanshi, Cupertino, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

(21) Appl. No.: 14/312,990

(22) Filed: Jun. 24, 2014

(65) Prior Publication Data

US 2015/0005251 A1    Jan. 1, 2015

Related U.S. Application Data

(60) Provisional application No. 61/839,756, filed on Jun. 26, 2013.

(51) Int. Cl.
| | | |
|---|---|---|
| *A01N 43/04* | (2006.01) | |
| *A61K 31/70* | (2006.01) | |
| *C07H 19/20* | (2006.01) | |
| *C07H 19/06* | (2006.01) | |
| *C07H 19/16* | (2006.01) | |
| *C07H 19/10* | (2006.01) | |
| *A61K 31/7072* | (2006.01) | |
| *A61K 31/7068* | (2006.01) | |
| *A61K 31/708* | (2006.01) | |
| *A61K 45/06* | (2006.01) | |

(52) U.S. Cl.
CPC ............ *C07H 19/20* (2013.01); *A61K 31/708* (2013.01); *A61K 31/7068* (2013.01); *A61K 31/7072* (2013.01); *A61K 45/06* (2013.01); *C07H 19/06* (2013.01); *C07H 19/10* (2013.01); *C07H 19/16* (2013.01)

(58) Field of Classification Search
None
See application file for complete search history.

(56) References Cited

U.S. PATENT DOCUMENTS

| | | | |
|---|---|---|---|
| 5,432,272 | A | 7/1995 | Benner et al. |
| 7,125,855 | B2 | 10/2006 | Bhat et al. |
| 2012/0070411 | A1 | 3/2012 | Beigelman et al. |
| 2012/0070415 | A1 | 3/2012 | Beigelman et al. |
| 2012/0071434 | A1 | 3/2012 | Smith et al. |
| 2012/0165286 | A1 | 6/2012 | Beigelman et al. |
| 2013/0164261 | A1 | 6/2013 | Wang et al. |
| 2013/0165400 | A1 | 6/2013 | Beigelman et al. |
| 2013/0252920 | A1 | 9/2013 | Blatt et al. |
| 2013/0253181 | A1 | 9/2013 | Serebryany et al. |
| 2013/0281687 | A1 | 10/2013 | Serebryany et al. |
| 2014/0179627 | A1 | 6/2014 | Beigelman et al. |
| 2014/0179910 | A1 | 6/2014 | Beigelman et al. |
| 2014/0303108 | A1 | 10/2014 | Beigelman et al. |
| 2014/0303113 | A1 | 10/2014 | Krop et al. |
| 2015/0011497 | A1 | 1/2015 | Beigelman et al. |
| 2015/0038451 | A1 | 2/2015 | Smith et al. |
| 2015/0051167 | A1 | 2/2015 | Wang et al. |
| 2015/0105341 | A1 | 4/2015 | Beigelman et al. |
| 2015/0183819 | A1 | 7/2015 | Beigelman et al. |

FOREIGN PATENT DOCUMENTS

| | | |
|---|---|---|
| WO | WO 96/40705 | 12/1996 |
| WO | WO 2008/082601 | 7/2008 |
| WO | WO 2010/108140 | 9/2010 |
| WO | WO 2012/040124 | 3/2012 |
| WO | WO 2013/142124 | 9/2013 |
| WO | WO 2013/142159 | 9/2013 |
| WO | WO 2013/142525 | 9/2013 |
| WO | WO/2014/100498 | 6/2014 |
| WO | WO 2014/134251 | 9/2014 |
| WO | WO 2014/164533 | 10/2014 |
| WO | WO 2014/209983 | 12/2014 |

OTHER PUBLICATIONS

Bondada, L. et al., "Adenosine Dioxolane Nucleoside Phosphoramidates as Antiviral Agents for Human Immunodeficiency and Hepatitis B Viruses" ACS Medicinal Chemistry Letters,(2013) 4(8):747-751.
Gore et al., "Influence of 2'-fluoro versus 2'-O-methyl substituent on the sugar puckering of 4'-C-aminomethyl uridine" JOC (2013) 78:9956-9962.
Greene, et al., Protective Groups in Organic Synthesis, 3. Ed., John Wiley & Sons, (1999) Cover & Contents pages.
"IUPAC-IUB Commission on Biochemical Nomenclature Abbreviated Nomenclature of Synthetic Polypeptides (Polymerized Amino Acids)* Revised Recommendations (1971)" *Biochemistry*. (1972) 11(5) :942-944.
McOmie, J. F. W., Protective Groups in Organic Chemistry, Plenum Press, 1973. Cover & Contents pages only.
McGuigan et al., "Phosphate Prodrugs Derived from N-Acetylglucosamine Have Enhanced Chondroprotective Activity in Explant Cultures and Represent a New Lead in Antiosteoarthritis Drug Discovery" J. Med. Chem. (2008) 51(18):5807-5812.
Pfundheller et al., Oligonucleotides Containing Novel 4'C-or 3'-C-(Aminoalkyl)-Branched Thymidines) Helv. Chemica. Acta. (2000) 83:128-151.
Villard et al., "Phenyl phosphotriester derivatives of AZT: Variations upon the SATE moiety" Bioorg. Med. Chem. (2008) 16(15):7321-7329.
International Search Report and Written Opinion dated Oct. 28, 2014 for PCT Application No. PCT/US2014/043841, filed Jun. 24, 2014.
International Preliminary Report on Patentability mailed Jun. 2, 2015 for PCT Application No. PCT/US2014/043841, filed Jun. 24, 2014.

*Primary Examiner* — Patrick Lewis
(74) *Attorney, Agent, or Firm* — Knobbe, Martens, Olson & Bear, LLP

(57) ABSTRACT

Disclosed herein are nucleosides, nucleotides and analogs thereof, pharmaceutical compositions that include one or more of nucleosides, nucleotides and analogs thereof, and methods of synthesizing the same. Also disclosed herein are methods of ameliorating and/or treating a paramyxovirus viral infection, with a nucleoside, a nucleotide and an analog thereof.

42 Claims, 3 Drawing Sheets

| Compound | Structure |
|---|---|
| MDT-637 | 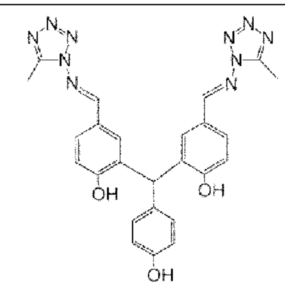 |
| BTA9881 | 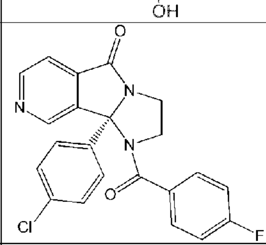 |
| TMC-353121 | 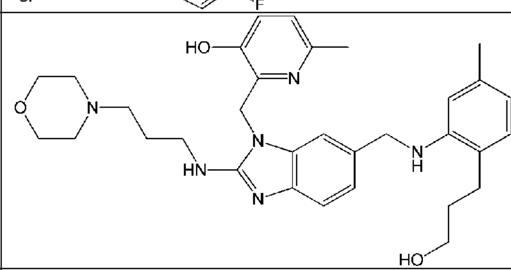 |
| MBX-300 | 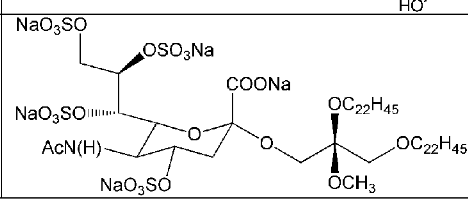 |

| Compound | Structure |
|---|---|
| YM-53403 | 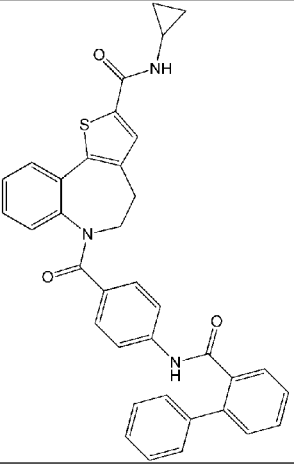 |
| Ribavirin | 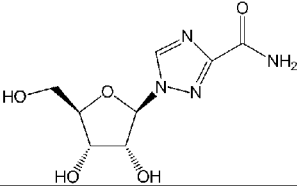 |

SUBSTITUTED NUCLEOSIDES, NUCLEOTIDES AND ANALOGS THEREOF

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

REFERENCE TO SEQUENCE LISTING

The present application is filed with a Sequence Listing in Electronic format. The Sequence Listing is provided as a file entitled ALIOS076.txt, created Jun. 23, 2014, which is approximately 4 kb in size. The information in the electronic format of the sequence listing is incorporated herein by reference in its entirety.

BACKGROUND

1. Field

The present application relates to the fields of chemistry, biochemistry and medicine. More particularly, disclosed herein are nucleoside, nucleotides and analogs thereof, pharmaceutical compositions that include one or more nucleosides, nucleotides and analogs thereof, and methods of synthesizing the same. Also disclosed herein are methods of ameliorating and/or treating a paramyxovirus viral infection with one or more nucleosides, nucleotides and analogs thereof.

2. Description

Respiratory viral infections, including upper and lower respiratory tract viral infections, infects and is the leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs.

Nucleoside analogs are a class of compounds that have been shown to exert antiviral activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I), or a pharmaceutically acceptable salt thereof.

Some embodiments disclosed herein relate to methods of ameliorating and/or treating a paramyxovirus viral infection that can include administering to a subject suffering from the paramyxovirus viral infection an effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a paramyxovirus viral infection. Still other embodiments described herein relate to compounds of Formula (I), or a pharmaceutically acceptable salt thereof, that can be used for ameliorating and/or treating a paramyxovirus viral infection. Yet still other embodiments disclosed herein relate to methods of ameliorating and/or treating a paramyxovirus viral infection that can include contacting a cell infected with the paramyxovirus with an effective amount of one or more compounds of Formula (I), or a pharmaceutically acceptable salt thereof, or a pharmaceutical composition that includes one or more compounds of Formula (I), or a pharmaceutically acceptable salt thereof. Some embodiments disclosed herein relate to methods of inhibiting the replication of a paramyxovirus that can include contacting a cell infection with the paramyxovirus with an effective amount of one or more compounds of Formula (I), or a pharmaceutically acceptable salt thereof, or a pharmaceutical composition that includes one or more compounds of Formula (I), or a pharmaceutically acceptable salt thereof.

Some embodiments disclosed herein relate to methods of ameliorating and/or treating a paramyxovirus viral infection that can include administering to a subject suffering from the viral infection an effective amount of a compound described herein or a pharmaceutically acceptable salt thereof (for example, one or more compounds of Formula (I), or a pharmaceutically acceptable salt thereof), or a pharmaceutical composition that includes one or more compounds described herein, in combination with one or more agents described herein. Some embodiments disclosed herein relate to methods of ameliorating and/or treating a paramyxovirus viral infection that can include contacting a cell infected with the virus with an effective amount of a compound described herein or a pharmaceutically acceptable salt thereof (for example, one or more compounds of Formula (I), or a pharmaceutically acceptable salt thereof), or a pharmaceutical composition that includes one or more compounds described herein, in combination with one or more agents described herein.

DETAILED DESCRIPTION

Figure 1:
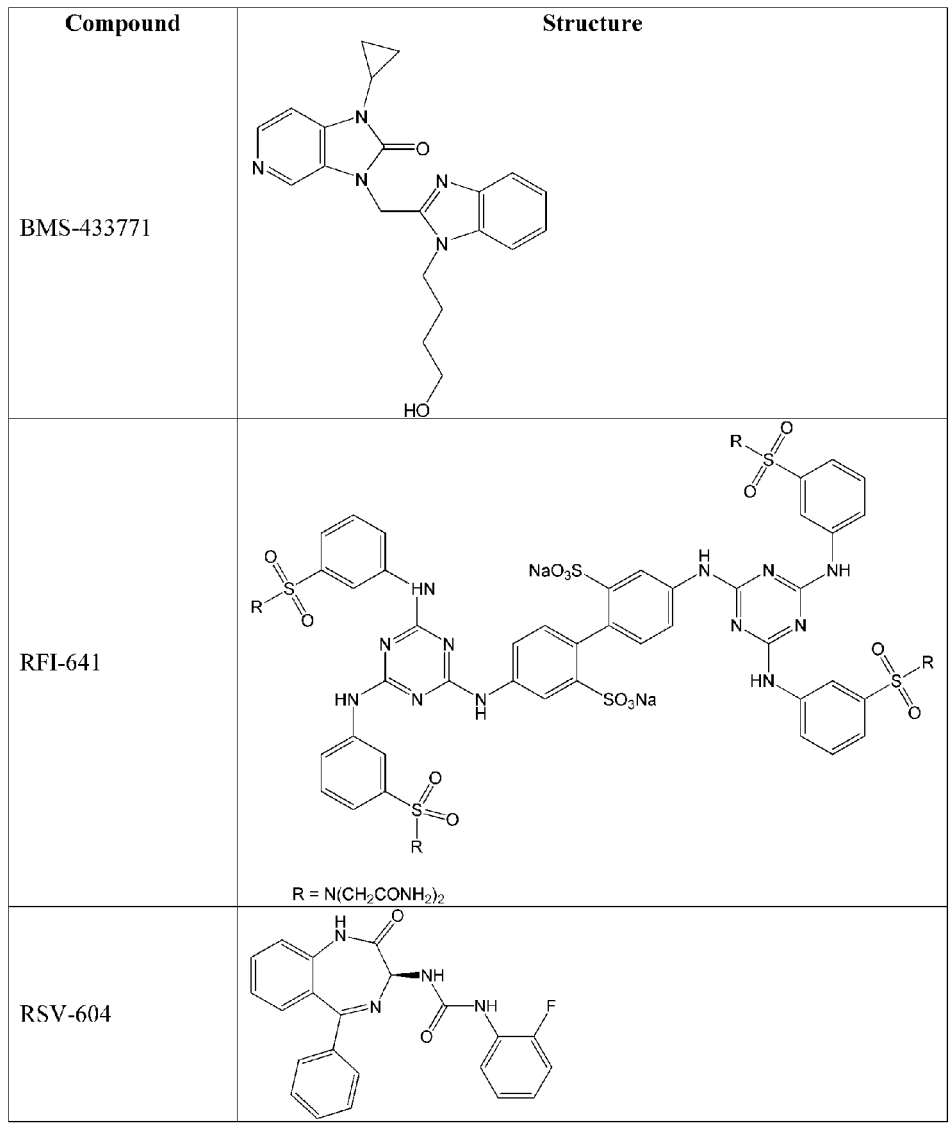
FIG. 1 shows example anti-RSV agents.

Paramyxoviridae family is a family of single stranded RNA viruses. Several genera of the paramyxoviridae family include respirovirus, rubulavirus, pneumovirus and metapneumovirus. These viruses can be transmitted person to person via direct or close contact with contaminated respiratory droplets or fomites.

Human Respiratory Syncytial Virus (RSV) is a species of pneumovirus and a negative single-stranded RNA virus. RSV can cause respiratory infections, and can be associated with bronchiolitis and pneumonia. Symptoms of an RSV infection include coughing, sneezing, runny nose, fever, decrease in appetite, sore throat, headache and wheezing. RSV is the most common cause of bronchiolitis and pneumonia in children under one year of age in the world, and can be the cause of tracheobronchitis in older children and adults. In the United States, between 75,000 and 125,000 infants are hospitalized each year with RSV. Among adults older than 65 years of age, an estimated 14,000 deaths and 177,000 hospitalizations have been attributed to RSV.

Treatment options for people infected with RSV are currently limited. Antibiotics, usually prescribed to treat bacterial infections, and over-the-counter medication are not effective in treating RSV and may help only to relieve some of the symptoms. In severe cases, a nebulized bronchodilator, such as albuterol, may be prescribed to relieve some of the symptoms, such as wheezing. RespiGam® (RSV-IGIV, MedImmune, approved for high risk children younger than 24 months of age) and Synagis® (palivizumab, MedImmune, approved for high risk children younger than 24 months of age) have been approved for prophylactic use against RSV, and Virzole® (ribavirin by aerosol, ICN pharmaceuticals) have been approved for the treatment of RSV.

Parainfluenza viruses are typically negative-sense RNA viruses. Species of respirovirus include human parainfluenza viruses 1 and 3; and species of rubulavirus include human parainfluenza viruses 2 and 4. Human parainfluenza virus includes four serotypes types (HPIV-1, HPIV-2, HPIV-3 and HPIV-4), and human parainfluenza virus 4 (HPIV-4) include two antigenic subgroups, A and B. Human parainfluenza viruses can cause upper and lower respiratory tract infections. Human parainfluenza virus 1 (HPIV-1) and human parainfluenza virus 2 (HPIV-2) can be associated with croup; human parainfluenza virus 3 (HPIV-3) can be associated with bronchiolitis and pneumonia. According to the Centers of Disease Control and Prevention (CDC), there are no vaccines against human parainfluenza viruses.

A species of metapneumovirus is human metapneumovirus. Human metapneumovirus is a negative single-stranded RNA virus. Human metapneumovirus can cause respiratory tract infections, such as upper and lower respiratory tract infections in human, for example young children.

Respiratory infections include colds, croup, pneumonia, bronchitis and bronchiolitis. Symptoms can include a cough, runny nose, nasal congestion, sore throat, fever, difficulty breathing, abnormally rapid breathing, wheezing vomiting, diarrhea and ear infections.

DEFINITIONS

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as without limitation, $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, $R^{22A}$, $R^{23A}$, $R^{24A}$, $R^{25A}$, $R^{26A}$, $R^{27A}$, $R^{28A}$, $R^{29A}$, $R^{30A}$, $R^{31A}$, $R^{32A}$, $R^{33A}$, $R^{34A}$, $R^{35A}$, $R^{36A}$, $R^{37A}$ and $R^{38A}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

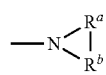

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, azido, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl or a heteroalicyclyl may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenyl(alkyl), 3-phenyl(alkyl) and naphthyl(alkyl).

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a heteroalicyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl), and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy(isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O) OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)—, and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The terms "phosphorothioate" and "phosphothioate" refer to a compound of the general formula

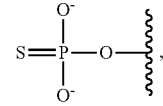

its protonated forms (for example,

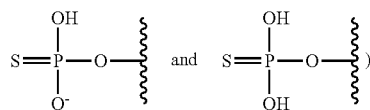

and its tautomers (such as

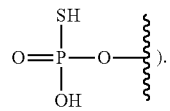

As used herein, the term "phosphate" is used in its ordinary sense as understood by those skilled in the art, and includes its protonated forms (for example,

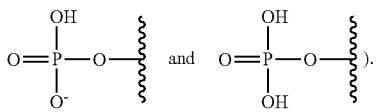

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

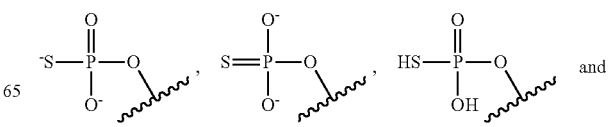

-continued

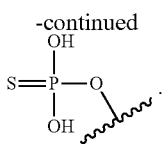

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt of the foregoing:

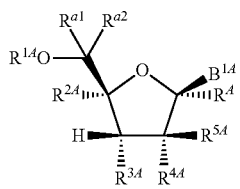
(I)

wherein: $B^{1A}$ can be an optionally substituted heterocyclic base or an optionally substituted heterocyclic base with a protected amino group; $R^A$ can be hydrogen or deuterium; $R^{1A}$ can be selected from hydrogen, an optionally substituted acyl, an optionally substituted O-linked amino acid,

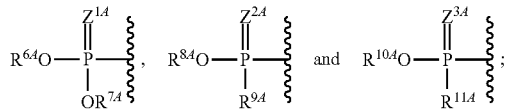

$R^{a1}$ and $R^{a2}$ can be independently hydrogen or deuterium; $R^{2A}$ can be a $C_{1-6}$ azidoalkyl or a $C_{1-6}$ aminoalkyl; $R^{3A}$ can be selected from OH, —OC(=O)$R^{nA}$ and an optionally substituted O-linked amino acid; $R^{4A}$ can be halogen; $R^{5A}$ can be hydrogen or halogen; $R^{6A}$, $R^{7A}$ and $R^{8A}$ can be independently selected from absent, hydrogen, an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—(CR$^{15A}$R$^{16A}$)$_p$—O—C$_{1-24}$ alkyl, an optionally substituted *—(CR$^{17A}$R$^{18A}$)$_q$—O—C$_{1-24}$ alkenyl,

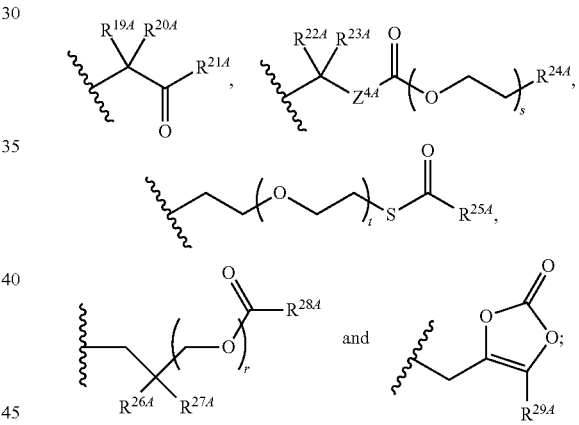

or $R^{6A}$ can be

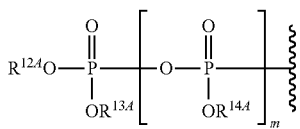

and $R^{7A}$ can be absent or hydrogen; or $R^{6A}$ and $R^{7A}$ can be taken together to form a moiety selected from an optionally substituted

and an optionally substituted

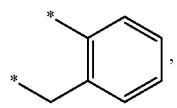

wherein the oxygens connected to $R^{6A}$ and $R^{7A}$, the phosphorus and the moiety form a six-membered to ten-membered ring system; $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, NR an optionally substituted N-linked amino acid and an optionally substituted N-linked amino acid ester derivative; $R^{10A}$ and $R^{11A}$ can be independently an optionally substituted N-linked amino acid or an optionally substituted N-linked amino acid ester derivative; $R^{12A}$, $R^{13A}$ and $R^{14A}$ can be independently absent or hydrogen; each $R^{15A}$, each $R^{16A}$, each $R^{17A}$ and each $R^{18A}$ can be independently hydrogen, an optionally substituted $C_{1-24}$ alkyl or alkoxy; $R^{19A}$, $R^{20A}$, $R^{22A}$ and $R^{23A}$ can be independently selected from hydrogen, an optionally substituted $C_{1-24}$ alkyl and an optionally substituted aryl; $R^{21A}$ and $R^{24A}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

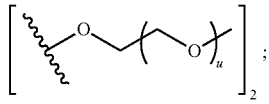

$R^{25A}$ and $R^{29A}$ can be independently selected from hydrogen, an optionally substituted $C_{1-24}$ alkyl and an optionally substituted aryl; $R^{26A}$ and $R^{27A}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28A}$ can be selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{30A}$ and $R^{31A}$ can be independently selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R'''^A$ can be an optionally substituted $C_{1-24}$-alkyl; m and t can be independently 0 or 1; p and q can be independently selected from 1, 2 and 3; r can be 1 or 2; s can be 0, 1, 2 or 3; u can be 1 or 2; and $Z^{1A}$, $Z^{2A}$, $Z^{3A}$ and $Z^{4A}$ can be independently O or S.

In some embodiments, $R^{1A}$ can be

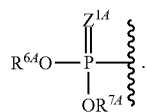

In some embodiments, $R^{6A}$ and $R^{7A}$ can be both hydrogen. In other embodiments, $R^{6A}$ and $R^{7A}$ can be both absent. In still other embodiments, at least one $R^{6A}$ and $R^{7A}$ can be absent. In yet still other embodiments, at least one $R^{6A}$ and $R^{7A}$ can be hydrogen. Those skilled in the art understand that when $R^{6A}$ and/or $R^{7A}$ are absent, the associated oxygen(s) will have a negative charge. For example, when $R^{6A}$ is absent, the oxygen associated with $R^{6A}$ will have a negative charge. In some embodiments, $Z^{1A}$ can be O (oxygen). In other embodiments, $Z^{1A}$ can be S (sulfur). In some embodiments, $R^{1A}$ can be a monophosphate. In other embodiments, $R^{1A}$ can be a monothiophosphate.

In some embodiments, when $R^{1A}$ is

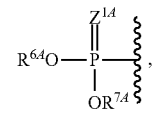

one of $R^{6A}$ and $R^{7A}$ can be hydrogen, and the other of $R^{6A}$ and $R^{7A}$ can be selected from an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, one of $R^{6A}$ and $R^{7A}$ can be hydrogen, and the other of $R^{6A}$ and $R^{7A}$ can be an optionally substituted $C_{1-24}$ alkyl. In other embodiments, both $R^{6A}$ and $R^{7A}$ can be independently selected from an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, both $R^{6A}$ and $R^{7A}$ can be an optionally substituted $C_{1-24}$ alkyl. In other embodiments, both $R^{6A}$ and $R^{7A}$ can be an optionally substituted $C_{3-24}$ alkenyl. In some embodiments, $R^{6A}$ and $R^{7A}$ can be independently an optionally substituted version of the following: myristoleyl, myristyl, palmitoleyl, palmityl, sapienyl, oleyl, elaidyl, vaccenyl, linoleyl, α-linolenyl, arachidonyl, eicosapentaenyl, erucyl, docosahexaenyl, caprylyl, capryl, lauryl, stearyl, arachidyl, behenyl, lignoceryl and cerotyl.

In some embodiments, at least one of $R^{6A}$ and $R^{7A}$ can be *—$(CR^{15A}R^{16A})_p$—O—$C_{1-24}$ alkyl. In other embodiments, $R^{6A}$ and $R^{7A}$ can be both *—$(CR^{15A}R^{16A})_p$—O—$C_{1-24}$ alkyl. In some embodiments, each $R^{15A}$ and each $R^{16A}$ can be hydrogen. In other embodiments, at least one of $R^{15A}$ and $R^{16A}$ can be an optionally substituted $C_{1-24}$ alkyl. In other embodiments, at least one of $R^{15A}$ and $R^{16A}$ can be an alkoxy (for example, benzoxy). In some embodiments, p can be 1. In other embodiments, p can be 2. In still other embodiments, p can be 3.

In some embodiments, at least one of $R^{6A}$ and $R^{7A}$ can be *—$(CR^{17A}R^{18A})_q$—O—$C_{2-24}$ alkenyl. In other embodiments, $R^{6A}$ and $R^{7A}$ can be both *—$(CR^{17A}R^{18A})_q$—O—$C_{2-24}$ alkenyl. In some embodiments, each $R^{17A}$ and each $R^{18A}$ can be hydrogen. In other embodiments, at least one of $R^{17A}$ and $R^{18A}$ can be an optionally substituted $C_{1-24}$ alkyl. In some embodiments, q can be 1. In other embodiments, q can be 2. In still other embodiments, q can be 3. When at least one of $R^{6A}$ and $R^{7A}$ is *—$(CR^{15A}R^{16A})_p$—O—$C_{1-24}$ alkyl or *—$(CR^{17A}R^{18A})_q$—O—$C_{2-24}$ alkenyl, the $C_{1-24}$ alkyl can be selected from caprylyl, capryl, lauryl, myristyl, palmityl, stearyl, arachidyl, behenyl, lignoceryl, and cerotyl, and the $C_{2-24}$ alkenyl can be selected from myristoleyl, palmitoleyl, sapienyl, oleyl, elaidyl, vaccenyl, linoleyl, α-linolenyl, arachidonyl, eicosapentaenyl, erucyl and docosahexaenyl.

In some embodiments, when $R^{1A}$ is

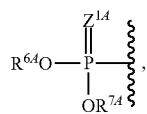

at least one of $R^{6A}$ and $R^{7A}$ can be selected from

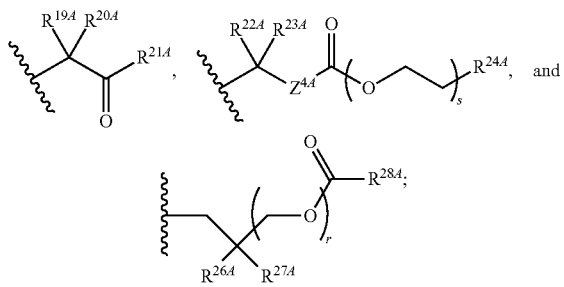

and the other of $R^{6A}$ and $R^{7A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl).

In some embodiments, at least one of $R^{6A}$ and $R^{7A}$ can be

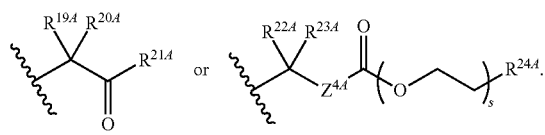

In some embodiments, both $R^{6A}$ and $R^{7A}$ can be

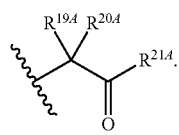

When one or both of $R^{6A}$ and $R^{7A}$ are

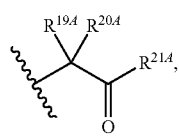

$R^{19A}$ and $R^{20A}$ can be independently selected from hydrogen, an optionally substituted $C_{1-24}$ alkyl and an optionally substituted aryl; and $R^{21A}$ can be selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

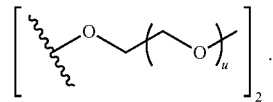

In some embodiments, $R^{19A}$ and $R^{20A}$ can be hydrogen. In other embodiments, at least one of $R^{19A}$ and $R^{20A}$ can be an optionally substituted $C_{1-24}$ alkyl or an optionally substituted aryl. In some embodiments, $R^{21A}$ can be an optionally substituted $C_{1-24}$ alkyl. In other embodiments, $R^{21A}$ can be an optionally substituted aryl. In still other embodiments, $R^{21A}$ can be an optionally substituted —O—$C_{1-24}$ alkyl or an optionally substituted —O-aryl. In some embodiments, $R^{21A}$ can be an optionally substituted —O—$C_{1-24}$ alkyl, an optionally substituted —O-aryl, an optionally substituted —O-heteroaryl or an optionally substituted —O-monocyclic heterocyclyl.

In some embodiments, both $R^{6A}$ and $R^{7A}$ can be

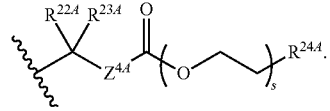

When one or both of $R^{6A}$ and $R^{7A}$ are

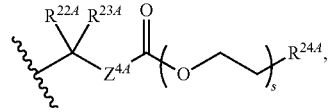

$R^{22A}$ and $R^{23A}$ can be independently selected from hydrogen, an optionally substituted $C_{1-24}$ alkyl and an optionally substituted aryl; $R^{24A}$ can be independently selected from hydrogen, an optionally substituted $C_{1-24}$ alkyl, an optionally substituted aryl, an optionally substituted —O—$C_{1-24}$ alkyl, an optionally substituted —O-aryl, an optionally substituted —O-heteroaryl, an optionally substituted —O-monocyclic heterocyclyl and

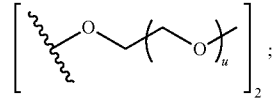

and $Z^{4A}$ can be independently O (oxygen) or S (sulfur). In some embodiments, $R^{22A}$ and $R^{23A}$ can be hydrogen. In other embodiments, at least one of $R^{22A}$ and $R^{23A}$ can be an optionally substituted $C_{1-24}$ alkyl or an optionally substituted aryl. In some embodiments, $R^{24A}$ can be an optionally substituted $C_{1-24}$ alkyl. In other embodiments, $R^{24A}$ can be an optionally substituted aryl. In still other embodiments, $R^{24A}$ can be an optionally substituted —O—$C_{1-24}$ alkyl or an optionally substituted —O-aryl. In some embodiments, $Z^{4A}$ can be O (oxygen). In other embodiments, $Z^{4A}$ can be or S (sulfur). In some embodiments, s can be 0. In other embodiments, s can be 1. In still other embodiments, s can be 2. In yet still embodiments, s can be 3. In some embodiments, s can be 0, and $R^{24A}$ can be

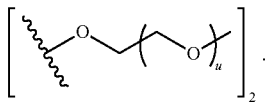

In some embodiments, u can be 1. In other embodiments, u can be 2. In some embodiments, one or both of $R^{6A}$ and $R^{7A}$ can be isopropyloxycarbonyloxymethyl (POC). In some embodiments, one or both of $R^{6A}$ and $R^{7A}$ can be pivaloyloxymethyl (POM). In some embodiments, $R^{6A}$ and $R^{7A}$ can be both a isopropyloxycarbonyloxymethyl group, and form a bis(isopropyloxycarbonyloxymethyl) (bis(POC)) prodrug. In some embodiments, $R^{6A}$ and $R^{7A}$ can be both a pivaloyloxymethyl group, and form a bis(pivaloyloxymethyl) (bis(POM)) prodrug.

In some embodiments, both $R^{6A}$ and $R^{7A}$ can be

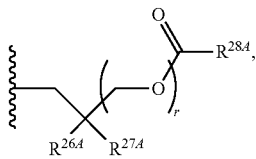

wherein $R^{26A}$ and $R^{27A}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28A}$ can be selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and r can be 1 or 2.

In some embodiments, $R^{6A}$ and $R^{7A}$ can be both an optionally substituted aryl. In some embodiments, at least one of $R^{6A}$ and $R^{7A}$ can be an optionally substituted aryl. For example, both $R^{6A}$ and $R^{7A}$ can be an optionally substituted phenyl or an optionally substituted naphthyl. When substituted, the substituted aryl can be substituted with 1, 2, 3 or more than 3 substituents. When more the two substituents are present, the substituents can be the same or different. In some embodiments, when at least one of $R^{6A}$ and $R^{7A}$ is a substituted phenyl, the substituted phenyl can be a para-, ortho- or meta-substituted phenyl.

In some embodiments, $R^{6A}$ and $R^{7A}$ can be both an optionally substituted aryl($C_{1-6}$ alkyl). In some embodiments, at least one of $R^{6A}$ and $R^{7A}$ can be an optionally substituted aryl($C_{1-6}$ alkyl). For example, both $R^{6A}$ and $R^{7A}$ can be an optionally substituted benzyl. When substituted, the substituted benzyl group can be substituted with 1, 2, 3 or more than 3 substituents. When more the two substituents are present, the substituents can be the same or different. In some embodiments, the aryl group of the aryl($C_{1-6}$ alkyl) can be a para-, ortho- or meta-substituted phenyl.

In some embodiments, $R^{6A}$ and $R^{7A}$ can be both

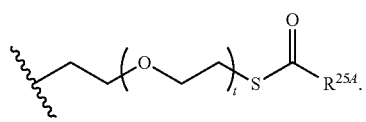

In some embodiments, at least one of $R^{6A}$ and $R^{7A}$ can be

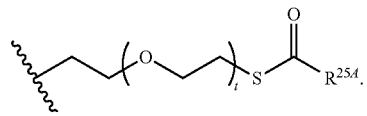

In some embodiments, $R^{25A}$ can be hydrogen. In other embodiments, $R^{25A}$ can be an optionally substituted $C_{1-24}$ alkyl. In still other embodiments, $R^{25A}$ can be an optionally substituted aryl. In some embodiments, $R^{25A}$ can be a $C_{1-6}$ alkyl, for example, methyl, ethyl, n-propyl, isopropyl, n-butyl, isobutyl, tert-butyl, pentyl (branched and straight-chained) and hexyl (branched and straight-chained). In some embodiments, t can be 0. In other embodiments, t can be 1. In some embodiments, one or both of $R^{6A}$ and $R^{7A}$ can be a S-acylthioethyl (SATE).

In some embodiments, $R^{6A}$ and $R^{7A}$ can be both

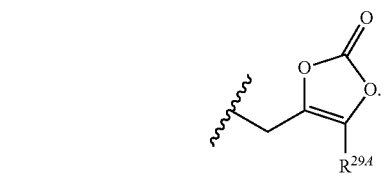

In some embodiments, at least one of $R^{6A}$ and $R^{7A}$ can be

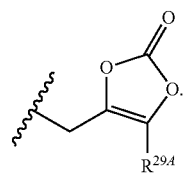

In some embodiments, $R^{29A}$ can be hydrogen. In other embodiments, $R^{29A}$ can be an optionally substituted $C_{1-24}$ alkyl. In some embodiments, $R^{29A}$ can be a $C_{1-4}$ alkyl, such as methyl, ethyl, n-propyl, iso-propyl, n-butyl, iso-butyl and t-butyl. In still other embodiments, $R^{29A}$ can be an optionally substituted aryl, such as an optionally substituted phenyl or an optionally substituted naphthyl. In some embodiments, $R^{6A}$ and $R^{7A}$ can be both a dioxolenone group and form a dioxolenone prodrug.

In some embodiments, $R^{1A}$ can be

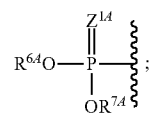

$R^{6A}$ can be

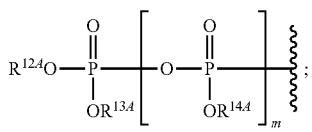

$R^{7A}$ can be absent or hydrogen; $R^{12A}$, $R^{13A}$ and $R^{14A}$ can be independently absent or hydrogen; and m can be 0 or 1. In some embodiments, m can be 0, and $R^{7A}$, $R^{12A}$ and $R^{13A}$ can be independently absent or hydrogen. In other embodiments, m can be 1, and $R^{7A}$, $R^{12A}$, $R^{13A}$ and $R^{14A}$ can be independently absent or hydrogen. Those skilled in the art understand that when m is 0, $R^{6A}$ can be diphosphate, when $Z^{1A}$ is oxygen, or an alpha-thiodiphosphate, when $Z^{1A}$ is sulfur. Likewise, those skilled in the art understand that when m is 1, $R^{6A}$ can be triphosphate, when $Z^{1A}$ is oxygen, or an alpha-thiotriphosphate, when $Z^{1A}$ is sulfur.

In some embodiments, $R^{6A}$ and $R^{7A}$ can be taken together to form an optionally substituted

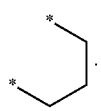

For example, $R^{1A}$ can be an optionally substituted

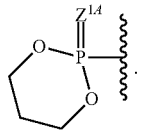

When substituted, the ring can be substituted 1, 2, 3 or more times. When substituted with multiple substituents, the substituents can be the same or different. In some embodiments, when $R^{1A}$ is

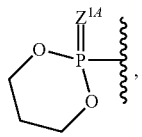

the ring can be substituted with an optionally substituted aryl group and/or an optionally substituted heteroaryl. An example of a suitable heteroaryl is pyridinyl. In some embodiments, $R^{6A}$ and $R^{7A}$ can be taken together to form an optionally substituted

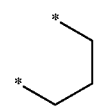

such as

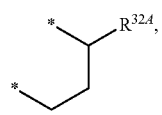

wherein $R^{32A}$ can be an optionally substituted aryl, an optionally substituted heteroaryl or an optionally substituted heterocyclyl. In some embodiments, $R^{6A}$ and $R^{7A}$ can form a cyclic 1-aryl-1,3-propanyl ester (HepDirect) prodrug moiety.

In some embodiments, $R^{6A}$ and $R^{7A}$ can be taken together to form an optionally substituted

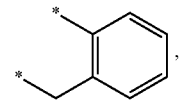

wherein the oxygens connected to $R^{6A}$ and $R^{7A}$, the phosphorus and the moiety form a six-membered to ten-membered ring system. Example of an optionally substituted

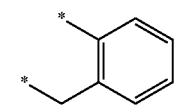

include

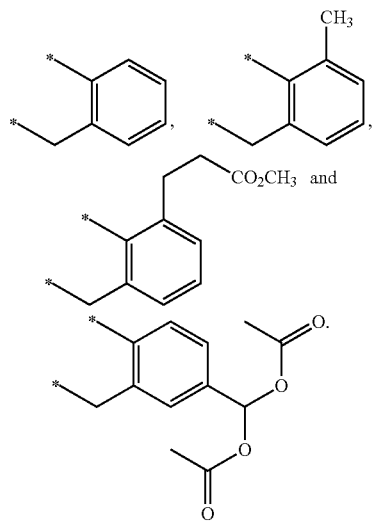

In some embodiments, $R^{6A}$ and $R^{7A}$ can form a cyclosaligenyl (cycloSal) prodrug.

In some embodiments, $R^{6A}$ and $R^{7A}$ can be the same. In some embodiments, $R^{6A}$ and $R^{7A}$ can be different.

In some embodiments, $Z^{1A}$ can be oxygen. In other embodiments, $Z^{1A}$ can be sulfur.

In some embodiments, $R^{1A}$ can be

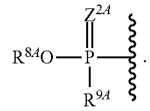

In some embodiments, $R^{8A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^{8A}$ can be hydrogen, and $R^{9A}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained) and hexyl (branched and straight-chained). In other embodiments, $R^{8A}$ can be hydrogen, and $R^{9A}$ can be $NR^{30A}R^{31A}$, wherein $R^{30}$ and $R^{31}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^{8A}$ can be absent or hydrogen; and $R^{9A}$ can be an optionally substituted N-linked amino acid or an optionally substituted N-linked amino acid ester derivative. In other embodiments, $R^{8A}$ can be an optionally substituted aryl; and $R^{9A}$ can be an optionally substituted N-linked amino acid or an optionally substituted N-linked amino acid ester derivative. In still other embodiments, $R^{8A}$ can be an optionally substituted heteroaryl; and $R^{9A}$ can be an optionally substituted N-linked amino acid or an optionally substituted N-linked amino acid ester derivative. In some embodiments, $R^{9A}$ can be selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. Examples of an optionally substituted N-linked amino acid ester derivatives include optionally substituted versions of the following: alanine isopropyl ester, alanine cyclohexyl ester, alanine neopentyl ester, valine isopropyl ester and leucine isopropyl ester. In some embodiments, $R^{9A}$ can have the structure

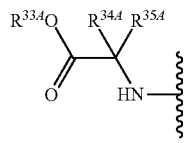

wherein $R^{33A}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{34A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{35A}$ can be hydrogen or an optionally substituted $C_{1-4}$-alkyl; or $R^{34A}$ and $R^{35A}$ can be taken together to form an optionally substituted $C_{3-6}$ cycloalkyl.

When $R^{34A}$ is substituted, $R^{34A}$ can be substituted with one or more substituents selected from N-amido, mercapto, alkylthio, an optionally substituted aryl, hydroxy, an optionally substituted heteroaryl, O-carboxy and amino. In some embodiments, $R^{34A}$ can be an unsubstituted $C_{1-6}$-alkyl, such as those described herein. In some embodiments, $R^{34A}$ can be hydrogen. In other embodiments, $R^{34A}$ can be methyl. In some embodiments, $R^{33A}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{33A}$ can be methyl or isopropyl. In some embodiments, $R^{33A}$ can be ethyl or neopentyl. In other embodiments, $R^{33A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{33A}$ can be an optionally substituted cyclohexyl. In still other embodiments, $R^{33A}$ can be an optionally substituted aryl, such as phenyl and naphthyl. In yet still other embodiments, $R^{33A}$ can be an optionally substituted aryl($C_{1-6}$ alkyl). In some embodiments, $R^{33A}$ can be an optionally substituted benzyl. In some embodiments, $R^{33A}$ can be an optionally substituted $C_{1-6}$ haloalkyl, for example, $CF_3$. In some embodiments, $R^{35A}$ can be hydrogen. In other embodiments, $R^{35A}$ can be an optionally substituted $C_{1-4}$-alkyl, such as methyl, ethyl, n-propyl, isopropyl, n-butyl, isobutyl and tert-butyl. In an embodiment, $R^{35A}$ can be methyl. In some embodiments, $R^{34A}$ and $R^{35A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{34A}$ and $R^{35A}$, the carbon to which $R^{34A}$ and $R^{35A}$ are attached may be a chiral center. In some embodiment, the carbon to which $R^{34A}$ and $R^{35A}$ are attached may be a (R)-chiral center. In other embodiments, the carbon to which $R^{34A}$ and $R^{35A}$ are attached may be a (S)-chiral center.

In some embodiments, when $R^{1A}$ is

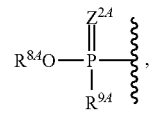

$Z^{2A}$ can be O (oxygen). In other embodiments, when $R^{1A}$ is

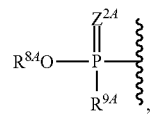

$Z^{2A}$ can be S (sulfur). In some embodiments, when $R^{1A}$ is

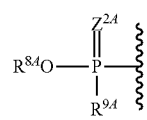

a compound of Formula (I) can be a phosphoramidate prodrug, such as an aryl phosphoramidate prodrug.

In some embodiments, $R^{1A}$ can be

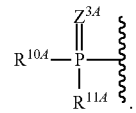

In some embodiments, $R^{10A}$ and $R^{11A}$ can be both an optionally substituted N-linked amino acid or an optionally substituted N-linked amino acid ester derivative. In some embodiments, $R^{10A}$ and $R^{11A}$ can be independently selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{10A}$ and $R^{11A}$ can be an optionally substituted version of the following: alanine isopropyl ester, alanine cyclohexyl ester, alanine neopentyl ester, valine isopropyl ester and leucine isopropyl ester. In some embodiments, $R^{10A}$ and $R^{11A}$ can independently have the structure

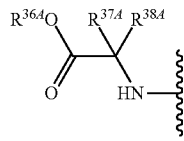

wherein $R^{36A}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{37A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{38A}$ can be hydrogen or an optionally substituted $C_{1-4}$-alkyl; or $R^{37A}$ and $R^{38A}$ can be taken together to form an optionally substituted $C_{3-6}$ cycloalkyl.

When $R^{37A}$ is substituted, $R^{37A}$ can be substituted with one or more substituents selected from N-amido, mercapto, alkylthio, an optionally substituted aryl, hydroxy, an optionally substituted heteroaryl, O-carboxy and amino. In some embodiments, $R^{37A}$ can be an unsubstituted $C_{1-6}$-alkyl, such as those described herein. In some embodiments, $R^{37A}$ can be hydrogen. In other embodiments, $R^{37A}$ can be methyl. In some embodiments, $R^{36A}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{36A}$ can be methyl or isopropyl. In some embodiments, $R^{36A}$ can be ethyl or neopentyl. In other embodiments, $R^{36A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{36A}$ can be an optionally substituted cyclohexyl. In still other embodiments, $R^{36A}$ can be an optionally substituted aryl, such as phenyl and naphthyl. In yet still other embodiments, $R^{36A}$ can be an optionally substituted aryl($C_{1-6}$ alkyl). In some embodiments, $R^{36A}$ can be an optionally substituted benzyl. In some embodiments, $R^{36A}$ can be an optionally substituted $C_{1-6}$ haloalkyl, for example, $CF_3$. In some embodiments, $R^{38A}$ can be hydrogen. In other embodiments, $R^{38A}$ can be an optionally substituted $C_{1-4}$-alkyl, such as methyl, ethyl, n-propyl, isopropyl, n-butyl, isobutyl and tert-butyl. In an embodiment, $R^{38A}$ can be methyl. In some embodiments, $R^{37A}$ and $R^{38A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{37A}$ and $R^{38A}$, the carbon to which $R^{37A}$ and $R^{38A}$ are attached may be a chiral center. In some embodiment, the carbon to which $R^{37A}$ and $R^{38A}$ are attached may be a (R)-chiral center. In other embodiments, the carbon to which $R^{37A}$ and $R^{38A}$ are attached may be a (S)-chiral center.

Examples of suitable

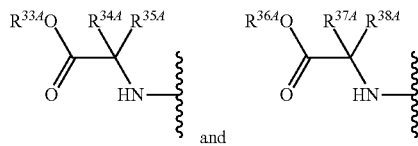

and groups include the following:

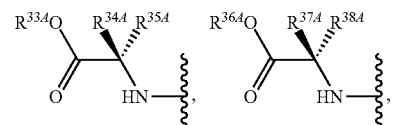

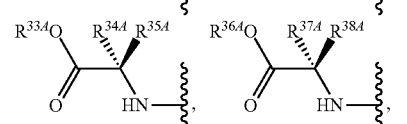

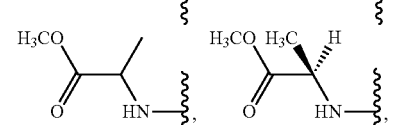

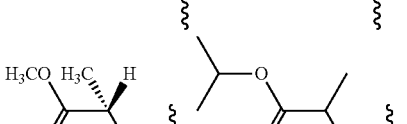

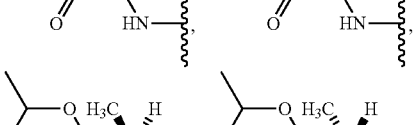

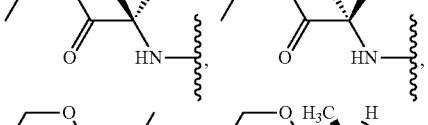

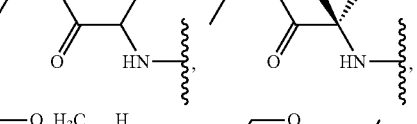

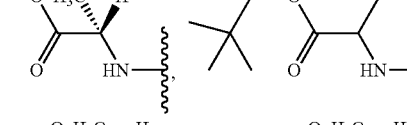

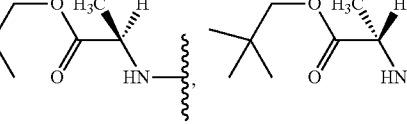

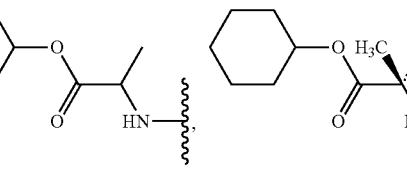

-continued

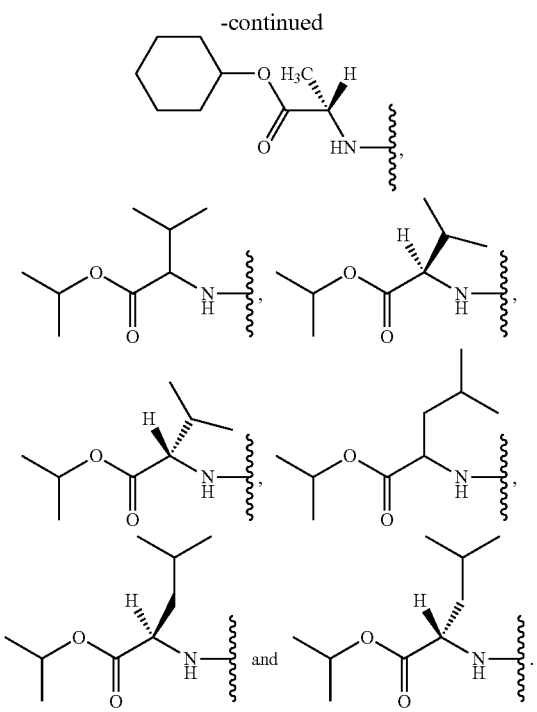

In some embodiments, $R^{10A}$ and $R^{11A}$ can be the same. In some embodiments, $R^{10A}$ and $R^{11A}$ can be different.

In some embodiments, $Z^{3A}$ can be O (oxygen). In other embodiments, $Z^{3A}$ can be S (sulfur). In some embodiments, when $R^{1A}$ is

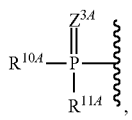

a compound of Formula (I) can be a phosphonic diamide prodrug.

In some embodiments, $R^{1A}$ can be hydrogen. In some embodiments, $R^{1A}$ can be an optionally substituted acyl. In other embodiments, $R^{1A}$ can be —C(=O)$R^{39A}$, wherein $R^{39A}$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, $R^{39A}$ can be a substituted $C_{1-12}$ alkyl. In other embodiments, $R^{39A}$ can be an unsubstituted $C_{1-12}$ alkyl.

In still other embodiments, $R^{1A}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-gly-cine and norleucine. In some embodiments, the O-linked amino acid can have the structure

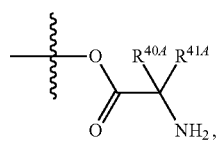

wherein $R^{40A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{41A}$ can be hydrogen or an optionally substituted $C_{1-4}$-alkyl; or $R^{40A}$ and $R^{41A}$ can be taken together to form an optionally substituted $C_{3-6}$ cycloalkyl. Those skilled in the art understand that when $R^{1A}$ is an optionally substituted O-linked amino acid, the oxygen of $R^{1A}$O— of Formula (I) is part of the optionally substituted O-linked amino acid. For example, when $R^{1A}$ is

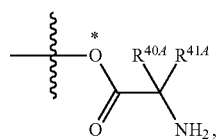

the oxygen indicated with "*" is the oxygen of $R^{1A}$O— of Formula (I).

When $R^{40A}$ is substituted, $R^{40A}$ can be substituted with one or more substituents selected from N-amido, mercapto, alkylthio, an optionally substituted aryl, hydroxy, an optionally substituted heteroaryl, O-carboxy and amino. In some embodiments, $R^{40A}$ can be an unsubstituted $C_{1-6}$-alkyl, such as those described herein. In some embodiments, $R^{40A}$ can be hydrogen. In other embodiments, $R^{40A}$ can be methyl. In some embodiments, $R^{41A}$ can be hydrogen. In other embodiments, $R^{41A}$ can be an optionally substituted $C_{1-4}$-alkyl, such as methyl, ethyl, n-propyl, isopropyl, n-butyl, isobutyl and tert-butyl. In an embodiment, $R^{41A}$ can be methyl. Depending on the groups that are selected for $R^{40A}$ and $R^{41A}$, the carbon to which $R^{40A}$ and $R^{41A}$ are attached may be a chiral center. In some embodiment, the carbon to which $R^{40A}$ and $R^{41A}$ are attached may be a (R)-chiral center. In other embodiments, the carbon to which $R^{40A}$ and $R^{41A}$ are attached may be a (S)-chiral center.

Examples of suitable

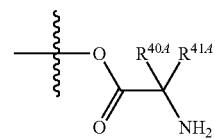

include the following:

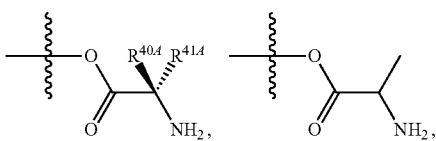

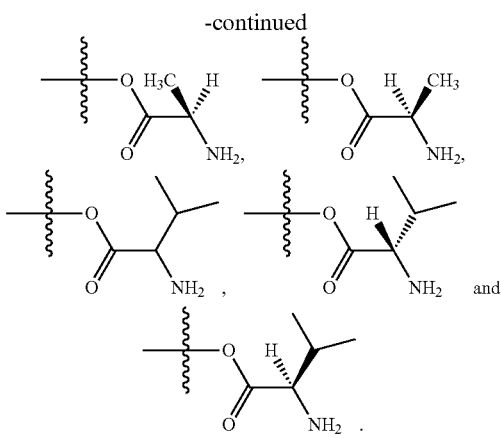

As described herein, in some embodiments, $R^{2A}$ can be a $C_{1-6}$ azidoalkyl. For example, $R^{2A}$ can be an azidomethyl, azidoethyl, azidopropyl, azidobutyl, azidopentyl or azidohexyl. In other embodiments, $R^{2A}$ can be a $C_{1-6}$ aminoalkyl, such as aminomethyl, aminoethyl, aminopropyl, aminobutyl, aminopentyl or aminohexyl.

The groups attached to the 3'-position of the pentose ring can vary. In some embodiments, $R^{3A}$ can be OH. In other embodiments, $R^{3A}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can have the structure

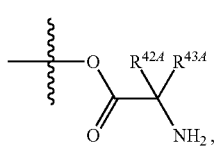

wherein $R^{42A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{43A}$ can be hydrogen or an optionally substituted $C_{1-4}$-alkyl; or $R^{42A}$ and $R^{43A}$ can be taken together to form an optionally substituted $C_{3-6}$ cycloalkyl.

When $R^{42A}$ is substituted, $R^{42A}$ can be substituted with one or more substituents selected from N-amido, mercapto, alkylthio, an optionally substituted aryl, hydroxy, an optionally substituted heteroaryl, O-carboxy and amino. In some embodiments, $R^{42A}$ can be an unsubstituted $C_{1-6}$-alkyl, such as those described herein. In some embodiments, $R^{42A}$ can be hydrogen. In other embodiments, $R^{42A}$ can be methyl. In some embodiments, $R^{43A}$ can be hydrogen. In other embodiments, $R^{43A}$ can be an optionally substituted $C_{1-4}$-alkyl, such as methyl, ethyl, n-propyl, isopropyl, n-butyl, isobutyl and tert-butyl. In an embodiment, $R^{43A}$ can be methyl. Depending on the groups that are selected for $R^{42A}$ and $R^{43A}$, the carbon to which $R^{42A}$ and $R^{43A}$ are attached may be a chiral center. In some embodiment, the carbon to which $R^{42A}$ and $R^{43A}$ are attached may be a (R)-chiral center. In other embodiments, the carbon to which $R^{42A}$ and $R^{43A}$ are attached may be a (S)-chiral center.

Examples of suitable

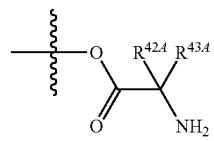

include the following:

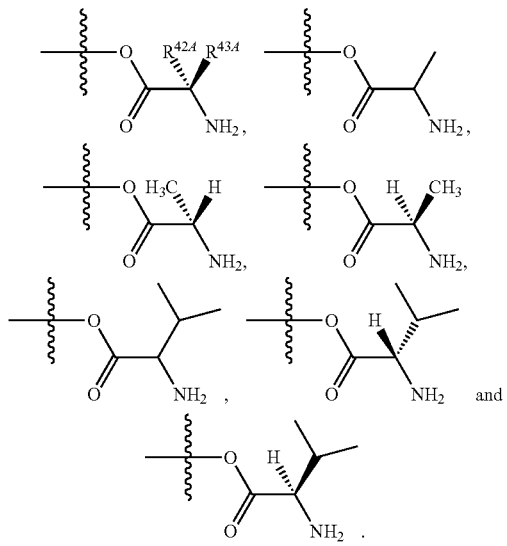

In still other embodiments, $R^{3A}$ can be $-OC(=O)R'''^{A}$, wherein $R'''^{A}$ can be an optionally substituted $C_{1-24}$ alkyl. In some embodiments, $R'''^{A}$ can be a substituted $C_{1-8}$ alkyl. In other embodiments, $R'''^{A}$ can be an unsubstituted $C_{1-8}$ alkyl. In still other embodiments, $R^{3A}$ can be an optionally substituted —O-acyl. In yet still other embodiments, $R^{3A}$ can be $-OC(=O)R^{44A}$, wherein $R^{44A}$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, $R^{44A}$ can be a substituted $C_{1-12}$ alkyl. In other embodiments, $R^{44A}$ can be an unsubstituted $C_{1-12}$ alkyl.

Various substituents can be present at the 2'-position of the pentose ring. In some embodiments, $R^{5A}$ can be hydrogen. In other embodiments, $R^{5A}$ can be halogen, for example, fluoro or chloro. In some embodiments, $R^{4A}$ can be halogen, such as fluoro or chloro. In some embodiments, $R^{5A}$ can be hydrogen and $R^{4A}$ can be halogen. In some embodiments, $R^{5A}$ can be hydrogen and $R^{4A}$ can be fluoro. In other embodiments, $R^{5A}$ can be hydrogen and $R^{4A}$ can be chloro. In other embodiments, $R^{4A}$ and $R^{5A}$ can both be halogen.

A variety of substituents can also be present at the 5'-position of the pentose ring. In some embodiments, both $R^{a1}$ and $R^{a2}$ can be hydrogen. In other embodiments, $R^{a1}$ can be hydrogen and $R^{a2}$ can be deuterium. In still other embodiments, both $R^{a1}$ and $R^{a2}$ can be deuterium. For the 1'-position, in some embodiments, $R^A$ can be hydrogen. In other embodiments, $R^A$ can be deuterium.

In some embodiments, $B^{1A}$ cannot be a substituted or unsubstituted thymine. In other embodiments, $B^{1A}$ cannot be an unsubstituted uracil. In still other embodiments, $B^{1A}$ cannot be cytosine. In some embodiments $R^{1A}$ cannot be H. In some embodiments $R^{1A}$ cannot be H when $B^{1A}$ is an optionally substituted cytosine or an optionally substituted thymine. In some embodiments, $Z^{1A}$ cannot be

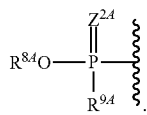

In some embodiments, $R^{1A}$ cannot be hydrogen when $R^{2A}$ is azidomethyl, $R^{3A}$ is hydroxy, $R^{4A}$ is halogen (for example, fluoro), $R^{5A}$ is hydrogen, $R^A$ is hydrogen and $B^{1A}$ is uracil. In some embodiments, $R^{1A}$ cannot be hydrogen when $R^{2A}$ is H$_2$N-methyl, $R^{3A}$ is hydroxy, $R^{4A}$ is halogen (for example, fluoro), $R^{5A}$ is hydrogen, $R^A$ is hydrogen and $B^{1A}$ is uracil. In some embodiments, when $R^{2A}$ is azidomethyl, $R^{3A}$ is hydroxy, $R^{4A}$ is halogen (for example, fluoro), $R^{5A}$ is hydrogen and $R^A$ is hydrogen. then $B^{1A}$ cannot be uracil. In some embodiments, when $R^{2A}$ is H$_2$N-methyl, $R^{3A}$ is hydroxy, $R^{4A}$ is halogen (for example, fluoro), $R^{5A}$ is hydrogen and $R^A$ is hydrogen, then $B^{1A}$ cannot be uracil. In some embodiments, a compound of Formula (I), or a pharmaceutically acceptable salt, cannot be

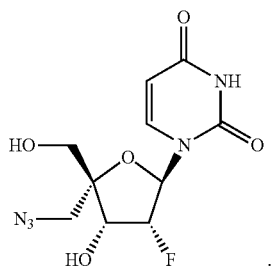

In some embodiments, a compound of Formula (I), or a pharmaceutically acceptable salt, cannot be

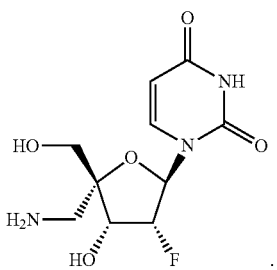

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

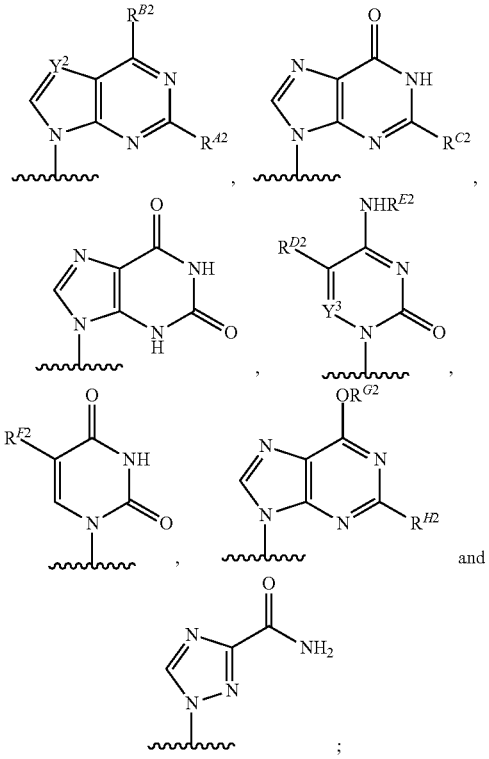

wherein: $R^{A2}$ can be selected from hydrogen, halogen and NHR$^{J2}$, wherein R$^{J2}$ can be selected from hydrogen, —C(=O)R$^{K2}$ and —C(=O)OR$^{L2}$; R$^{B2}$ can be halogen or NHR$^{W2}$, wherein R$^{W2}$ can be selected from hydrogen, an optionally substituted C$_{1-6}$ alkyl, an optionally substituted C$_{2-6}$ alkenyl, an optionally substituted C$_{3-8}$ cycloalkyl, —C(=O)R$^{M2}$ and —C(=O)OR$^{N2}$; and R$^{C2}$ can be hydrogen or NHR$^{O2}$, wherein R$^{O2}$ can be selected from hydrogen, —C(=O)R$^{P2}$ and —C(=O)OR$^{Q2}$; R$^{D2}$ can be selected from hydrogen, deuterium, halogen, an optionally substituted C$_{1-6}$ alkyl, an optionally substituted C$_{2-6}$ alkenyl and an optionally substituted C$_{2-6}$ alkynyl; R$^{E2}$ can be selected from hydrogen, hydroxy, an optionally substituted C$_{1-6}$ alkyl, an optionally substituted C$_{3-8}$ cycloalkyl, —C(=O)R$^{R2}$ and —C(=O)OR$^{S2}$; R$^{F2}$ can be selected from hydrogen, halogen, an optionally substituted C$_{1-6}$ alkyl, an optionally substituted C$_{2-6}$ alkenyl and an optionally substituted C$_{2-6}$ alkynyl; Y$^2$ and Y$^3$ can be independently N (nitrogen) or CR$^{I2}$, wherein R$^{I2}$ can be selected from hydrogen, halogen, an optionally substituted C$_{1-6}$-alkyl, an optionally substituted C$_{2-6}$-alkenyl and an optionally substituted C$_{2-6}$-alkynyl; R$^{G2}$ can be an optionally substituted C$_{1-6}$ alkyl; R$^{H2}$ can be hydrogen or NHR$^{T2}$, wherein R$^{T2}$ can be independently selected from hydrogen, —C(=O)R$^{U2}$ and —C(=O)OR$^{V2}$; and R$^{K2}$, R$^{L2}$, R$^{M2}$, R$^{N2}$, R$^{P2}$, R$^{Q2}$, R$^{R2}$, R$^{S2}$, R$^{U2}$ and R$^{V2}$ can be independently selected from C$_{1-6}$ alkyl, C$_{2-6}$ alkenyl, C$_{2-6}$ alkynyl, C$_{3-6}$ cycloalkyl, C$_{3-6}$ cycloalkenyl, C$_{6-10}$ aryl, heteroaryl, heterocyclyl, aryl(C$_{1-6}$ alkyl), heteroaryl($C_{1-6}$ alkyl) and heterocyclyl($C_{1-6}$ alkyl). In some embodiments, the structures shown above can be modified by replacing one or more hydrogens with substituents selected from the list of substituents provided for the definition of "substituted."

In some embodiments, $B^{1A}$ can be

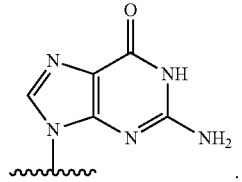

In other embodiments, $B^{1A}$ can be

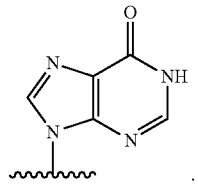

In still other embodiments, $B^{1A}$ can be

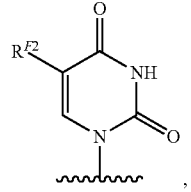

such as

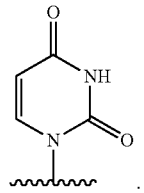

In yet still other embodiments, $B^{1A}$ can be

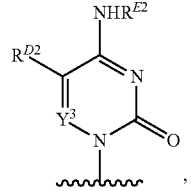

for example,

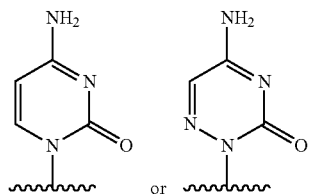

In some embodiments, $R^{D2}$ can be hydrogen. In other embodiments, $B^{1A}$ can be

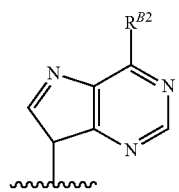

In some embodiments, $R^{B2}$ can be $NH_2$. In other embodiments, $R^{B2}$ can be $NHR^{W2}$, wherein $R^{W2}$ can be —C(=O)$R^{M2}$ or —C(=O)O$R^{N2}$. In still other embodiments, $B^{1A}$ can be

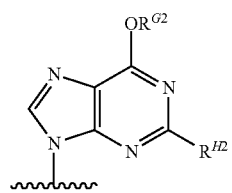

In some embodiments, $B^{1A}$ can be

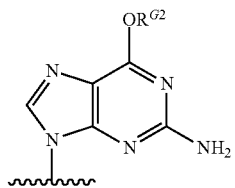

In some embodiments, a compound of Formula (I) can have the structure:

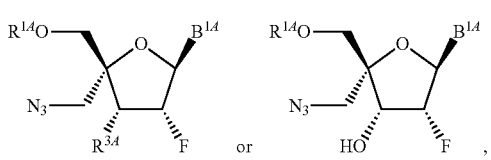

or a pharmaceutically acceptable salt of the foregoing. In other embodiments, a compound of Formula (I) can have the structure:

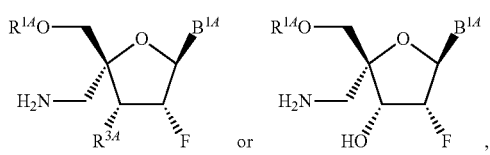

or a pharmaceutically acceptable salt of the foregoing. In some embodiments of this paragraph, $B^{1A}$ can be an optionally substituted purine base. In other embodiments of this paragraph, $B^{1A}$ can be an optionally substituted pyrimidine base. In some embodiments of this paragraph, $B^{1A}$ can be guanine. In other embodiments of this paragraph, $B^{1A}$ can be thymine. In still other embodiments of this paragraph, $B^{1A}$ can be cytosine. In yet still other embodiments of this paragraph, $B^{1A}$ can be uracil. In some embodiments of this paragraph, $B^{1A}$ can be adenine. In some embodiments of this paragraph, $R^{1A}$ can be hydrogen. In other embodiments of this paragraph, $R^{1A}$ can be an optionally substituted acyl. In still other embodiments of this paragraph, $R^{1A}$ can be mono-, di- or tri-phosphate. In yet other embodiments of this paragraph, $R^{1A}$ can be phosphoramidate prodrug, such as an aryl phosphoramidate prodrug. In some embodiments of this paragraph, $R^{1A}$ can be an acyloxyalkyl ester phosphate prodrug. In other embodiments of this paragraph, $R^{1A}$ can be a S-acylthioethyl (SATE) prodrug. In still other embodiments, $R^{1A}$ can be a phosphonic diamide prodrug. In yet still other embodiments, of this paragraph, $R^{1A}$ can be a cyclic 1-aryl-1,3-propanyl ester (HepDirect) prodrug moiety. In some embodiments of this paragraph, $R^{1A}$ be a cyclosaligenyl (cycloSal) prodrug.

Examples of suitable compounds of Formula (I) include, but are not limited to the following:

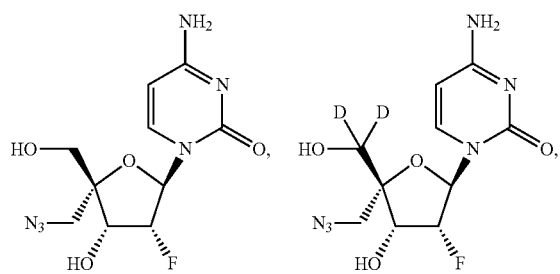

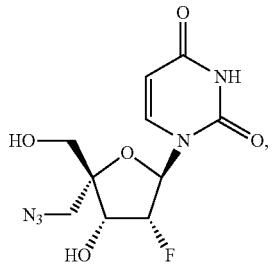

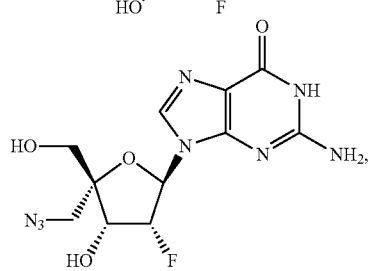

-continued

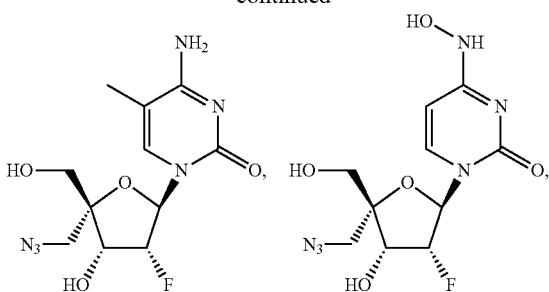

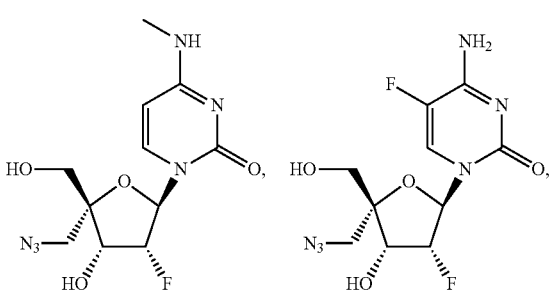

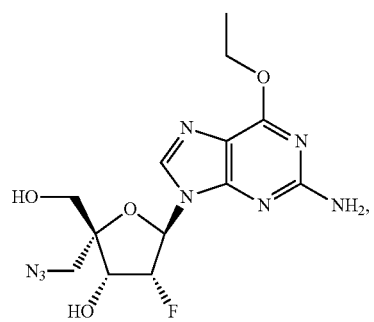

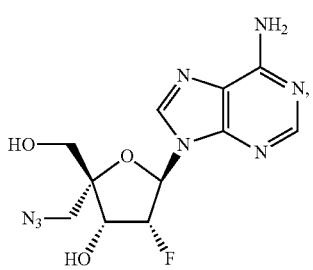

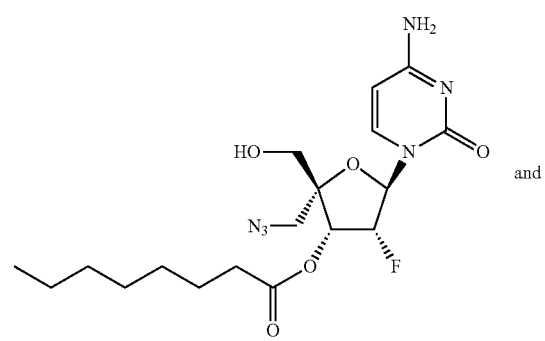

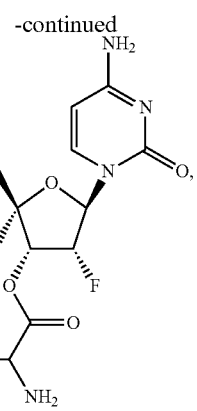
or a pharmaceutically acceptable salt of the foregoing.
Further examples of suitable compounds of Formula (I) include, but are not limited to the following:
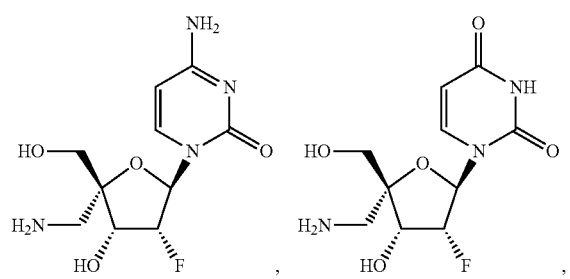
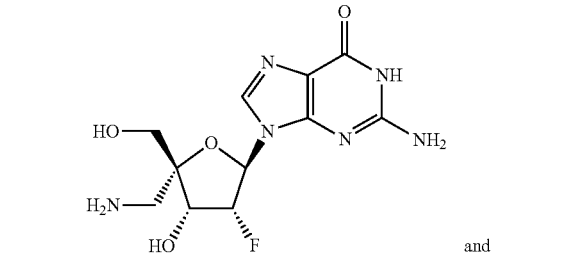
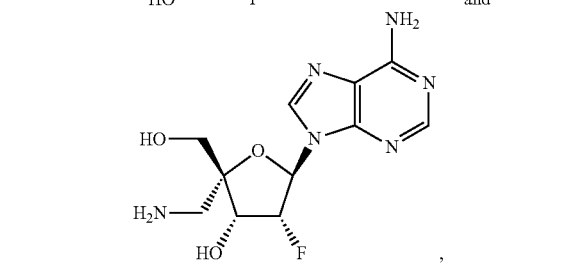
or a pharmaceutically acceptable salt of the foregoing.
Additional examples of a compound of Formula (I) include the following:
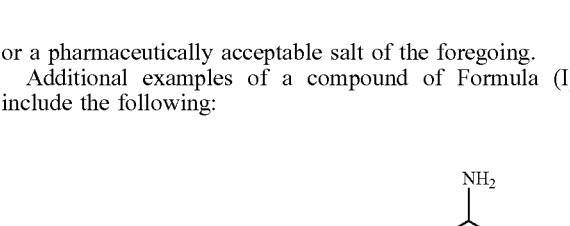
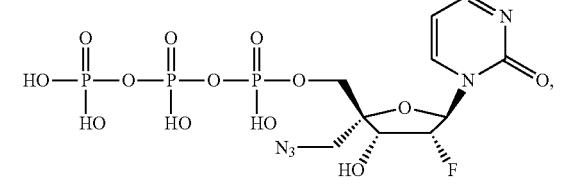
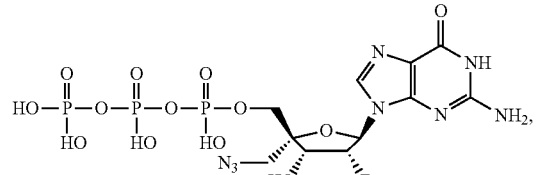
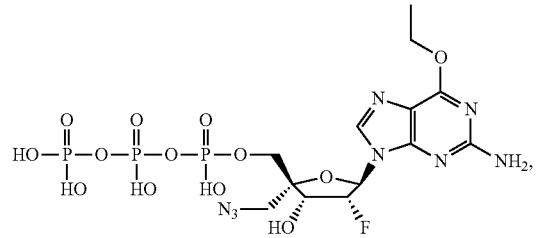
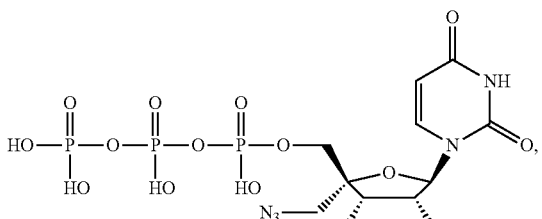
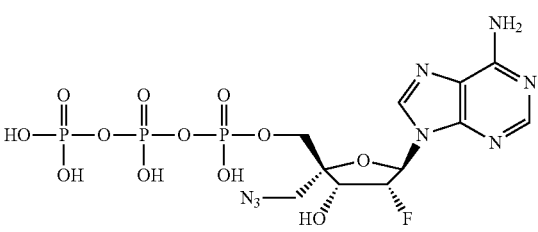
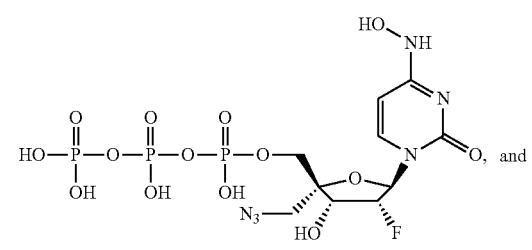
and -continued
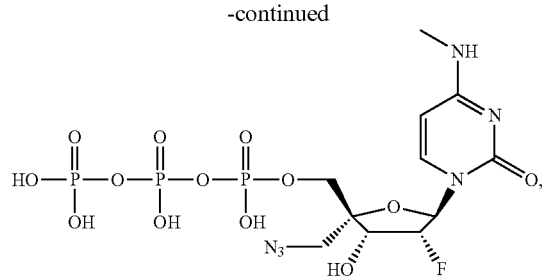
or a pharmaceutically acceptable salt of the foregoing.
Examples of a compound of Formula (I) include the following:
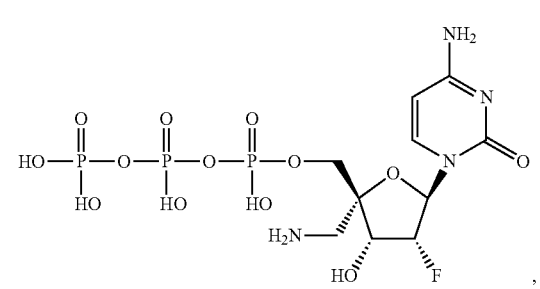
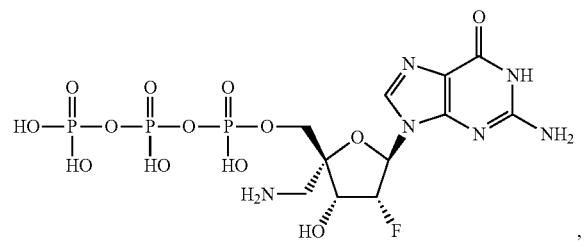
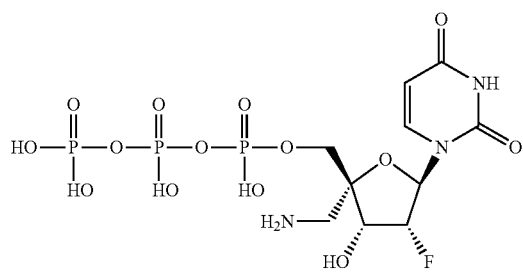
and
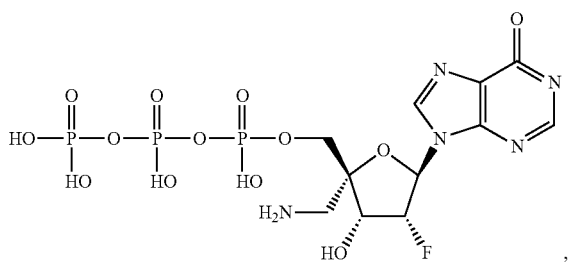
or a pharmaceutically acceptable salt of the foregoing.
Further examples of a compound of Formula (I) include, but are not limited to the following:
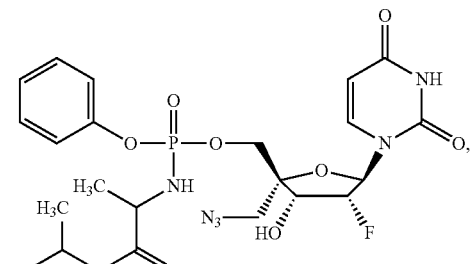
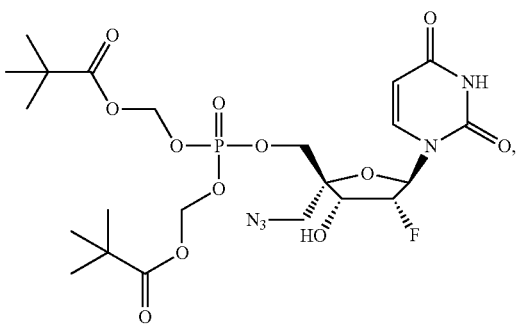
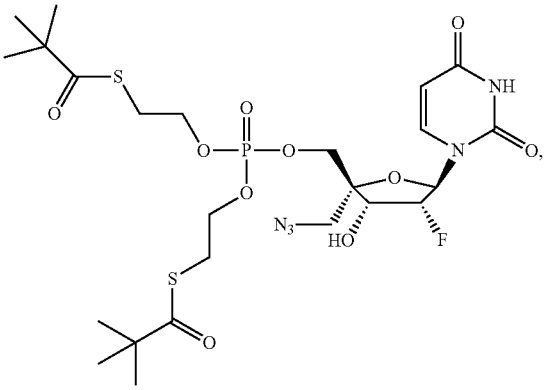
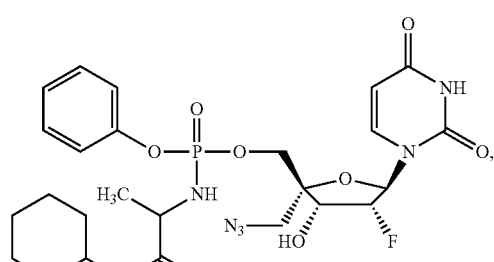
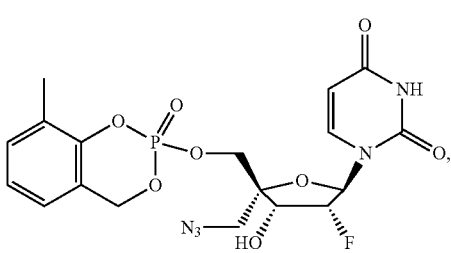

41
-continued
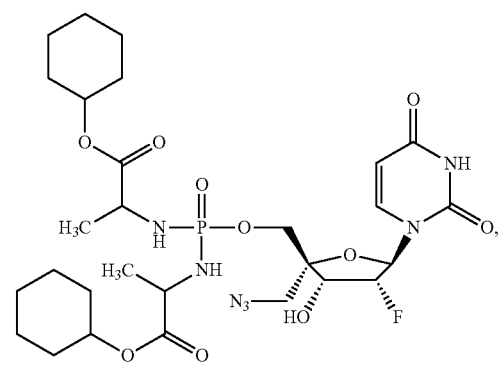
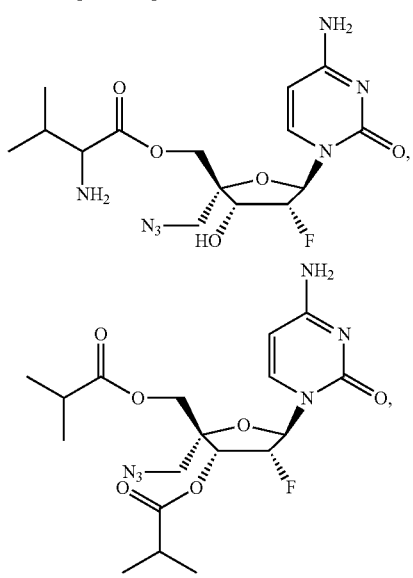
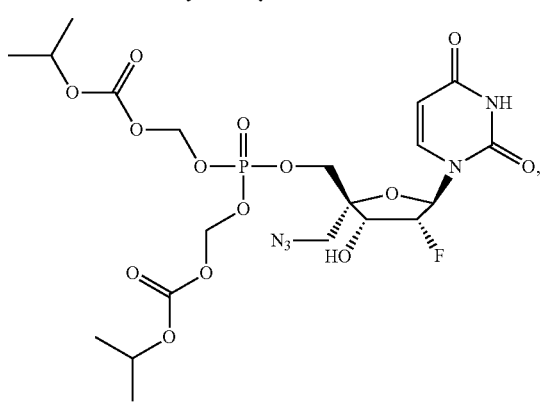
42
-continued
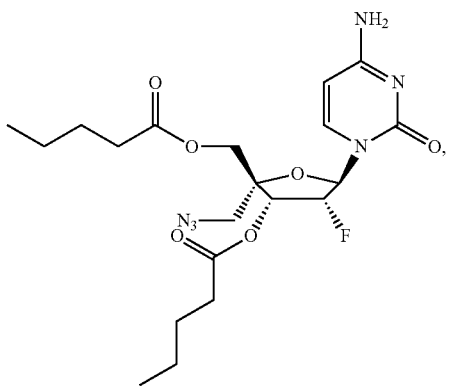
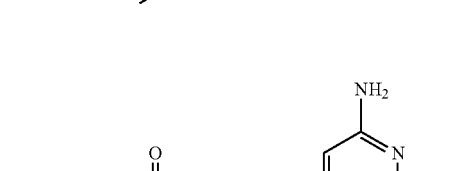
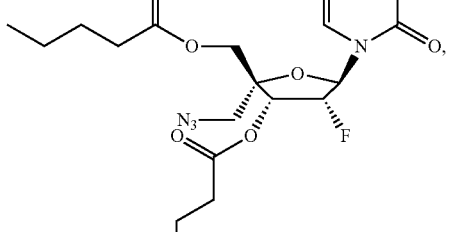
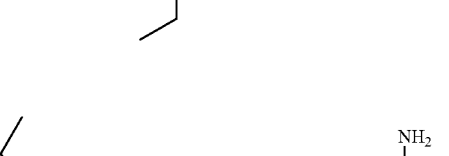
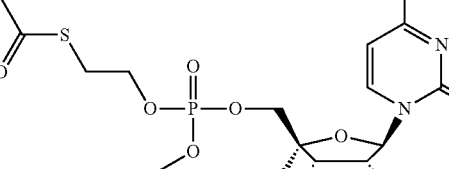
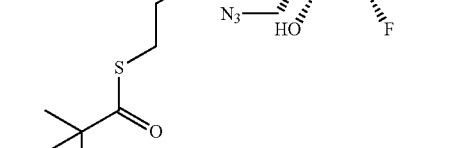

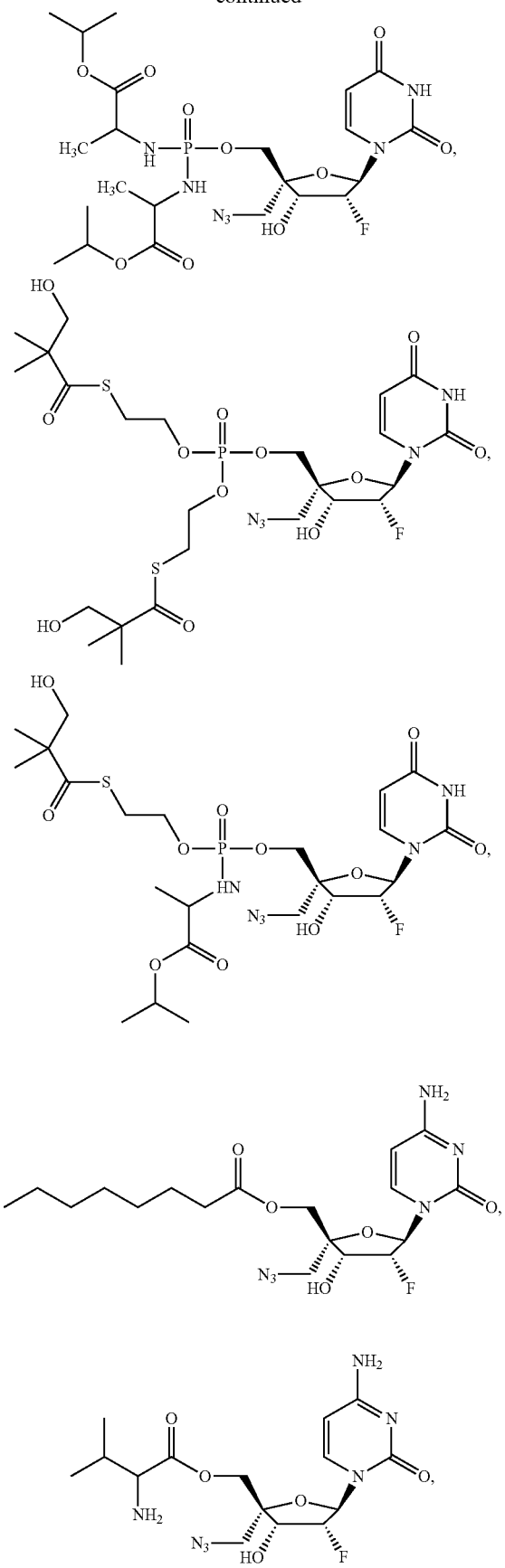

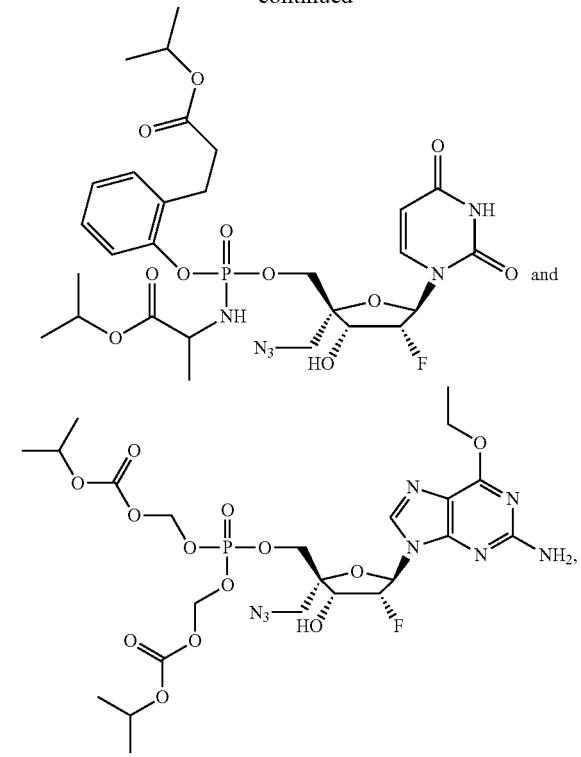

or a pharmaceutically acceptable salt of the foregoing.

Synthesis

Compounds of Formula (I) and those described herein may be prepared in various ways. Some compounds of Formula (I) can be obtained commercially and/or prepared utilizing known synthetic procedures. General synthetic routes to the compounds of Formula (I), and some examples of starting materials used to synthesize the compounds of Formula (I) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

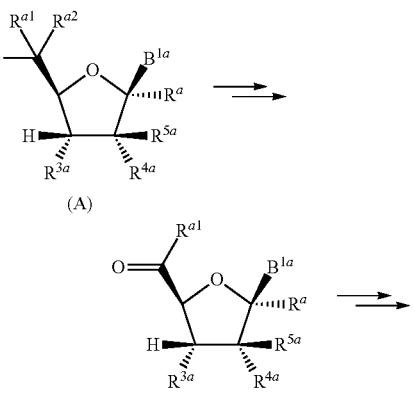

-continued

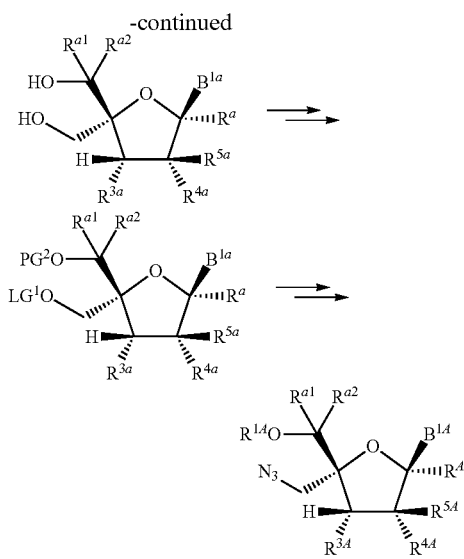

Compounds of Formula (I), where $R^{2A}$ is a $C_{1-6}$ azidoalkyl can be prepared from a nucleoside, for example, a nucleoside of Formula (A). In Scheme 1, $R^a$, $R^{3a}$, $R^{4a}$, $R^{5a}$ and $B^{1a}$ can be the same as $R^A$, $R^{3A}$, $R^{4A}$, $R^{5A}$ and $B^{1A}$ as described herein for Formula (I), $PG^1$ can be a suitable protecting group and $LG^1$ can be a suitable leaving group. The 5'-position of the nucleoside can be oxidized to an aldehyde using methods known to those skilled in the art. Suitable oxidation conditions include, but are not limited to, Moffatt oxidation, Swern oxidation and Corey-Kim oxidation; and suitable oxidizing agents include, but are not limited to, Dess-Martin periodinane, IBX (2-iodoxybenzoic acid), TPAP/NMO (tetrapropylammonium perruthenate/N-methylmorpholine N-oxide), Swern oxidation reagent, PCC (pyridinium chlorochromate), PDC (pyridinium dichromate), sodium periodate, Collin's reagent, ceric ammonium nitrate CAN, $Na_2Cr_2O_7$ in water, $Ag_2CO_3$ on celite, hot $HNO_3$ in aqueous glyme, $O_2$-pyridine CuCl, $Pb(OAc)_4$-pyridine and benzoyl peroxide-$NiBr_2$. A hydroxymethyl group can be added to the 4'-position of the pentose ring along with the reduction of the aldehyde to an alcohol. The hydroxymethyl group can be added via a condensation reaction using formaldehyde and a base, such as sodium hydroxide. After addition of the hydroxymethyl group, reduction of the intermediate compound with a 4'-hydroxymethyl group can be conducted using a reducing reagent. Examples of suitable reducing agents include, but are not limited to, $NaBH_4$ and $LiAlH_4$. A suitable leaving group, such as a triflate, can be formed by replacing the hydrogen of the hydroxymethyl group attached to the 4'-position, and the oxygen attached to the 5'-position can be protected with a suitable protecting group (for example, by cyclization with the base, $B^{1a}$, or with a separate protecting group). The leaving group can be replaced with an azido group using a metal azide reagent, for example, sodium azide.

Scheme 2

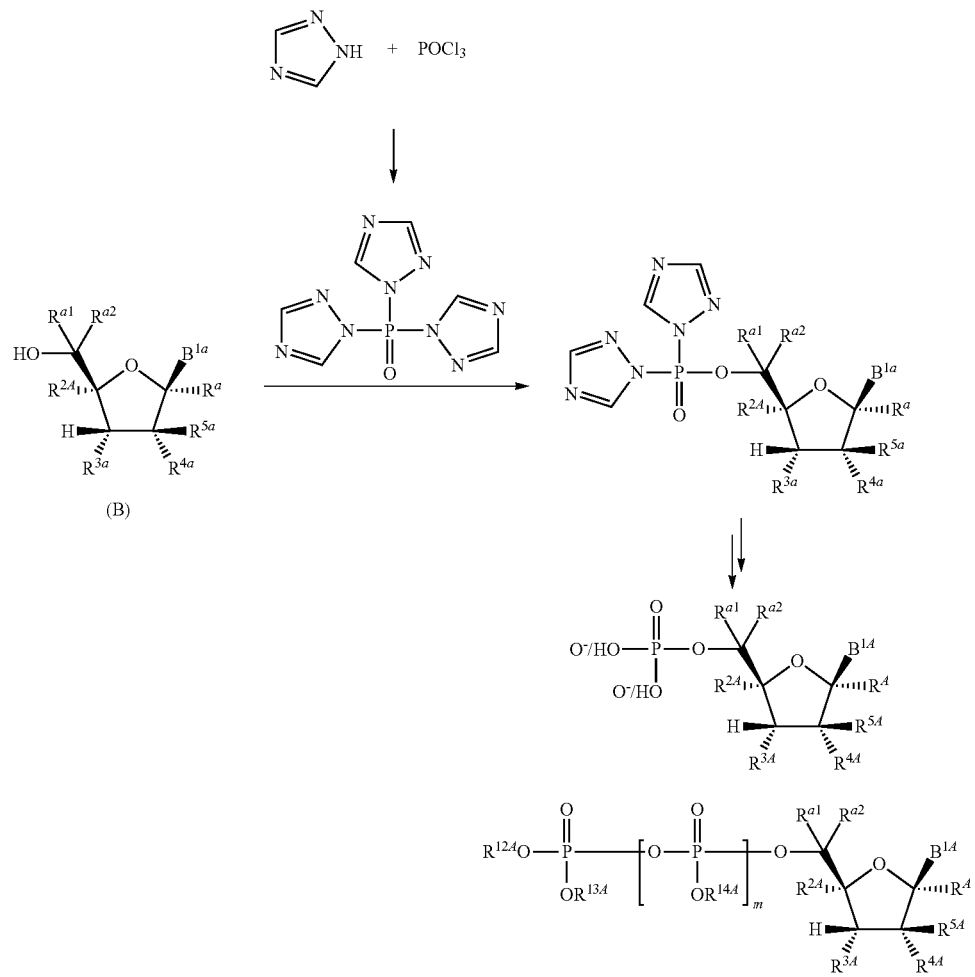

Scheme 3

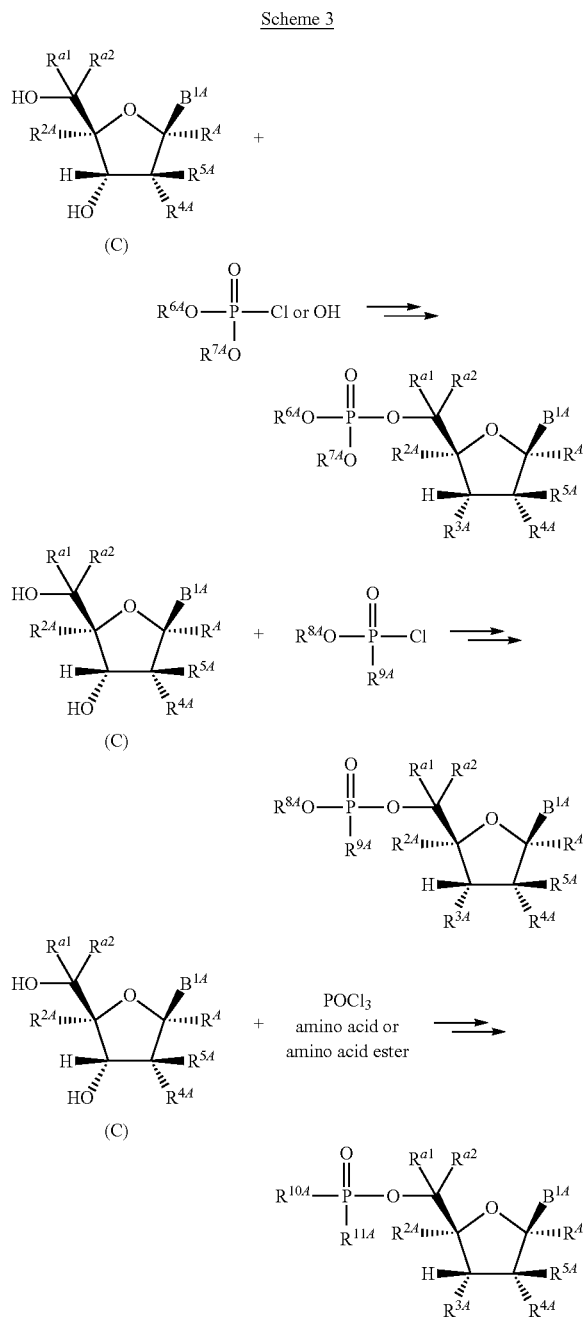

Compounds of Formula (I) having a phosphorus containing group attached to the 5'-position of the pentose ring can be prepared using various methods known to those skilled in the art. Examples of methods are shown in Schemes 2 and 3. In Schemes 2 and 3, $R^a$, $R^{2a}$, $R^{3a}$, $R^{4a}$, $R^{5a}$ and $B^{1a}$ can be the same as $R^A$, $R^{2A}$, $R^{3A}$, $R^{4A}$, $R^{5A}$ and $B^{1A}$ as described herein for Formula (I). A phosphorus containing precursor can be coupled to the nucleoside, for example, a compound of Formula (B). As shown in Scheme 2, following the coupling of the phosphorus containing precursor, any leaving groups can be cleaved under suitable conditions, such as hydrolysis. Further phosphorus containing groups can be added using methods known to those skilled in the art, for example using a pyrophosphate.

In some embodiments, an alkoxide can be generated from a compound of Formula (C) using an organometallic reagent, such as a Grignard reagent. The alkoxide can be coupled to the phosphorus containing precursor. Suitable Grignard reagents are known to those skilled in the art and include, but are not limited to, alkylmagnesium chlorides and alkylmagnesium bromides. In some embodiments, an appropriate base can be used. Examples of suitable bases include, but are not limited to, an amine base, such as an alkylamine (including mono-, di- and tri-alkylamines (e.g., triethylamine)), optionally substituted pyridines (e.g. collidine) and optionally substituted imidazoles (e.g., N-methylimidazole)). Alternatively, a phosphorus containing precursor can be added to the nucleoside and form a phosphite. The phosphite can be oxidized to a phosphate using conditions known to those skilled in the art. Suitable conditions include, but are not limited to, meta-chloroperoxybenzoic acid (MCPBA) and iodine as the oxidizing agent and water as the oxygen donor.

A $C_{1-6}$ azidoalkyl at the 4'-position can be reduced to a $C_{1-6}$ aminoalkyl. Various reduction agents/conditions known to those skilled in the art can be utilized. For example, the azido group can be reduced to an amino group via hydrogenation (for example, $H_2$—Pd/C or $HCO_2NH_4$—Pd/C), Staudinger Reaction, $NaBH_4/CoCl_2.6H_2O$, $Fe/NH_4Cl$ or $Zn/NH_4Cl$.

When compounds of Formula (I) have $Z^{1A}$, $Z^{2A}$ or $Z^{3A}$ being sulfur, the sulfur can be added in various manners known to those skilled in the art. In some embodiments, the sulfur can be part of the phosphorus containing precursor, for example,

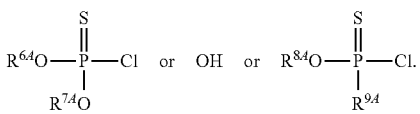

Alternatively, the sulfur can be added using a sulfurization reagent. Suitable sulfurization agents are known to those skilled in the art, and include, but are not limited to, elemental sulfur, Lawesson's reagent, cyclooctasulfur, 3H-1,2-Benzodithiole-3-one-1,1-dioxide (Beaucage's reagent), 3-((N,N-dimethylaminomethylidene)amino)-3H-1,2,4-dithiazole-5-thione (DDTT) and bis(3-triethoxysilyl)propyl-tetrasulfide (TEST).

Suitable phosphorus containing precursors can be commercially obtained or prepared by synthetic methods known to those skilled in the art. Examples of general structures of phosphorus containing precursors are shown in Schemes 2 and 3.

During the synthesis of any of the compounds described herein, if desired, any hydroxy groups attached to the pentose ring, and any —NH and/or $NH_2$ groups present on the $B^{1a}$, can be protected with one or more suitable protecting groups. Suitable protecting groups are described herein. For example, when $R^{3a}$ is a hydroxy group, $R^{3a}$ can be protected with a triarylmethyl group or a silyl group. Likewise, any —NH and/or $NH_2$ groups present on the $B^{1a}$ can be protected, such as with a triarylmethyl and a silyl group(s). Examples of triarylmethyl groups include but are not limited to, trityl, monomethoxytrityl (MMTr), 4,4'-dimethoxytrityl (DMTr), 4,4',4"-trimethoxytrityl (TMTr), 4,4',4"-tris-(benzoyloxy)trityl (TBTr), 4,4',4"-tris(4,5-dichlorophthalimido)trityl (CPTr), 4,4',4"-tris(levulinyloxy)trityl (TLTr), p-anisyl-1-naphthylphenylmethyl, di-o-anisyl- 1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl) xanthen-9-yl (Mox), 4-decyloxytrityl, 4-hexadecyloxytrityl, 4,4'-dioctadecyltrityl, 9-(4-octadecyloxyphenyl) xanthen-9-yl, 1,1'-bis-(4-methoxyphenyl)-1'-pyrenylmethyl, 4,4',4''-tris-(tert-butylphenyl) methyl (TTTr) and 4,4'-di-3,5-hexadienoxytrityl. Examples of silyl groups include, but are not limited to, trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy] methyl. Those skilled in the art will appreciate that groups attached to the pentose ring and any —NH and/or $NH_2$ groups present on the $B^{1a}$ can be protected with various protecting groups, and any protecting groups present can be exchanged for other protecting groups. The selection and exchange of the protecting groups is within the skill of those of ordinary skill in the art. Any protecting group(s) can be removed by methods known in the art, for example, with an acid (e.g., a mineral or an organic acid), a base or a fluoride source.

Pharmaceutical Compositions

Some embodiments described herein relates to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use:

Some embodiments described herein relate to a method of ameliorating, treating and/or preventing a paramyxovirus viral infection, which can include administering to a subject an effective amount of one or more compounds described herein, or a pharmaceutical composition that includes one or more compounds described herein (e.g., a compound of Formula (I), or a pharmaceutically acceptable salt thereof). In some embodiments, the subject is identified as suffering from a paramyxovirus viral infection.

Other embodiments described herein relate to a method of inhibiting viral replication of a paramyxovirus, which can include contacting a cell infected with the virus with an effective amount of a compound of Formula (I), or a pharmaceutically acceptable salt thereof, and/or a pharmaceutical composition that includes one or more compounds described herein (e.g., a compound of Formula (I), or a pharmaceutically acceptable salt thereof). For example, a compound of Formula (I), or a pharmaceutically acceptable salt, can act as a chain-terminator and inhibit replication of the virus.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a paramyxovirus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a paramyxovirus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of a paramyxovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the polymerase complex of a paramyxovirus.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate an upper respiratory viral infection caused by a paramyxovirus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate a lower respiratory viral infection caused by a paramyxovirus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate one or more symptoms of an infection caused by a paramyxovirus infection (such as those described herein).

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate bronchiolitis and/or tracheobronchitis due to a paramyxovirus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate pneumonia due to a paramyxovirus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate croup due to a paramyxovirus infection.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a respiratory syncytial viral (RSV) infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a respiratory syncytial viral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of a respiratory syncytial virus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the RSV polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate an upper respiratory viral infection caused by RSV infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate a lower respiratory viral infection caused by RSV infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate one or more symptoms of an infection caused by RSV infection (such as those described herein).

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate bronchiolitis and/or tracheobronchitis due to a RSV infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate pneumonia due to a RSV infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate croup due to a RSV infection.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a HPIV-1 infection and/or HPIV-3 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a HPIV-1 infection and/or HPIV-3 infection. In some embodiments, an effective amount of one or more compounds of Formula (I), or a pharmaceutically acceptable salt thereof, or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of HPIV-1 and/or HPIV-3. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the HPIV-1 polymerase complex and/or HPIV-3 polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a HPIV-2 infection and/or HPIV-4 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a HPIV-2 infection and/or HPIV-4 infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of HPIV-2 and/or HPIV-4. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the HPIV-2 polymerase complex and/or HPIV-4 polymerase complex.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to treat and/or ameliorate a metapneumoviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to prevent a metapneumoviral infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the replication of a metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used to inhibit the metapneumovirus polymerase complex. In some embodiments, including those of this paragraph, the metapneumovirus can be a human metapneumovirus.

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate an upper respiratory viral infection caused by a virus selected from a RSV virus, a parainfluenza virus and a metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate a lower respiratory viral infection caused by a virus selected from a RSV virus, a parainfluenza virus and a metapneumovirus. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate one or more symptoms of an infection caused by a virus selected from a RSV virus, a parainfluenza virus and a metapneumovirus (such as those described herein).

In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate bronchiolitis and/or tracheobronchitis due to a RSV virus infection, a parainfluenza virus infection and a metapneumovirus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be used treat and/or ameliorate pneumonia due to a RSV virus infection, a parainfluenza virus infection and a metapneumovirus infection. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof)

can be used treat and/or ameliorate croup due to a RSV virus infection, a parainfluenza virus infection and a metapneumovirus infection.

The one or more compounds of Formula (I), or a pharmaceutically acceptable salt thereof, that can be used to treat, ameliorate and/or prevent a paramyxovirus viral infection can be a compound of Formula (I), or pharmaceutically acceptable salt thereof, provided in any of the embodiments described in paragraphs [0083]-[0130].

As used herein, the terms "prevent" and "preventing," mean lowering the efficiency of viral replication and/or inhibiting viral replication to a greater degree in a subject who receives the compound compared to a subject who does not receive the compound. Examples of forms of prevention include prophylactic administration to a subject who has been or may be exposed to an infectious agent, such as a paramyxovirus (e.g., RSV).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, an effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a paramyxovirus viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator of disease response.

In some embodiments, an effective amount of a compound of Formula (I), or a pharmaceutically acceptable salt thereof, is an amount that is effective to reduce viral titers to undetectable levels, for example, to about 1000 to about 5000, to about 500 to about 1000, or to about 100 to about 500 genome copies/mL serum. In some embodiments, an effective amount of a compound of Formula (I), or a pharmaceutically acceptable salt thereof, is an amount that is effective to reduce viral load compared to the viral load before administration of the compound of Formula (I), or a pharmaceutically acceptable salt thereof. For example, wherein the viral load is measure before administration of the compound of Formula (I), or a pharmaceutically acceptable salt thereof, and again after completion of the treatment regime with the compound of Formula (I), or a pharmaceutically acceptable salt thereof (for example, 1 week after completion). In some embodiments, an effective amount of a compound of Formula (I), or a pharmaceutically acceptable salt thereof, can be an amount that is effective to reduce viral load to lower than about 100 genome copies/mL serum. In some embodiments, an effective amount of a compound of Formula (I), or a pharmaceutically acceptable salt thereof, is an amount that is effective to achieve a reduction in viral titer in the serum of the subject in the range of about 1.5-log to about a 2.5-log reduction, about a S-log to about a 4-log reduction, or a greater than about 5-log reduction compared to the viral load before administration of the compound of Formula (I), or a pharmaceutically acceptable salt thereof. For example, wherein the viral load is measure before administration of the compound of Formula (I), or a pharmaceutically acceptable salt thereof, and again after completion of the treatment regime with the compound of Formula (I), or a pharmaceutically acceptable salt thereof (for example, 1 week after completion).

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of a paramyxovirus relative to pre-treatment levels in a subject, as determined after completion of the treatment regime (for example, 1 week after completion). In some embodiments, a compound of Formula (I), or a pharmaceutically acceptable salt thereof, can result in a reduction of the replication of a paramyxovirus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of paramyxovirus replication in the range of 1 to 1.5 log, 1.5 log to 2 log, 2 log to 2.5 log, 2.5 to 3 log, 3 log to 3.5 log or 3.5 to 4 log more reduction of paramyxovirus replication compared to the reduction of paramyxovirus reduction achieved by ribavirin (Virazole®), or may achieve the same reduction as that of ribavirin (Virazole®) therapy in a shorter period of time, for example, in one week, two weeks, one month, two months, or three months, as compared to the reduction achieved after six months of ribavirin (Virazole®) therapy.

In some embodiments, an effective amount of a compound of Formula (I), or a pharmaceutically acceptable salt thereof, is an amount that is effective to achieve a sustained viral response, for example, non-detectable or substantially non-detectable paramyxovirus RNA (e.g., less than about 500, less than about 400, less than about 200, or less than about 100 genome copies per milliliter serum) is found in the subject's serum for a period of at least about one week, two weeks, one month, at least about two months, at least about three months, at least about four months, at least about five months, or at least about six months following cessation of therapy.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with RSV that is resistant to one or more different anti-RSV agents (for example, ribavirin) to ameliorate and/or treat a RSV infection. In some embodiments, development of one or more resistant RSV strains can be delayed when subjects are treated with a compound of Formula (I), or a pharmaceutically acceptable salt thereof, compared to the development of one or more RSV strains resistant to other anti-RSV agents.

In some embodiments, a compound of Formula (I), or a pharmaceutically acceptable salt thereof, can decrease the percentage of subjects that experience complications from a RSV viral infection compared to the percentage of subjects that experience complication being treated with ribavirin. For example, the percentage of subjects being treated with a compound of Formula (I), or a pharmaceutically acceptable salt thereof, that experience complications can be 10%, 25%, 40%, 50%, 60%, 70%, 80% and 90% less compared to subjects being treated with ribavirin.

In some embodiments, a compound of Formula (I), or a pharmaceutically acceptable salt thereof, or a pharmaceutical composition that includes a compound described herein, can be used in combination with one or more additional agent(s). In some embodiments, a compound of Formula (I), or a pharmaceutically acceptable salt thereof, can be used in combination with one or more agents currently used for treating RSV. For example, the additional agent can be ribavirin, palivizumab and RSV-IGIV. For the treatment of RSV, additional agents include but are not limited to ALN-RSV01 (an siRNA agent with the sense strand sequence (5' to 3') GGCUCUUAGCAAAGUCAAGdTdT (SEQ ID NO. 1) and the antisense strand sequence (5' to 3') CUUGAC-UUUGCUAAGAGCCdTdT (SEQ ID NO. 2), Alnylam Pharmaceuticals, U.S. Publication No. 2009/0238772, filed Dec. 15, 2008), BMS-433771 (1-cyclopropyl-3-[[1-(4-hydroxybutyl)benzimidazol-2-yl]methyl]imidazo[4,5-c]pyridin-2-one), RFI-641 4,4"-bis-{4,6-bis-[3-(bis-carbamoylmethyl-sulfamoyl)-phenylamino]-(1,3,5)triazin-2-ylamino}-biphenyl-2,2"-disulfonic-acid), RSV604 ((S)-1-(2-fluorophenyl)-3-(2-oxo-5-phenyl-2,3-dihydro-1H-benzo[e][1,4]diazepin-3-yl)urea), MDT-637 5,5'-bis[1-(((5-amino-1H-tetrazolyl)imino)methyl)]2,2',4"-methylidynetrisphenol), BTA9881 ((R)-9b-(4-chlorophenyl)-1-(4-fluorobenzoyl)-2,3-dihydro-1H-imidazo[1',2':1,2]pyrrolo[3,4-c]pyridin-5(9bH)-one), TMC-353121 (2-[[6-[[[2-(3-Hydroxypropyl)-5-methylphenyl]amino]methyl]-2-[[3-(morpholin-4-yl)propyl]amino]benzimidazol-1-yl]methyl]-6-methylpyridin-3-ol) (Tibotec), MBX-300 ([2,2-bis(docosyloxy-oxymethyl)propyl-5-acetoamido-3,5-dideoxy-4,7,8,9-tetra-O-(sodium-oxysulfonyl)-D-glycero-D-galacto-2-nonulopyranosid] onate), YM-53403 (6-{4-[(biphenyl-2-ylcarbonyl)amino]benzoyl}-N-cyclopropyl-5,6-dihydro-4H-thieno[3,2-d][1]benzazepine-2-carboxamide), motavizumab (Medi-524, MedImmune), Medi-559 (Recombinant RSV A2 cp248/404/1030/ΔSH), Medi-534 (vector vaccine candidate recombinant bovine/human parainfluenza virus type 3 (PIV3)/RSV F2), Medi-557, RV568 and a RSV-F Particle Vaccine (Novavax).

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

A potential advantage of utilizing a compound of Formula (I), or a pharmaceutically acceptable salt thereof, in combination with one or more additional agent(s) described in paragraph [0173], including pharmaceutically acceptable salts and prodrugs thereof, may be a reduction in the required amount(s) of one or more compounds of paragraph [0173] (including pharmaceutically acceptable salts and prodrugs thereof) that is effective in treating a disease condition disclosed herein (for example, RSV), as compared to the amount required to achieve same therapeutic result when one or more compounds described in paragraph [0173], including pharmaceutically acceptable salts and prodrugs thereof, are administered without a compound of Formula (I), or a pharmaceutically acceptable salt thereof. For example, the amount of a compound described in paragraph [0173], including a pharmaceutically acceptable salt and prodrug thereof, can be less compared to the amount of the compound described in paragraph [0173], including a pharmaceutically acceptable salt and prodrug thereof, needed to achieve the same viral load reduction when administered as a monotherapy. Another potential advantage of utilizing a compound of Formula (I), or a pharmaceutically acceptable salt thereof, in combination with one or more additional agent(s) described in paragraph [0173], including pharmaceutically acceptable salts and prodrugs thereof, is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) described in paragraph [0173], including pharmaceutically acceptable salts and prodrugs thereof, may include little to no cross resistance between a compound of Formula (I), or a pharmaceutically acceptable salt thereof, and one or more additional agent(s) described in paragraph [0173] (including pharmaceutically acceptable salts and prodrugs thereof); different routes for elimination of a compound of Formula (I), or a pharmaceutically acceptable salt thereof, and one or more additional agent(s) described in paragraph [0173]

(including pharmaceutically acceptable salts and prodrugs thereof); little to no overlapping toxicities between a compound of Formula (I), or a pharmaceutically acceptable salt thereof, and one or more additional agent(s) described in paragraph [0173] (including pharmaceutically acceptable salts and prodrugs thereof); little to no significant effects on cytochrome P450; and/or little to no pharmacokinetic interactions between a compound of Formula (I), or a pharmaceutically acceptable salt thereof, and one or more additional agent(s) described in paragraph [0173] (including pharmaceutically acceptable salts and prodrugs thereof).

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Example 1

Preparation of Compound 1A

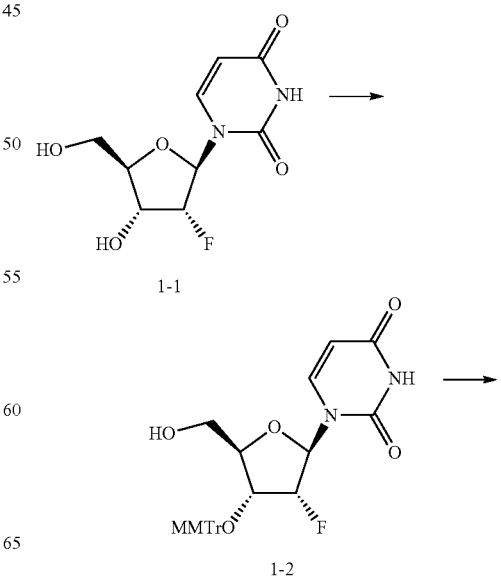

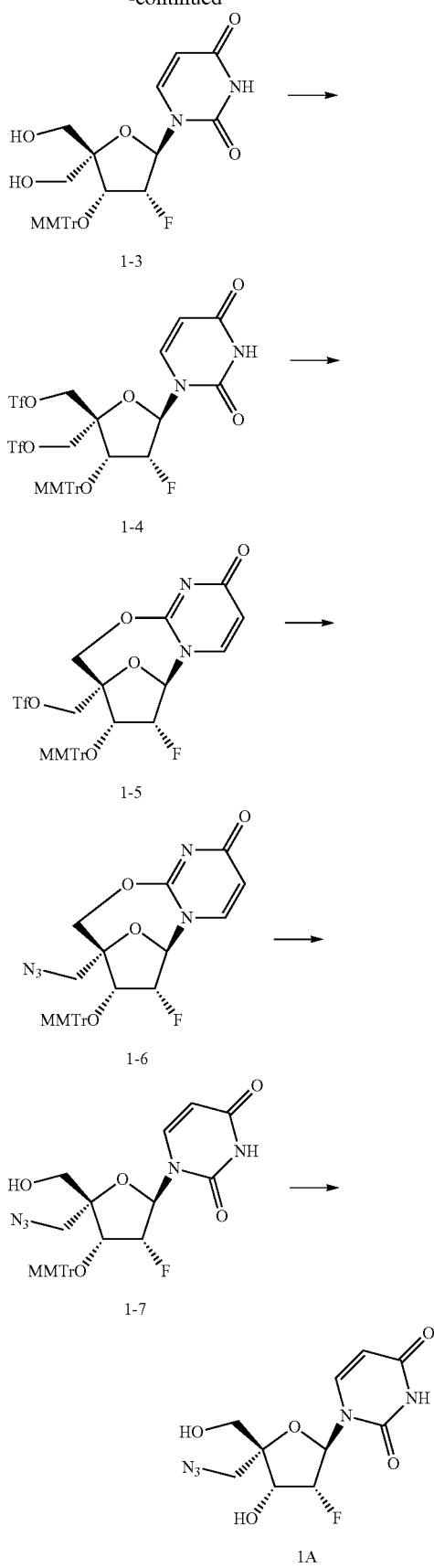

Preparation of (1-2)

To a solution of 1-1 (50 g, 203 mmol) in anhydrous pyridine (200 mL) was added TBDPS-Cl (83.7 g, 304 mmol). The reaction was allowed to proceed overnight at R.T. The solution was concentrated under low pressure to give a residue, which was partitioned between ethyl acetate and water. The organic layer was separated, washed with brine, dried over magnesium sulfate and concentrated under reduced pressure to give 5'-OTBDPS ether as a white foam (94 g).

To a solution of the 5'-OTBDPS ether (94.0 g, 194.2 mmol) in anhydrous DCM (300 mL) were added silver nitrate (66.03 g, 388.4 mmol) and collidine (235 mL, 1.94 mol). The mixture was stirred at R.T. After 15 mins, the mixture was cooled to 0° C., and monomethoxytrityl chloride (239.3 g, 776.8 mmol) was added as a single portion. After being stirred overnight at R.T., the mixture was filtered through Celite and the filtrate was diluted with TBME. The solution was washed successively with 1M citric acid, diluted brine and 5% sodium bicarbonate. The organic solution was dried over sodium sulfate and concentrated under vacuum to give the fully protected intermediate as a yellow foam.

This fully protected intermediate was dissolved in toluene (100 mL) and the solution was concentrated under reduced pressure. The residue was dissolved in anhydrous THF (250 mL) and treated with TBAF (60 g, 233 mmol). The mixture was stirred for 2 h at R.T., and the solvent was removed under reduced pressure. The residue was taken into ethyl acetate and the solution was washed first with saturated sodium bicarbonate and then with brine. After being dried over magnesium sulfate, the solvent was removed in vacuum and the residue was purified by column chromatography (50% EA in PE) to give 1-2 (91 g, 86.4%) as a white foam.

Preparation of (1-3)

To a solution of 1-2 (13.5 g, 26 mmol) in DCM (100 mL) was added pyridine (6.17 mL, 78 mmol). The solution was cooled to 0° C., and Dess-Martin periodinane (33.8 g, 78 mmol) was added as a single portion. The reaction mixture was stirred for 4 h at R.T., and quenched by the addition of $Na_2S_2O_3$ solution (4%) and sodium bicarbonate aqueous solution (4%) (the solution was adjusted to pH 6, ~150 mL). The mixture was stirred for 15 mins. The organic layer was separated, washed with diluted brine and concentrated under reduced pressure. The residue was dissolved in dioxane (100 mL) and the solution was treated with 37% aqueous formaldehyde (21.2 g, 10 eq.) and 2N aqueous sodium hydroxide (10 eq.). The reaction mixture was stirred at R.T., overnight. After stirring for 0.5 h at R.T., the excess of aqueous sodium hydroxide was removed with saturated $NH_4Cl$ (~150 mL). The mixture was concentrated under reduced pressure, and the residue was partitioned between ethyl acetate and 5% sodium bicarbonate. The organic phase was separated, washed with brine, dried over magnesium sulfate and concentrated. The residue was purified by column chromatography (2% MeOH in DCM) to give the diol 1-3 (9.2 g, 83.6%) as a white foam.

Preparation of (1-4)

Compound 1-3 (23 g, 42.0 mmol) was co-evaporated with toluene twice. The residue was dissolved in anhydrous DCM (250 mL) and pyridine (20 mL). The solution was cooled to 0° C., and triflic anhydride (24.9 g, 88.1 mmol) was added dropwise over 10 mins. At this temperature, the reaction was stirred for 40 mins. The reaction was monitored by TLC (PE:EA=2:1 and DCM:MeOH=15:1). After completion, the reaction mixture was quenched with water (50 mL) at 0° C. The mixture was stirred for 30 mins, and extracted with EA. The organic phase was dried over Na₂SO₄ and filtered through a silica gel pad. The filtrate was concentrated under reduced pressure, and the residue was purified by column chromatography (50% EA in PE) to give 1-4 (30.0 g, 88.3%) as a brown foam.

Preparation of (1-5)

To a stirred solution of 1-4 (4.4 g, 5.42 mmol) in anhydrous DMF (50 mL) was added NaH (260 mg, 6.5 mmol) at 0° C. under nitrogen atmosphere. The solution was stirred at R.T., for 1.5 h. The solution was used for the next step without any further workup.

Preparation of (1-6)

To the stirred solution was added NaN₃ (1.5 g, 21.68 mmol) at 0° C. under nitrogen atmosphere, and the resulting solution was stirred at R.T. for 1.5 h. The reaction was quenched with water, extracted with EA, washed with brine, and dried over MgSO₄. The concentrated organic phase was used for the next step without further purification.

Preparation of (1-7)

To a solution of 1-6 (3.0 g, 5.4 mmol) in anhydrous 1,4-dioxane (18 mL) was added NaOH (5.4 mL, 2M in water) at R.T. The reaction mixture was stirred at R.T. for 3 h. The reaction was diluted with EA, washed with brine, and dried over MgSO₄. The concentrated organic phase was purified on a silica gel column (30% EA in PE) to give 1-7 (2.9 g, 93%) as a white foam.

Preparation of (1A)

Compound 1-7 (520 mg, 0.90 mmol) was dissolved in 80% of HCOOH (20 mL) at R.T. The mixture was stirred for 3 h, and monitored by TLC. The solvent was removed and the residue was treated with MeOH and toluene for 3 times. NH₃/MeOH was added, and the reaction mixture was stirred at R.T., for 5 mins. The solvent was concentrated to dryness and the residue was purified by column chromatography to give 1A (120 mg, 44.4%) as a white solid. ESI-LCMS: m/z 302.0 [M+H]⁺, 324.0 [M+Na]⁺.

Example 2

Preparation of Compound 2A

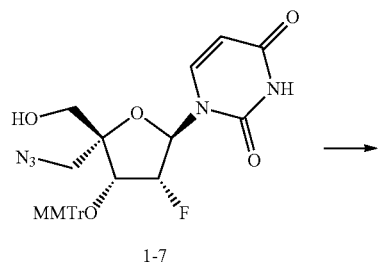

1-7

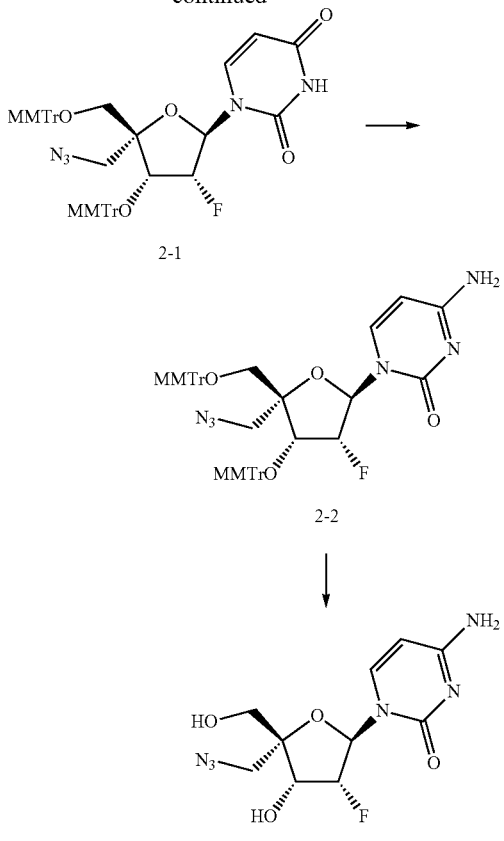

Preparation of (2-1)

To a stirred solution of 1-7 (1.1 g, 2.88 mmol) in anhydrous DCM (10 mL) was added MMTrCl (1.77 g, 5.76 mmol), AgNO₃ (1.47 g, 8.64 mmol) and collidine (1.05 g, 8.64 mmol) at 25° C. under a N₂ atmosphere. The reaction was refluxed for 12 h. MeOH (20 mL) was added and the solvent was removed to dryness. The residue was purified on a silica gel column (20% EA in PE) to give 2-1 (1.6 g, 85.1%) as a white foam.

Preparation of (2-2)

To a stirred solution of 2-1 (800 mg, 0.947 mmol) in anhydrous MeCN (10 mL) were added TPSCl (570 mg, 1.89 mmol), DMAP (230 mg, 1.89 mmol) and TEA (190 mg, 1.89 mmol) at R.T. The mixture was stirred for 12 h. NH₄OH (25 mL) was added and the mixture was stirred for 2 h. The solvent was removed, and the residue was purified on a silica gel column as a yellow foam. Further purification by prep-TLC gave 2-2 (700 mg, 87.1%) as a white solid.

Preparation of (2A)

Compound 2-2 (300 mg, 0.355 mmol) was dissolved in 80% of HCOOH (5 mL) at R.T. The mixture was stirred for 3 h, and monitored by TLC. The solvent was then removed and the residue was treated with MeOH and toluene (3 times). NH₃/MeOH was added and the mixture was stirred at R.T., for 5 mins. The solvent was removed and the residue was purified by column chromatography to give 2A (124 mg, 82.6%) as a white solid. ESI-LCMS: m/z 301.0 [M+H]$^+$, 601.0 [2M+H]$^+$.

Example 3

Preparation of Compound 14A

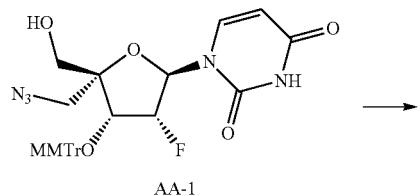
AA-1

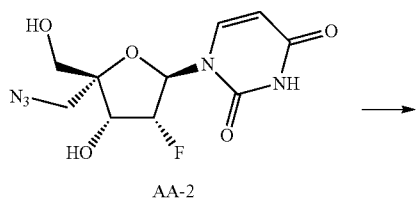
AA-2

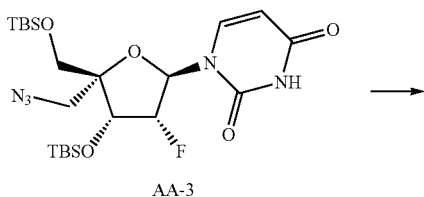
AA-3

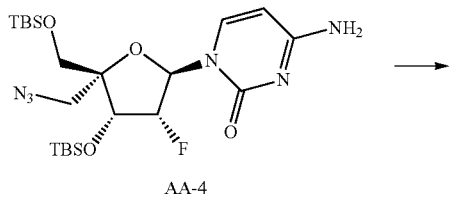
AA-4

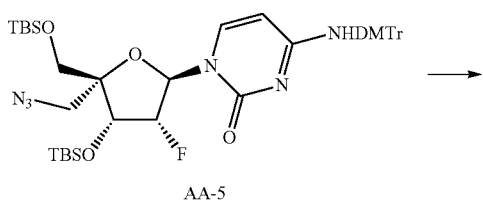
AA-5

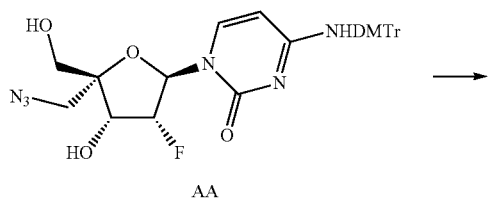
AA

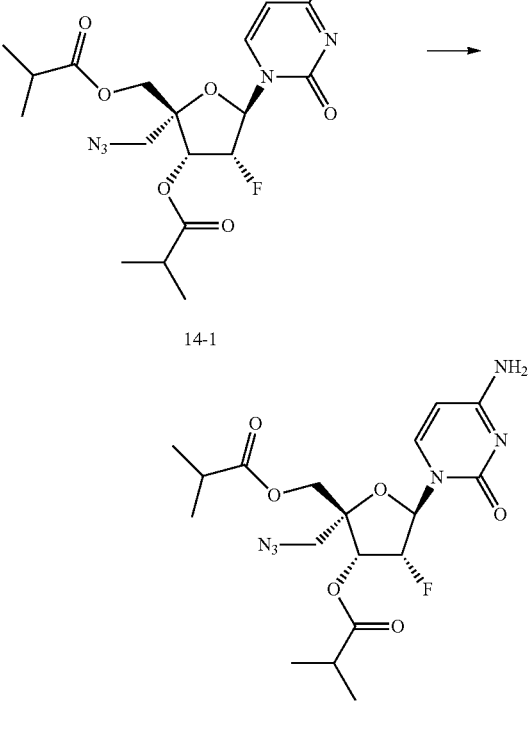
14-1

14A

Preparation of (AA-2)

AA-1 (2.20 g, 3.84 mmol) was dissolved in 80% HCOOH (40 mL) at R.T. (18° C.). The mixture was stirred at R.T. for 12 h. The solvent was removed at low pressure. The residue was purified by column chromatography using 50% EA in Hexane to give AA-2 (1.05 g, 91.3%) as a white solid.

Preparation of (AA-3)

To a stirred solution of AA-2 (1 g, 3.32 mmol) in anhydrous pyridine (20 mL) was added TBSCl (747 mg, 4.98 mmol) and imidazole (451 mg, 6.64 mmol) at R.T. (16° C.) under N$_2$ atmosphere. The mixture was stirred at R.T. for 4 h. The resulting solution was concentrated to dryness under reduced pressure, and the residue was dissolved in EA (100 mL). The solution was washed with sat. NaHCO$_3$ solution and brine, and dried over anhydrous MgSO$_4$. The solution was concentrated to dryness, and the residue was purified on a silica gel column using 20% EA in Hexane to give AA-3 (1.4 g, 79.5%) as a white solid.

Preparation of (AA-4)

To a stirred solution of AA-3 (1.50 g, 2.83 mmol, 1.00 eq.) in anhydrous CH$_3$CN (28 mL) was added TPSCl (1.71 g, 5.80 mmol, 2.05 eq.), DMAP (691.70 mg, 5.66 mmol, 2.00 eq.) and TEA (573.00 mg, 5.66 mmol, 2.00 eq.) at R.T. (15° C.). The mixture was stirred for 2 h. NH$_3$.H$_2$O (20 mL) was added, and the mixture was stirred for 3 h. The mixture was extracted with EA (3×60 mL). The organic phase was washed with brine, dried over anhydrous Na$_2$SO$_4$ and concentrated at low pressure. The residue was purified on a silica gel column (30% EA in PE) to give AA-4 (2.3 g, crude) as a yellow foam.

Preparation of (AA-5)

To a stirred solution of AA-4 (1.90 g, 2.34 mmol) in anhydrous DCM (20 mL) was added DMTrCl (1.82 g, 3.49 mmol) and 2,4,6-trimethylpyridine (1.00 g, 8.25 mmol) at R.T. (15° C.) under $N_2$ atmosphere. The mixture was stirred at R.T. for 12 h. MeOH (20 mL) was added. The mixture was filtered, and the filtrate was concentrated to dryness. The residue was dissolved in EA (80 mL). The solution was washed with brine, dried over anhydrous $Na_2SO_4$ and concentrated at low pressure. The residue was purified on a silica gel column (5% MeOH in DCM) to give AA-5 (1.4 g, crude) as a white solid.

Preparation of (AA)

AA-5 (2.40 g, 2.60 mmol) was dissolved in TBAF (10 mL, 1M in THF). The mixture was stirred at R.T. (15° C.) for 30 mins. The mixture was concentrated to dryness, and the residue was dissolved in EA (60 mL). The solution was washed with brine, dried over $MgSO_4$ and concentrated under reduced pressure. The residue was purified on a silica gel column (5% MeOH in DCM) to give AA (1.50 g, 95.8%) as a white solid. ESI-MS: m/z 625.3 [M+Na]$^+$.

Preparation of (14-1)

To a solution of AA (60.0 mg, 99.57 μmol, 1.00 eq.) in pyridine (1 mL) was added isobutyric anhydride (31.50 mg, 199.13 μmol, 2.00 eq.) in 1 portion at R.T. (15° C.) under $N_2$ atmosphere. The mixture was stirred at R.T. for 12 h. The mixture was concentrated, and the residue was partitioned between EA and water. The combined organic phases were washed with water and brine, and dried over anhydrous $Na_2SO_4$. The mixture was filtered, and the filtrate was concentrated to dryness. The residue was purified by silica gel chromatography (30% EA in PE) to afford 14-1 (59.00 mg, 79.77%) as a white solid.

Preparation of (14A)

14-1 (57.00 mg, 76.74 μmol, 1.00 eq.) was dissolved in 80% $CH_3COOH$ (8 mL). The solution was stirred at R.T. (15° C.) for 12 h. The mixture was concentrated to dryness. The residue was purified on a silica gel column (2.5% MeOH in DCM) to give 14A (23.00 mg, 68.05%) as a white foam. ESI-MS: m/z 441.2 [M+H]$^+$, 463.2 [M+Na]$^+$.

Example 4

Preparation of Compound 15A

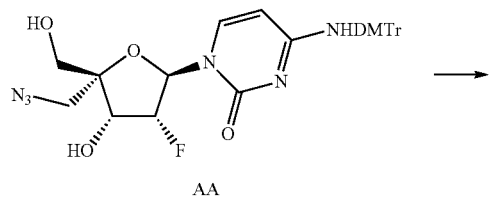

AA

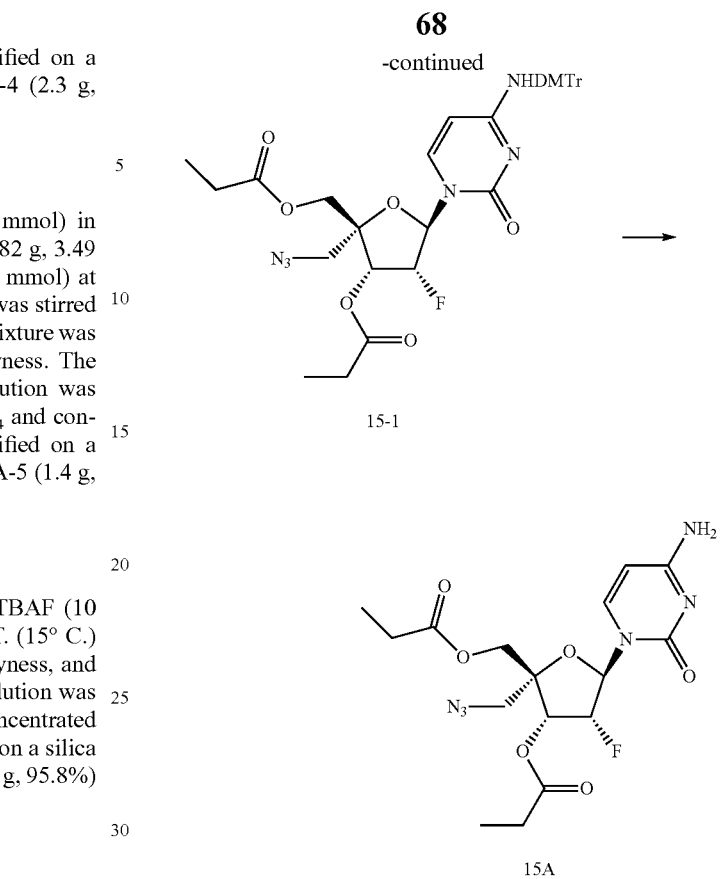

15-1

15A

Preparation of (15-1)

15-1 was prepared in similar manner as 14-1 using AA (60.00 mg, 99.57 μmol, 1.00 eq.) in pyridine (1 mL) and propionic anhydride (25.92 mg, 199.13 mmol, 2.00 eq.). 15-1 (white solid, 56.00 mg, 78.69%).

Preparation of (15A)

Compound 15A was prepared in similar manner as 14A using 15-1 (54.00 mg, 75.55 mmol, 1.00 eq.) 15A (white foam, 18.00 mg, 57.78%). ESI-MS: m/z 413.1 [M+H]$^+$.

Example 5

Preparation of Compound 16A

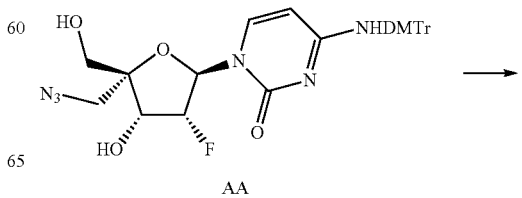

AA

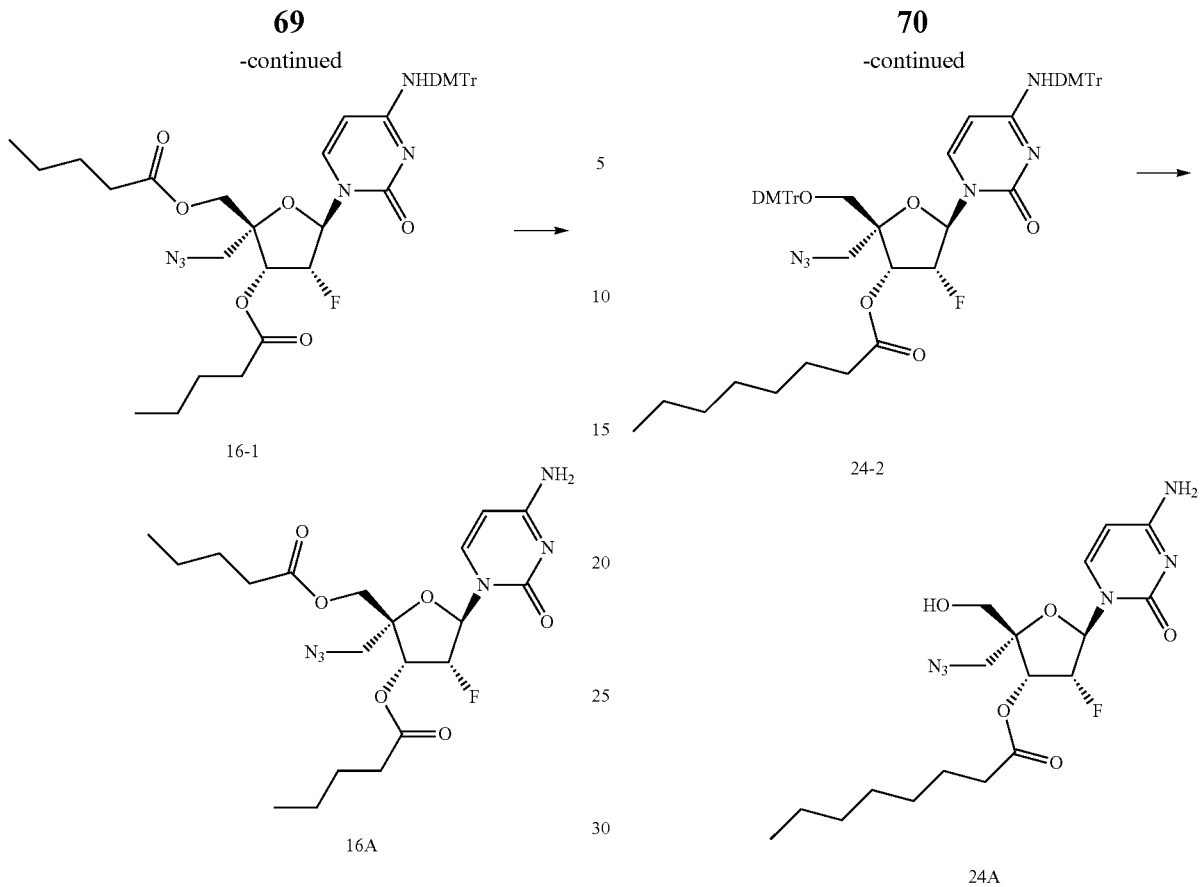

16-1

16A

Preparation of (16-1)

16-1 was prepared in similar manner as 14-1 using AA (62.00 mg, 102.89 μmol, 1.00 eq.) in pyridine (1 mL) and pentanoic anhydride (38.32 mg, 205.77 mmol, 2.00 eq.). 16-1 (white solid, 60.00 mg, 75.65%).

Preparation of (16A)

Compound 16A was prepared in similar manner as 14A using 16-1 (75.00 mg, 97.30 mmol, 1.00 eq.) 16A (white foam, 28.00 mg, 61.43%). ESI-MS: m/z 469.2 [M+H]$^+$.

Example 6

Preparation of Compound 24A

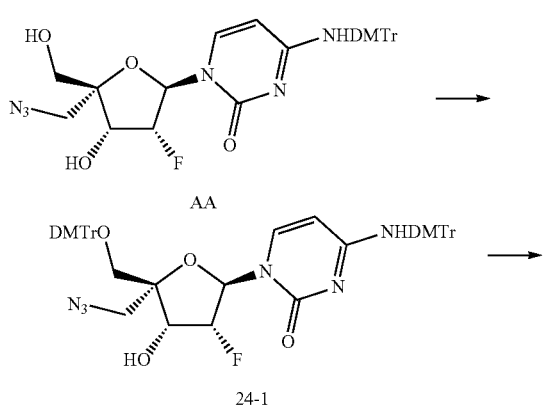

24-2

24A

Preparation of (24-1)

To a stirred solution of AA-1 (300.0 mg, 497.83 μmol) in anhydrous pyridine (0.5 mL) was added DMTrCl (337.36 mg, 995.66 μmol) at R.T. (17° C.) under $N_2$ atmosphere. The solution was stirred at 50° C.~60° C. for 12 h. The mixture was concentrated to dryness under reduced pressure, and the residue was dissolved in EA (40 mL). The solution was washed with brine, dried over anhydrous $MgSO_4$, and concentrated to dryness at low pressure. The residue was purified on a silica gel column using 20% EA in PE to give 24-1 (300 mg, 66.59%) as a white solid.

Preparation of (24-2)

To a stirred solution of 24-1 (100.00 mg, 110.50 μmol) in anhydrous pyridine (0.5 mL) was added DMAP (6.75 mg, 55.25 μmol), DCC (22.80 mg, 110.50 μmol) and n-actanoic acid (31.87 mg, 221.00 μmol) at R.T. (18° C.) under $N_2$ atmosphere. The solution was stirred at R.T. for 12 h. The solution was concentrated to dryness under reduced pressure. The residue was purified on a silica gel column using 15% EA in PE to give 24-2 (98.00 mg, 86.0%) as a white foam.

Preparation of (24A)

24-2 (90.00 mg, 87.28 μmol) was dissolved in 80% $CH_3COOH$ (20 mL) at R.T. (16° C.). The mixture was stirred R.T. for 12 h. The reaction was quenched with MeOH, and the mixture was concentrated to dryness. The residue was purified on a silica gel column (5% MeOH in DCM) to give 24A (33.00 mg, 88.7%) as a white solid. ESI-MS: m/z 427.2 [M+H]$^+$.

Example 7

Preparation of Compound 25A

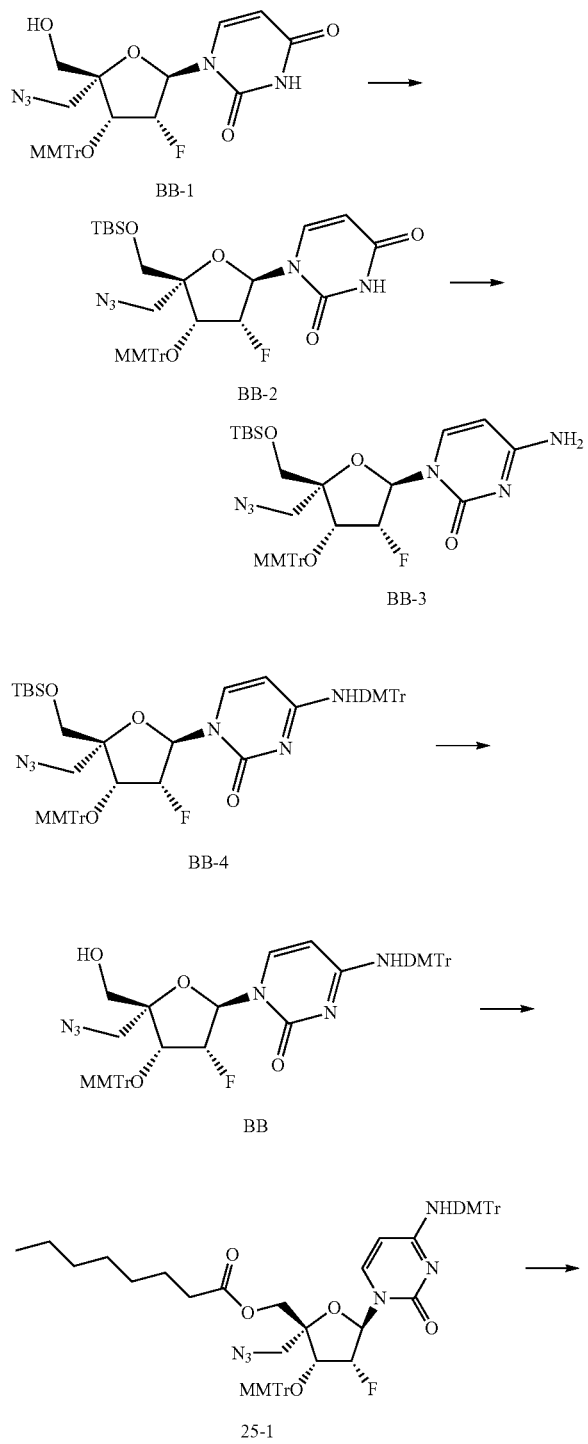

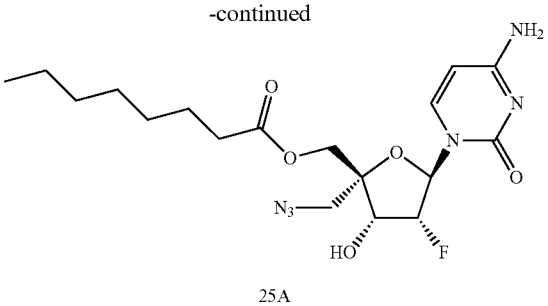

Preparation of (BB-2)

To a stirred solution of BB-1 (500.00 mg, 0.87 mmol) in anhydrous pyridine (1 mL) was added TBSCl (236.5 mg, 1.57 mmol) at 20° C. under N$_2$. The solution was stirred at 50° C.~60° C. for 12 h. The solution was concentrated to dryness under reduced pressure. The residue was dissolved in EA (50 mL). The solution was washed with sat. NaHCO$_3$ solution and brine, and dried over anhydrous MgSO$_4$. The solution was filtered, and the filtrate was concentrated to dryness. The residue was purified on a silica gel column to give BB-2 (510.00 mg, 85.06%) as a white solid.

Preparation of (BB-3)

To a stirred solution of BB-2 (430.00 mg, 625.15 mmol) in anhydrous MeCN (6 mL) was added TPSCl (368.65 mg, 1.25 mmol), DMAP (152.75 mg, 1.25 mmol) and TEA (126.52 mg, 1.25 mmol) at R.T. The mixture was stirred for 2 h. NH$_4$OH (8 mL) was added, and the mixture stirred for 3 h. The mixture was extracted with EA (3×40 mL). The organic phase was washed with brine, dried over anhydrous Na$_2$SO$_4$ and concentrated at low pressure. The residue was purified on a silica gel column (25% EA in PE) to give BB-3 (500 mg of crude) as a yellow foam.

Preparation of (BB-4)

To a stirred solution of BB-3 (500 mg of crude, 0.72 mmol) in anhydrous DCM (7 mL) was added DMTrCl (365 mg, 1.0 mmol) and collidine (305 mg, 2.5 mmol) and AgNO$_3$ (184 mg, 1.08 mmol) at R.T. (15° C.) under N$_2$ atmosphere. The mixture was stirred at R.T. for 12 h. MeOH (5 mL) was added. The mixture was filtered, and the filtrate was concentrated to dryness. The residue was dissolved in EA (50 mL). The solution was washed with brine, dried over anhydrous Na$_2$SO$_4$ and concentrated at low pressure. The residue was purified on a silica gel column (5% MeOH in DCM) to give BB-4 (500 mg, 70.3%) as a white solid.

Preparation of (BB)

BB-4 (1.00 g, 1.01 mmol) was dissolved in TBAF (5 mL, 1M in THF) and stirred at R.T. for 30 mins. The mixture was diluted with EA (100 mL). The mixture was washed with water and brine, and dried over anhydrous MgSO$_4$. The organic phase was concentrated to dryness. The residue was purified on the silica gel column (30% EA in PE) to give BB (0.80 g, 91.5%) as a white solid. ESI-MS: m/z 873.7 [M+1]$^+$.

Preparation of (25-1)

To a solution of BB (100.00 mg, 114.29 µmol) in anhydrous pyridine (1.5 mL) was added DMAP (2.79 mg, 22.86

μmol), DCC (70.75 mg, 342.88 mmol) and n-octanoic acid (49.45 mg, 342.88 μmol) at R.T. (18° C.) under N$_2$ atmosphere. The solution was stirred at R.T. for 12 h. The solution was concentrated to dryness under reduced pressure. The residue was purified on a silica gel column using 15% EA in PE to give 25-1 (95.00 mg, 83.03%) as a white foam.

Preparation of (25A)

25-1 (110.00 mg, 109.87 μmol) was dissolved in 80% CH$_3$COOH (25 mL) at R.T. (15° C.). The mixture was stirred for 12 h. The reaction was quenched with MeOH, and the solution was concentrated to dryness. The residue was purified on a silica gel column (5% MeOH in DCM) to give 25A (30.00 mg, 64.03%) as a white solid. ESI-MS: m/z 427.2 [M+H]$^+$.

Example 8

Preparation of Compound 26A

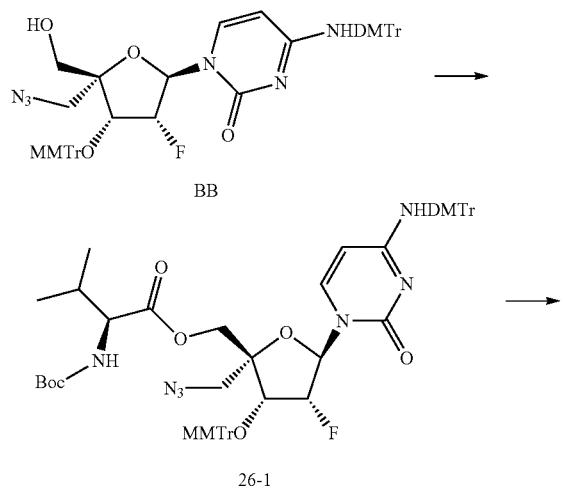

Preparation of (26-1)

To a solution of N-Boc-L-Valine (620.78 mg, 2.86 mmol) and TEA (144.57 mg, 1.43 mmol) in anhydrous THF (2.5 mL) was added BB (250.00 mg, 285.73 μmol). The mixture was co-evaporated with pyridine and toluene to remove water. The residue was dissolved in THF (2.5 mL). DIPEA (369.28 mg, 2.86 mmol) was added, followed by addition of BOP-Cl (363.68 mg, 1.43 mmol) and 3-nitro-1H-1,2,4-triazole (162.95 mg, 1.43 mmol) at R.T. (18° C.). The mixture was stirred at R.T. for 12 h and then diluted with EA (40 mL). The solution was washed with brine, dried over anhydrous Na$_2$SO$_4$ and concentrated to dryness at low pressure. The residue was purified on a silica gel column (30% EA in PE) to give 26-1 (220 mg, crude) as a white foam.

Preparation of (26-2)

26-1 (250.0 mg, 232.73 μmol) was dissolved in 80% CH$_3$COOH (30 mL). The solution was heated to 50° C. and stirred for 12 h. The reaction was quenched with MeOH, and the solution was concentrated to dryness. The residue was purified on a silica gel column (5% MeOH in DCM) to give 26-2 (80.00 mg, 68.82%) as a white foam.

Preparation of (26A)

26-2 (78.00 mg, 156.16 μmol) was dissolved in HCl/dioxane (1.5 mL) and EA (1.5 mL) at R.T. (19° C.). The mixture was stirred at R.T. for 30 mins. The solution was concentrated to dryness at low pressure The residue was purified by prep-HPLC to give 26A (23 mg, 31.25%) as a white solid. ESI-MS: m/z 400.20 [M+H]$^+$, 799.36 [2M+H]$^+$.

Example 9

Preparation of Compound 27A

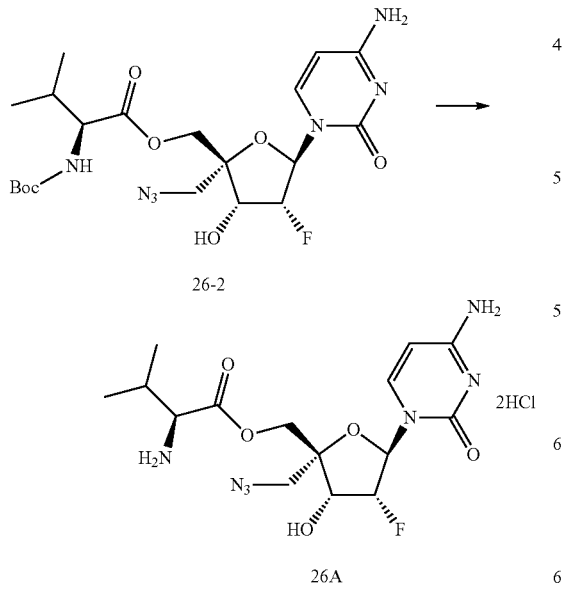

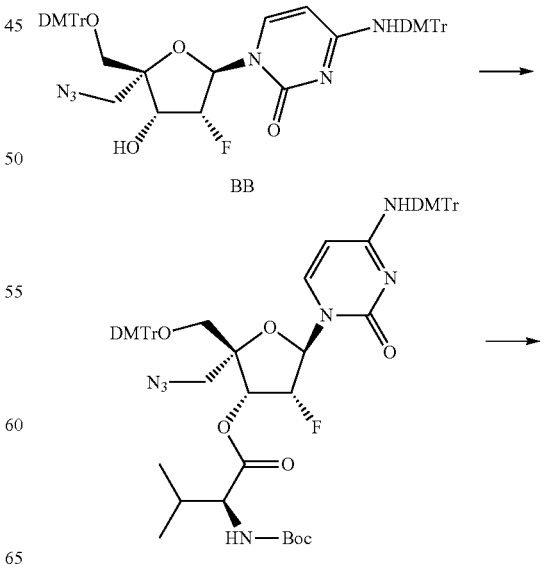

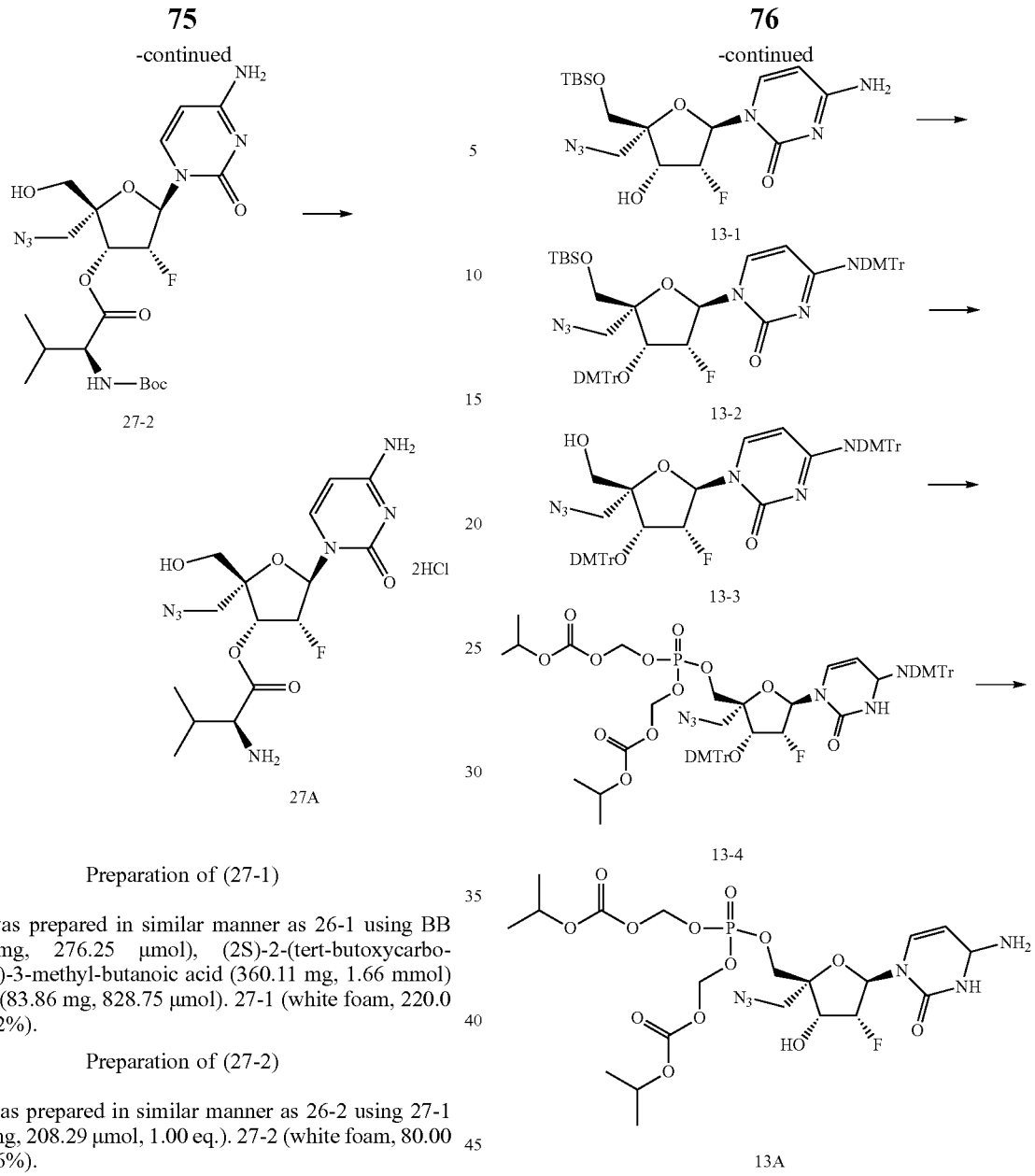

Preparation of (27-1)

27-1 was prepared in similar manner as 26-1 using BB (250.0 mg, 276.25 µmol), (2S)-2-(tert-butoxycarbonylamino)-3-methyl-butanoic acid (360.11 mg, 1.66 mmol) and TEA (83.86 mg, 828.75 µmol). 27-1 (white foam, 220.0 mg, 72.12%).

Preparation of (27-2)

27-2 was prepared in similar manner as 26-2 using 27-1 (230.00 mg, 208.29 µmol, 1.00 eq.). 27-2 (white foam, 80.00 mg, 77.66%).

Preparation of (27A)

27A was prepared in similar manner as 26 using 27-2 (100.00 mg, 200.20 µmol, 1.00 eq.). 27A (white solid, 56 mg, 59.57%). ESI-MS: m/z 400.0 [M+H]$^+$, 422.1 [M+Na]$^+$; 799.1 [2M+H]$^+$, 821.2 [2M+Na]$^+$.

Example 10

Preparation of Compound 13A

Preparation of (13-1)

To a solution of 2A (200 mg, 0.67 mmol) in anhydrous pyridine (5 mL) was added TBSCl (120 mg, 0.8 mmol) at R.T. The mixture was stirred overnight, and the reaction mixture was diluted with EA. The mixture was washed with NaHCO$_3$ aq. solution and brine. The organic layer was dried, filtered and concentrated to give residue, which was purified by silica gel column chromatography (5% MeOH in DCM to 25% MeOH in DCM to give 13-1 (153 mg, 55%) as a white solid.

Preparation of (13-2)

To a solution of 13-1 (54 mg, 0.13 mmol) in anhydrous DCM (2 mL) was added collidine (95 µL, 0.78 mmol), DMTrCl (262 mg, 0.78 mmol) and AgNO$_3$ (66 mg, 0.39 mmol) at R.T. The mixture was stirred overnight, and then diluted with DCM (5 mL). The mixture was filtered through a pre-packed celite funnel, and the filtrate was washed with NaHCO₃ aq. solution, 1.0 M citric acid solution and then brine. The organic layer was dried over Na₂SO₄, and concentrated at low pressure to give a residue. The residue was purified by silica gel column chromatography (25% EA in PE to 100% EA) to give 13-2 (83.5 mg, 63.6%).

Preparation of (13-3)

To a solution of 13-2 (83 mg, 0.081 mmol) in THF (1 mL), was added a 1M solution of TBAF in THF (0.122 mL, 0.122 mmol) at ice bath temperature. The mixture was stirred for 1.5 h. The mixture was diluted with EA, and washed with water and brine. The organic layer was dried and concentrated to give the crude product, which was purified by silica gel column chromatography (DCM to 5% MeOH in DCM) to give 13-3 (66.6 mg, 91%) as a white foam.

Preparation of (13-4)

13-3 (66.6 mg, 0.074 mmol) was co-evaporated with toluene and THF (3×). Bis(POC)phosphate (33 mg, 0.96 mmol) was added, and then co-evaporated with toluene (3×). The mixture was dissolved in anhydrous THF (1.5 mL) and cooled in an ice bath (0 to 5° C.). 3-nitro-1,2,4-triazole (13 mg, 0.11 mmol), diisopropylethyl amine (54 µL, 0.3 mmol), and BOP-Cl (28 mg, 0.11 mmol) were added successively. The mixture was stirred 2 h at 0 to 5° C., diluted with EtOAc, washed with 1.0M citric acid, sat. aq. NaHCO₃ and brine, and dried with Na₂SO₄. The residue was purified on silica (10 g column) with CH₂Cl₂:i-PrOH (4-10% gradient) to give 13-4 (68 mg, 76%) as a white solid.

Preparation of (13A)

13-4 (68 mg, 0.07 mmol) was dissolved in 80% HCOOH. The mixture was stirred at R.T. for 2 h. The solvents were evaporated at R.T. and co-evaporated with toluene (3×). The residue was dissolved in 50% CH₃CN/H₂O, was purified on a reverse-phase HPLC (C18) using CH₃CN and H₂O. The product was lyophilization to give 13A (4.8 mg, 14%) as a white foam. ESI-LCMS: m/z=613.1 [M+H]⁺, 1225.2 [2M+H]⁺.

Example 11

Preparation of Compound 17A

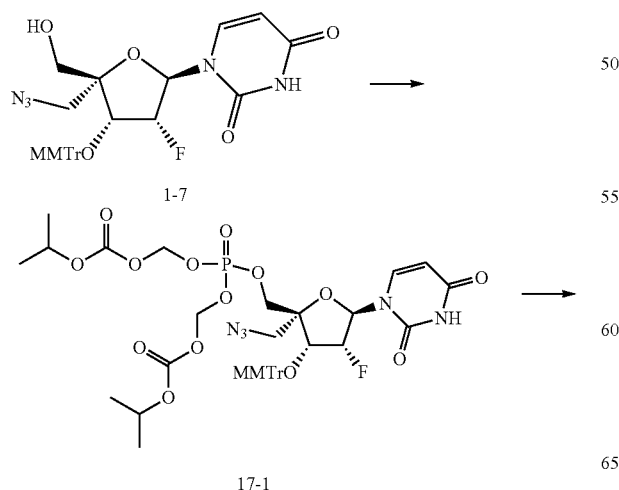

17-1

-continued

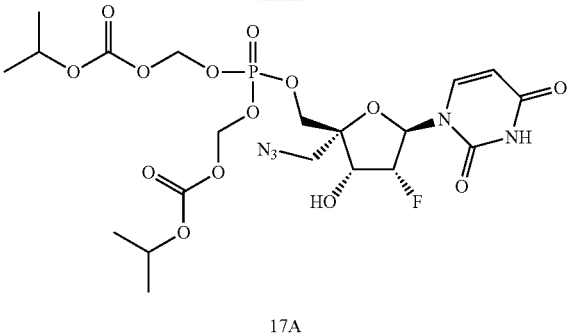

17A

Preparation of (17-1)

17-1 (40.7 mg, 53%) was prepared in the same manner from 1-7 (50 mg, 0.087 mmol) and bis(isopropyloxycarbonyloxymethyl)phosphate (58 mg, 0.175 mmol) with DIPEA (75 µL, 0.52 mmol), BOP-Cl (66.2 mg, 0.26 mmol), and 3-nitro-1,2,4-triazole (30 mg, 0.26 mmol) in THF (0.4 mL) in a similar manner as 13-4.

Preparation of (17A)

17-1 (40 mg, 0.045 mmol) was dissolved in anhydrous CH₃CN (0.5 mL), and 4N HCl in dioxane (34 µL, 0.135 mmol) was added at 0 to 5° C. The mixture was stirred at R.T. for 3 h. Anhydrous EtOH (200 µL) was added. The solvents were evaporated at R.T. and co-evaporated with toluene (3×). The residue was purified on silica (10 g column) with MeOH/CH₂Cl₂ (5-7% gradient) and lypholized give 17A (15.4 mg, 76%) as a white foam. ESI-LCMS: m/z=614.15 [M+H]⁺, 1227.2 [2M+H]⁺.

Example 12

Preparation of Compound 18A

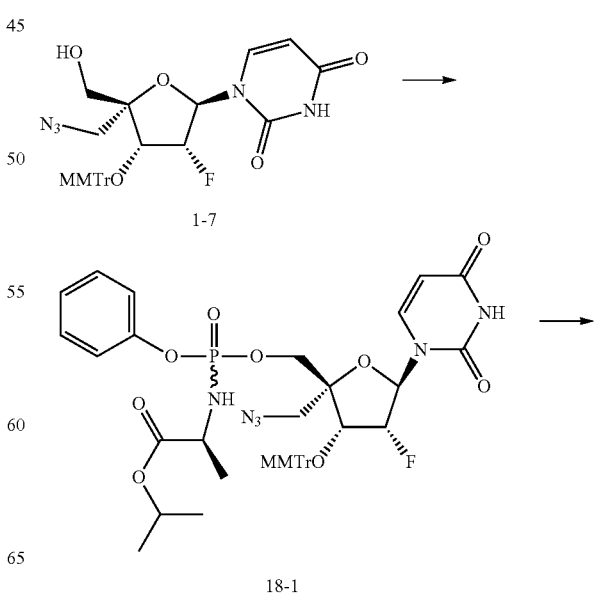

1-7

18-1

-continued

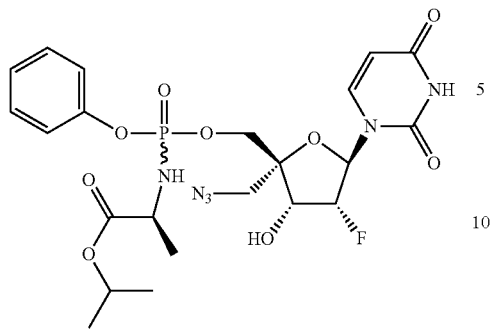

18A

Preparation of (18-1)

To a stirred solution of 1-7 (80 mg, 0.14 mmol) in anhydrous CH₃CN (2.0 mL) was added N-methylimidazole (0.092 mL, 1.12 mmol) at 0° C. (ice/water bath). A solution of phenyl (isopropoxy-L-alaninyl) phosphorochloridate (128 mg, 0.42 mmol, dissolved in CH₃CN (0.5 mL)) was then added (prepared according to a general procedure as described in McGuigan et al., *J. Med. Chem.* (2008) 51:5807-5812). The solution was stirred at 0 to 5° C. for h and then stirred at R.T. for 16 h. The mixture was cooled to 0 to 5° C., diluted with EA followed by the addition of water (5 mL). The solution was washed with 1.0M citric acid, sat. aq. NaHCO₃ and brine, and dried with MgSO₄. The residue was purified on silica (10 g column) with EA/hexanes (25-100% gradient) to give 18-1 (57.3 mg, 49%) as a foam.

Preparation of (18A)

18-1 (57.3 mg, 0.07 mmol) was dissolved in anhydrous CH₃CN (0.5 mL), and 4N HCl in dioxane (68 μL, 0.27 mmol) was added at 0 to 5° C. The mixture was stirred at R.T. for 2 h, and anhydrous EtOH (100 μL) was added. The solvents were evaporated at R.T. and co-evaporated with toluene (3×). The residue was purified on silica (10 g column) with MeOH/CH₂Cl₂ (1-7% gradient) and lypholized to give 18A (27.8 mg, 72%) as a white foam. ESI-LCMS: m/z=571.1 [M+H]⁺, 1141.2 [2M+H]⁺.

Example 13

Preparation of Compound 28A

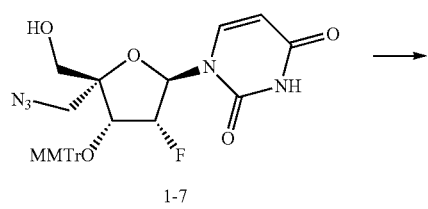

1-7

-continued

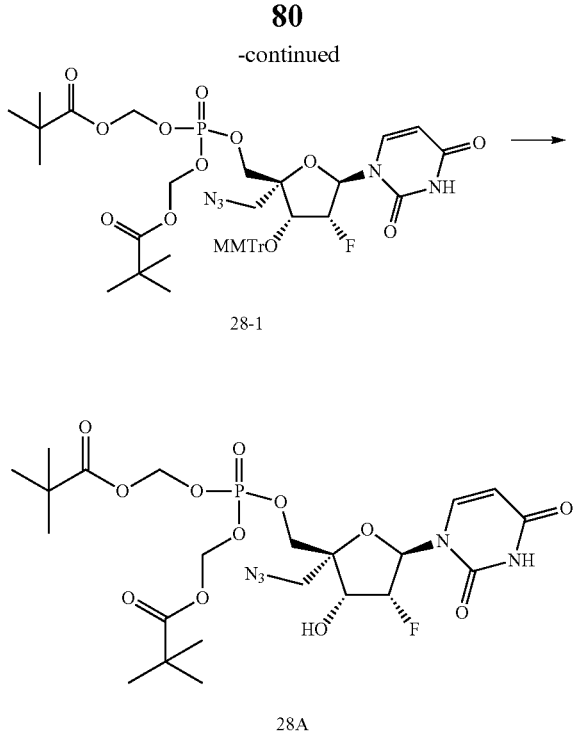

Preparation of (28-1)

28-1 (68.4 mg, 44.7%) was prepared from 1-7 (100 mg, 0.174 mmol) and bis(tert-butoxycarbonyloxymethyl)phosphate (126 mg, 0.35 mmol) with DIPEA (192 μL, 1.04 mmol), BOP-Cl (133 mg, 0.52 mmol), and 3-nitro-1,2,4-triazole (59 mg, 0.52 mmol) in THF (1.5 mL) in the same manner as 13-4.

Preparation of (28A)

28A (31.4 mg, 67%) was prepared from 28-1 (68 mg, 0.077 mmol) in the same manner as 17A. ESI-LCMS: m/z=627.15 [M+Na]⁺, 1219.25 [2M+H]⁺.

Example 14

Preparation of Compound 19A

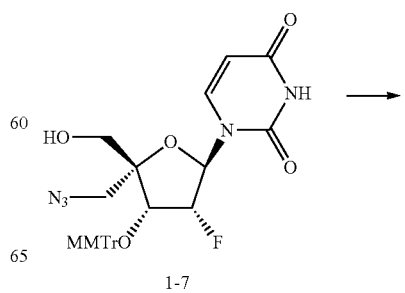

1-7

-continued

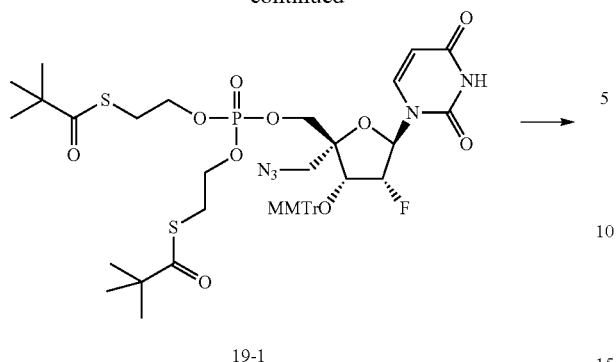

19-1

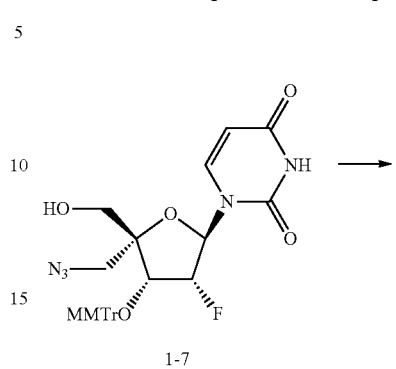

19A

Preparation of (19-1)

To a solution of 1-7 (100 mg, 0.175 mmol) in anhydrous CH$_3$CN (2 mL) was added 5-ethylthio-1H-tetrazole in CH$_3$CN (0.25M; 0.84 mL, 0.21 mmol). Bis-SATE-phosphoramidate (95 mg, 0.21 mmol) in CH$_3$CN (1 mL) was added at 0 to 5° C. dropwise. The mixture was stirred 2 h at 0 to 5° C. under Ar. A solution of 77% m-CPBA (78 mg, 0.35 mmol) in DCM (1 mL) was added, and the mixture stirred 2 h at 0 to 5° C. under Ar. The mixture was diluted with EtOAc (50 mL), washed with 1.0M citric acid, sat. NaHCO$_3$ and brine, and dried with MgSO$_4$. The mixture was filtered, and the solvents were evaporated in vacuo. The residue was purified on silica (10 g column) with EA/hexanes (20-100% gradient) to give 19-1 (105 mg, 63.6%) as a white foam.

Preparation of (19A)

19-1 (105 mg, 0.112 mmol) was dissolved in anhydrous CH$_3$CN (0.8 mL), and 4N HCl in dioxane (84 µL, 0.334 mmol) was added at 0 to 5° C. The mixture was stirred at R.T. for 2 h. Anhydrous EtOH (100 µL) was added. The solvents were evaporated at R.T., and co-evaporated with toluene (3×). The residue was purified on silica (10 g column) with MeOH/CH$_2$Cl$_2$ (1-7% gradient) and lypholized to give 19A (42.7 mg, 57%) as a white foam ESI-LCMS: m/z=692.15 [M+Na]$^+$, 1339.30 [2M+H]$^+$.

Example 15

Preparation of Compound 20A

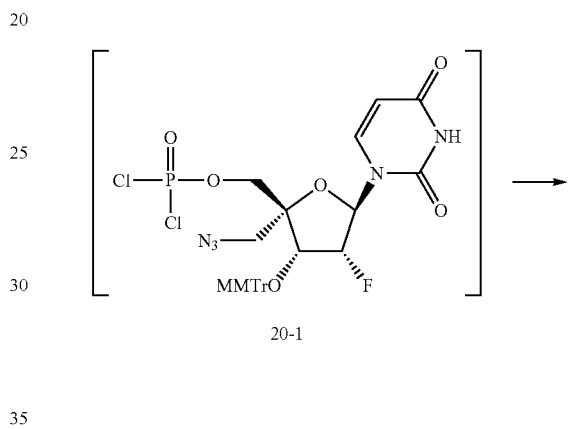

1-7

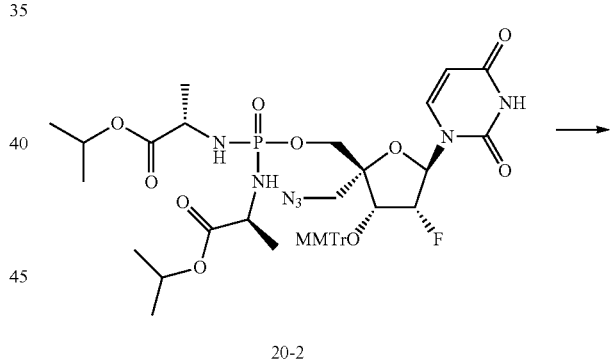

20-1

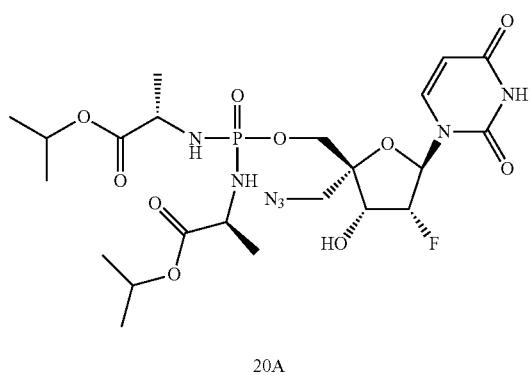

20-2

[Structure of 20A]

20A

Preparation of (20-2)

1-7 (100 mg, 0.174 mmol) was co-evaporated with anhydrous pyridine (3×), toluene (3×) and CH$_3$CN (3×), and dried under high vacuum overnight. 1-7 was dissolved in CH$_3$CN (2 mL). A proton sponge (112 mg, 0.52 mmol), POCl$_3$ (49 uL, 0.52 mmol) were added at 0 to 5° C. The mixture was stirred for 3 h at 0 to 5° C. to give intermediate 20-1. To this solution, L-alanine isopropyl ester hydrochloride (146 mg, 0.87 mmol), and TEA (114 uL, 1.74 mmol) were added. The mixture was stirred for 4 h at 0 to 5° C. The mixture was stirred 2 h at 0 to 5° C., then diluted with EtOAc. The mixture was washed with 1.0M citric acid, sat. aq. NaHCO$_3$ and brine, and dried with Na$_2$SO$_4$. The residue was purified on silica (10 g column) with CH$_2$Cl$_2$/MeOH (0-7% gradient) to give 20-2 (67 mg, 43.7%) as a white solid.

Preparation of (20A)

20-2 (65 mg, 0.074 mmol) was dissolved in anhydrous CH$_3$CN (0.5 mL), and 4N HCl in dioxane (55 μL, 0.22 mmol) was added at 0 to 5° C. The mixture was stirred at R.T. for 1.5 h. A second portion of 4N HCl in dioxane (15 μL) was added, and the mixture stirred at R.T. for 2 h. Anhydrous EtOH (300 μL) was added. The solvents were evaporated at R.T. and co-evaporated with toluene (3×). The residue was dissolved in 50% CH$_3$CN/H$_2$O, was purified on a reverse-phase HPLC (C18) with CH$_3$CN and water, and lyophilized to give 20A (9 mg, 20%) as a white foam. ESI-LCMS: m/z=608.15 [M+H]$^+$, 1215.3 [2M+H]$^+$.

Example 16

Preparation of Compound 23A

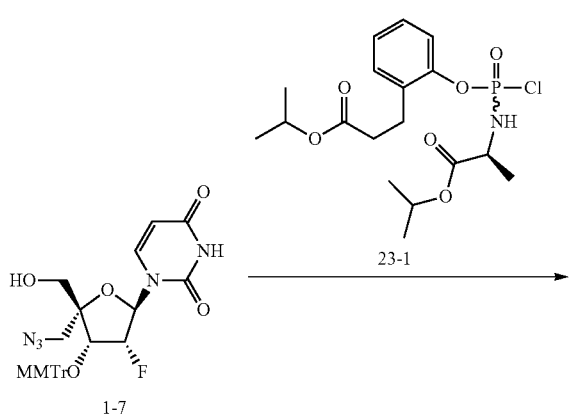

1-7

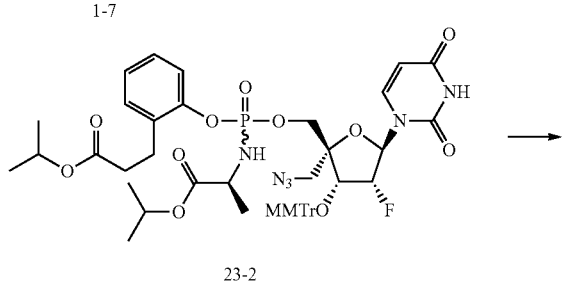

23-2

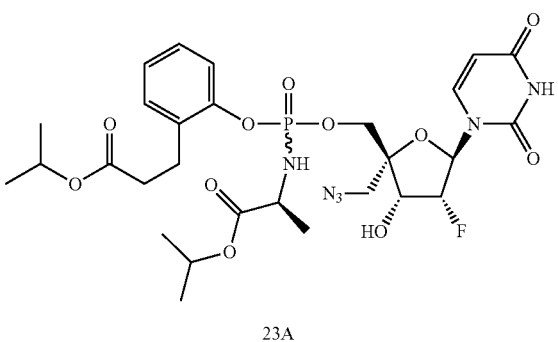

23A

Preparation of (23-2)

To a stirred solution of 1-7 (100 mg, 0.175 mmol) in anhydrous CH$_3$CN (2.0 mL) was added N-methylimidazole (0.14 mL, 1.4 mmol) at 0° C. (ice/water bath). A solution of 23-1 (220 mg, 0.53 mmol, dissolved in 0.5 mL of CH$_3$CN), (prepared according to a general procedure described in Bondada, L. et al., *ACS Medicinal Chemistry Letters*, (2013) 4(8):747-751) was added. The solution was stirred at 0 to 5° C. for 1 h and then stirred at R.T. for 16 h. The mixture was cooled to 0 to 5° C., diluted with EA followed by addition of water (5 mL). The solution was washed with 1.0M citric acid, sat. aq. NaHCO$_3$ and brine, and dried with MgSO$_4$. The residue was purified on silica (10 g column) with EA/hexanes (25-100% gradient) to give 23-2 (56.4 mg, 33.7%) as a white foam.

Preparation of (23A)

23-2 (56 mg, 0.0585 mmol) was dissolved in anhydrous CH$_3$CN (0.7 mL), and 4N HCl in dioxane (44 μL, 0.176 mmol) was added at 0 to 5° C. The mixture was stirred at R.T. for 2 h. 4N HCl in dioxane (20 μL) was added. The mixture was stirred at R.T. for 2 h. Anhydrous EtOH (100 μL) was added. The solvents were evaporated at R.T. and co-evaporated with toluene (3×). The residue was purified on silica (10 g column) with MeOH/CH$_2$Cl$_2$ (1-7% gradient) and lypholized to give 23A (27.6 mg, 69%) as a white foam. ESI-LCMS: m/z=685.2 [M+H]$^+$.

Example 17

Preparation of Compound 29A

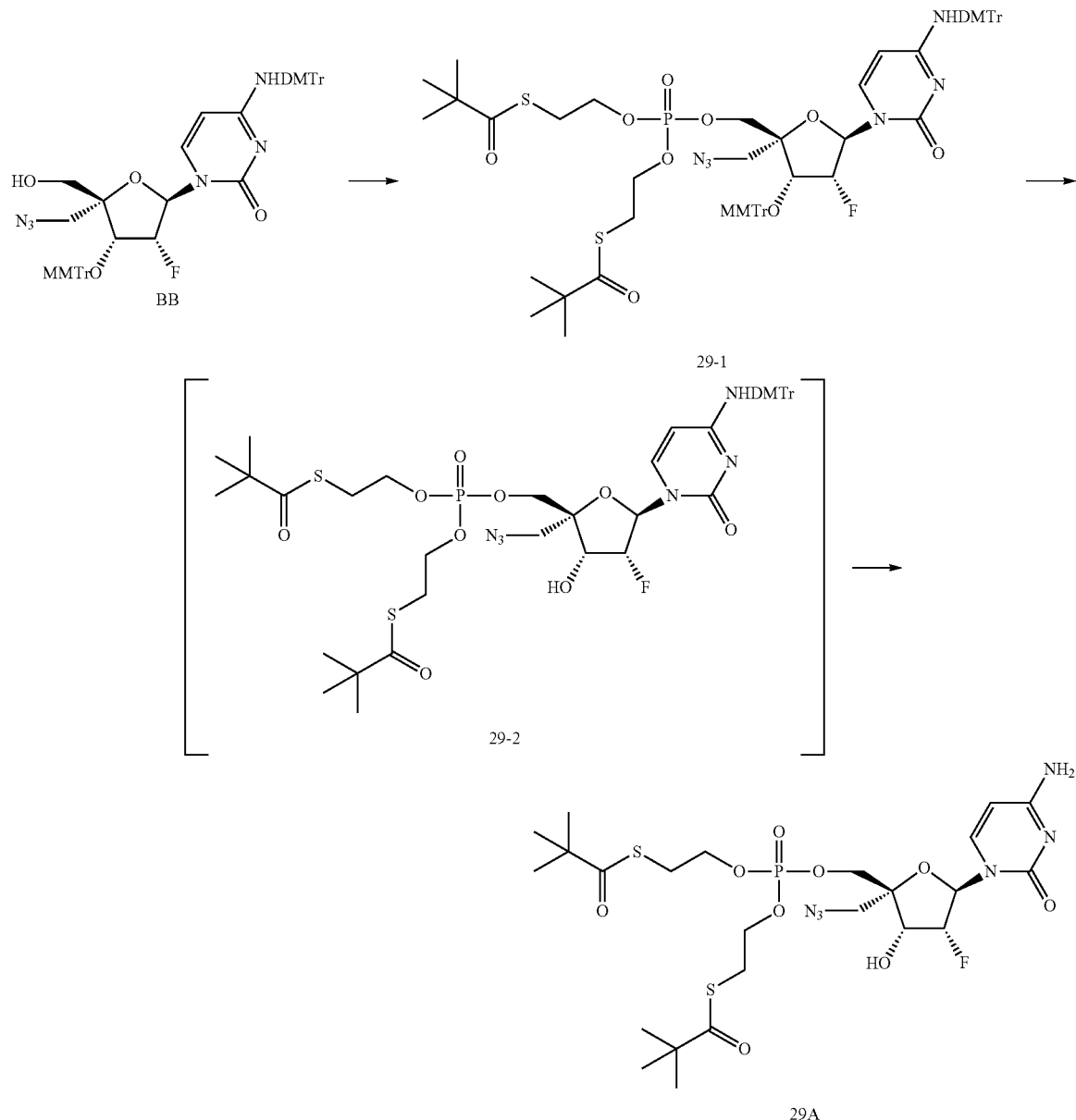

Preparation of (29-1)

To a solution of BB (100 mg, 0.114 mmol) in anhydrous CH$_3$CN (2 mL) were added a solution of bis-SATE-phosphoramidate (62.2 mg, 0.14 mmol) in CH$_3$CN (1 mL) followed by 5-ethylthio-1H-tetrazole in CH$_3$CN (0.25M; 0.56 mL, 0.14 mmol) at 0 to 5° C. dropwise. The mixture was stirred 2 h at 0 to 5° C. under Ar. A solution of 77% m-CPBA (49 mg, 0.22 mmol) in DCM (1 mL) was added, and the mixture was stirred 2 h at 0 to 5° C. under Ar. The mixture was diluted with EtOAc (50 mL), washed with 1.0M citric acid, sat. NaHCO$_3$, and brine, and dried with MgSO$_4$. The mixture was filtered and the solvents were evaporated in vacuo. The residue was purified on silica (10 g column) with EA/hexanes (10-100% gradient) to give 29-1 (72 mg, 50.8%) as a white solid.

Preparation of (29A)

29-1 (72 mg, 0.056 mmol) was dissolved in anhydrous CH$_3$CN (1.0 mL), and 4N HCl in dioxane (87 µL, 0.35 mmol) was added at 0 to 5° C. The mixture was stirred at R.T. for 2 h. Intermediate 29-2 was observed by LCMS. The solvents were evaporated at R.T. and co-evaporated with toluene (3×). The residue obtained was re-dissolved in 80% HCOOH (2 mL). The mixture was stirred at R.T. for 4.5 h. The solvents were evaporated at R.T. and co-evaporated with toluene (3×). Anhydrous EtOH (3×5 mL) was added.

The residue was dissolved in 50% CH₃CN/H₂O, purified on a reverse-phase HPLC (C18) using CH₃CN and H₂O, and lyophilized to give 29A (19.2 mg) as a white foam. ESI-LCMS: m/z=669.2 [M+H]⁺, 1337.25 [2M+H]⁺.

Example 18

Preparation of Compound 30A

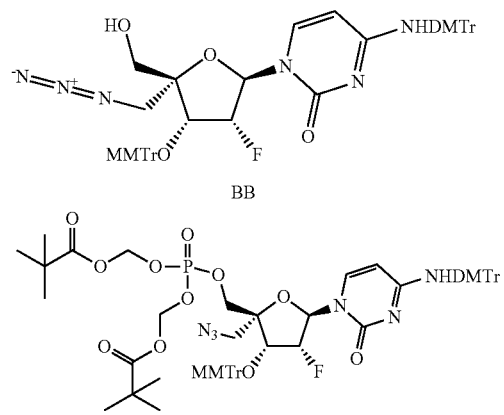

BB 30-1

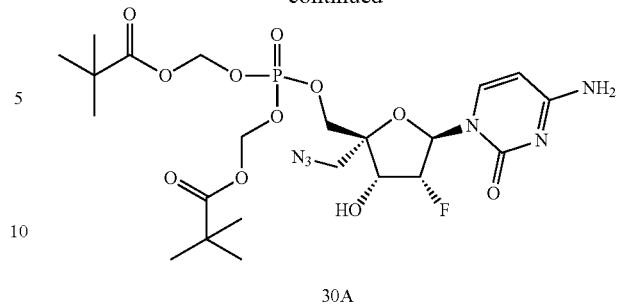

30A

Preparation of (30-1)

30-1 (98 mg, 72.6%) was prepared in the same manner from BB (100 mg, 0.114 mmol) and bis(tert-butoxycarbonyloxymethyl)phosphate (83 mg, 0.35 mmol) with DIPEA (126 μL, 0.69 mmol), BOP-Cl (87 mg, 0.34 mmol), and 3-nitro-1,2,4-triazole (39 mg, 0.34 mmol) in THF (1.5 mL) in the same manner as 13-4.

Preparation of (30A)

30A (30.2 mg, 60%) was prepared from 30-1 (98 mg, 0.083 mmol) in the same manner as 17A. ESI-LCMS: m/z=609.15 [M+H]⁺, 1217.3 [2M+H]⁺.

Example 19

Preparation of Compound 21A

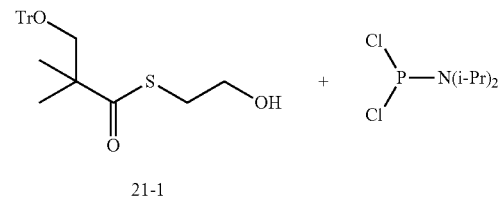

21-1

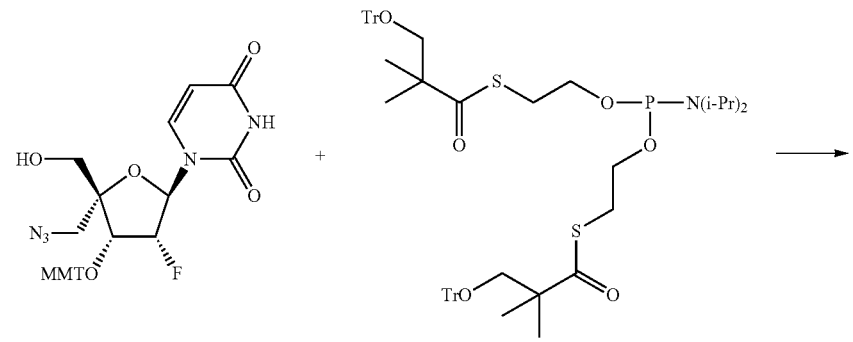

21-2                    21-3

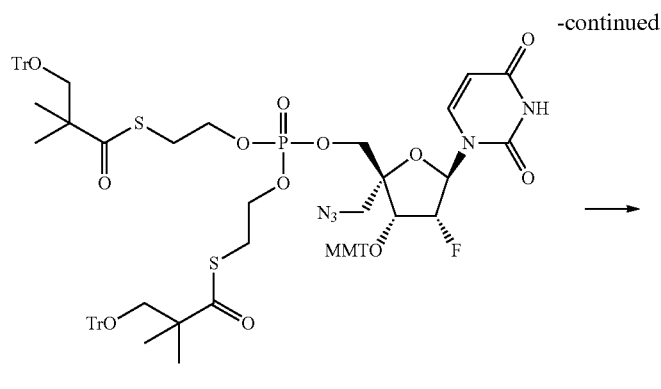

21-4

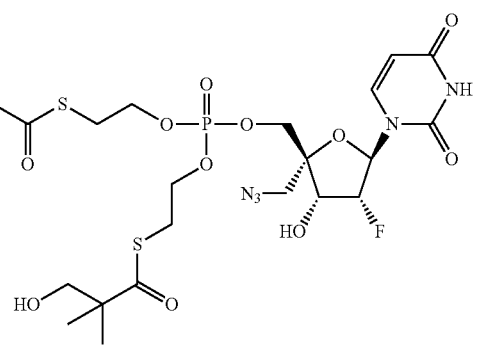

21A

Preparation of (21-3)

A solution of 21-1 (4.7 g, 11.2 mmol; prepared according to the procedure Villard et al., *Bioorg. Med. Chem.* (2008) 16:7321-7329) and Et$_3$N (3.4 mL, 24.2 mmol) in THF (25 mL) was added dropwise over 1 h to a stirred solution of N,N-diisopropylphosphorodichloridite (1.0 mL, 5.5 mmol) in THF (35 mL) at −75° C. The mixture was stirred at R.T. for 4 h. The mixture was filtered, and the filtrate concentrated. The oily residue was purified on silica gel column with EtOAc/hexanes (2-20% gradient) to give 21-3 (1.4 g, 26%).

Preparation of (21-4)

To a solution of 21-2 (50 mg, 0.08 mmol) and 21-3 (110 mg, 0.11 mmol) in CH$_3$CN (1.0 mL) was added 5-(ethylthio) tetrazole (0.75 mL, 0.16 mmol; 0.25 M in CH$_3$CN). The mixture was stirred at R.T. for 1 h. The mixture was cooled to −40° C., and a solution of 3-chloroperoxybenzoic acid (37 mg, 0.16 mmol) in CH$_2$Cl$_2$ (0.3 mL) was added. The mixture was warmed to R.T. over 1 h. The reaction was quenched with 7% Na$_2$S$_2$O$_3$ solution in sat aq. NaHCO$_3$. The mixture was diluted with EtOAc, and the layers were separated. The organic layer was washed with brine and dried with Na$_2$SO$_4$. The solvent was evaporated, and the residue was purified on a silica gel column with EtOAc/hexanes (30-100% gradient) to give 21-4 (52 mg, 45%).

Preparation of (21A)

A solution of 21-4 (52 mg, 0.036 mmol) in MeCN (0.5 mL) and HCl (45 μL; 4 N in dioxane) was stirred 20 h at R.T. The reaction was quenched with MeOH, and the solvents were evaporated. The residue was co-evaporated with toluene and purified on a silica gel column with MeOH/CH$_2$Cl$_2$ (4-10% gradient) to give 21A (14 mg, 51%). ESI-LCMS: m/z=702 [M+H]$^+$.

Example 20

Preparation of Compound 22A

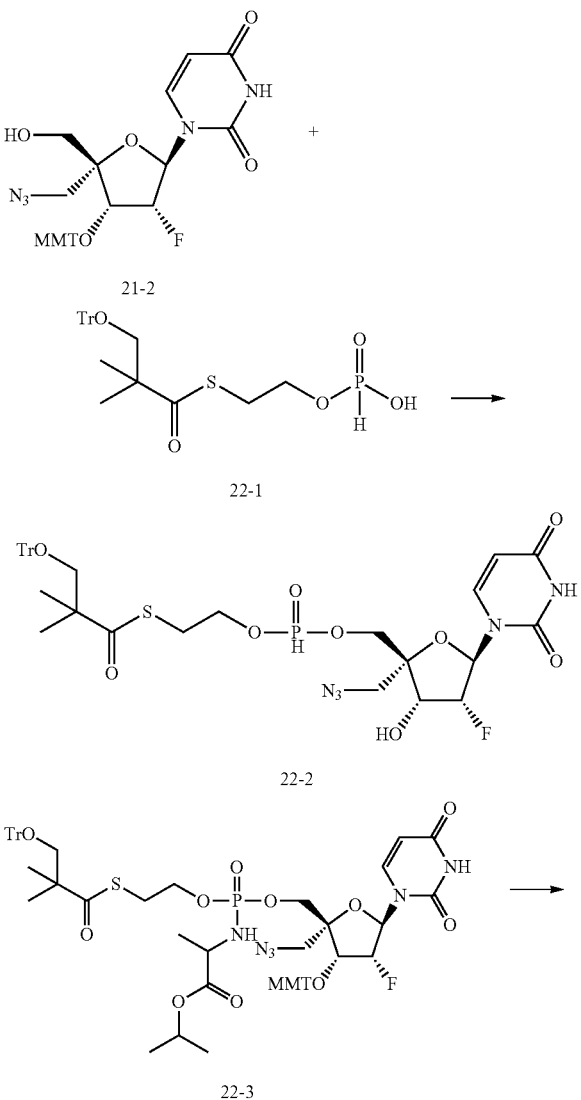

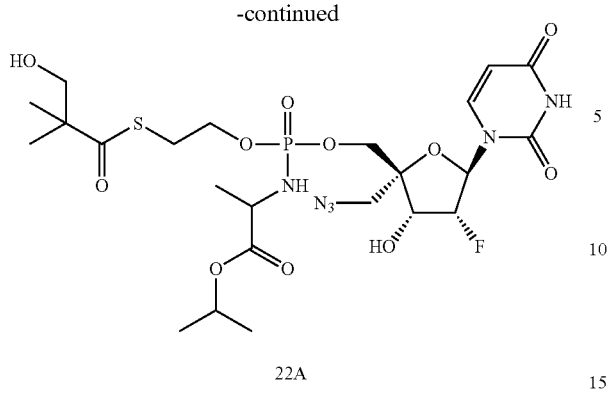

Preparation of (22-2)

A mixture of 22-1 (0.14 g, 0.24 mmol; prepared according to the procedure described in WO 2008/082601, filed Dec. 28, 2007) and 21-2 (120 mg, 0.2 mmol) was rendered anhydrous by evaporating with pyridine and then dissolved in pyridine (3 mL). Pivaloyl chloride (48 μL) was added dropwise at −15° C. The mixture was stirred at −15° C. for 2 h. The reaction was quenched with sat. aq. NH$_4$Cl solution and diluted with CH$_2$Cl$_2$. The organic layer was washed with brine and dried with Na$_2$SO$_4$. The solvents were evaporated, and the residue was purified on a silica gel column with EtOAc/hexanes (30-100% gradient) to give 22-2 (50 mg, 24%).

Preparation of (22-3)

A mixture of 22-2 (43 mg; 0.04 mmol) in CCl$_4$ (0.8 mL), L-valine isopropyl ester hydrochloride (20 mg, 0.12 mmol) and Et$_3$N (33 μl, 0.24 mmol) was stirred at R.T. for 2 h. The mixture was diluted with EtOAc. The mixture was washed with sat. aq. NaHCO$_3$ and brine, and dried with Na$_2$SO$_4$. The solvents were evaporated, and the residue was purified on a silica gel column with i-PrOH/CH$_2$Cl$_2$ (2-10% gradient) to 22-3 (35 mg, 75%).

Preparation of (22A)

A solution of 22-3 (35 mg, 0.03 mmol) in MeCN (0.4 mL) and HCl (40 μL; 4 N in dioxane) was stirred 4 h at R.T. The reaction was quenched with the addition of MeOH, and the solvents were evaporated. The residue was co-evaporated with toluene and purified on a silica gel column with MeOH/CH$_2$Cl$_2$ (4-10% gradient) to give 23A (11 mg, 56%). ESI-LCMS: m/z=655 [M+H]$^+$.

Example 21

Preparation of Compound 7A

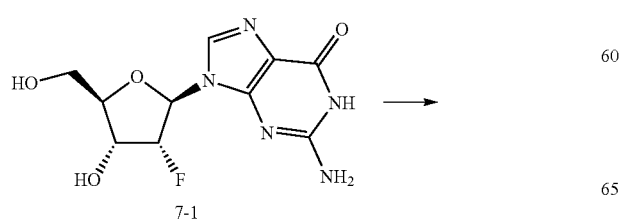

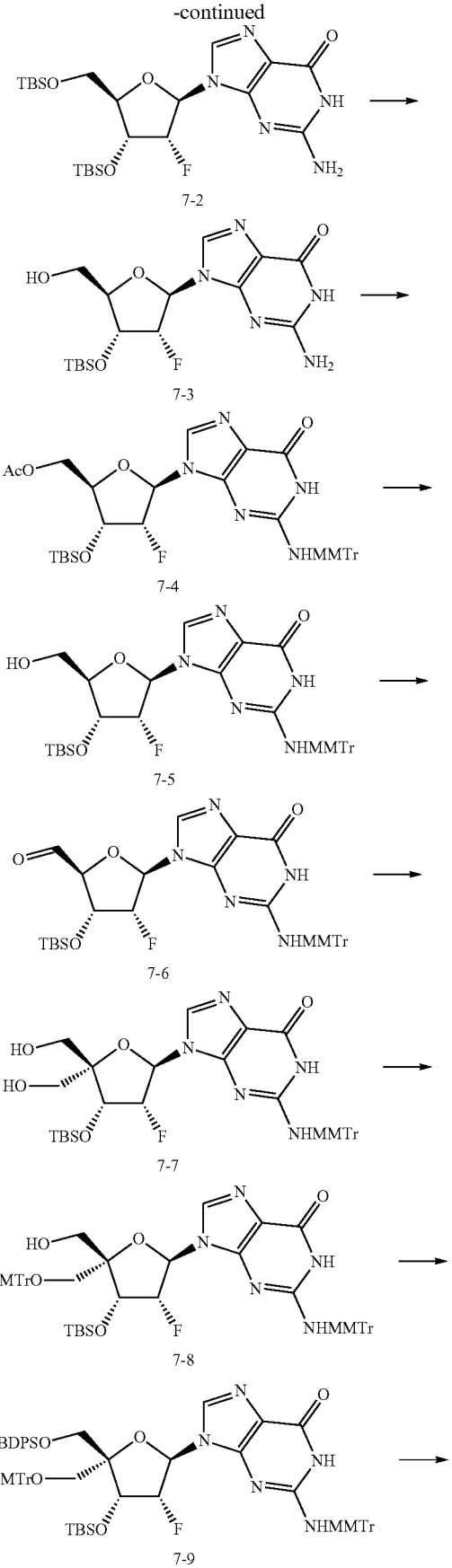

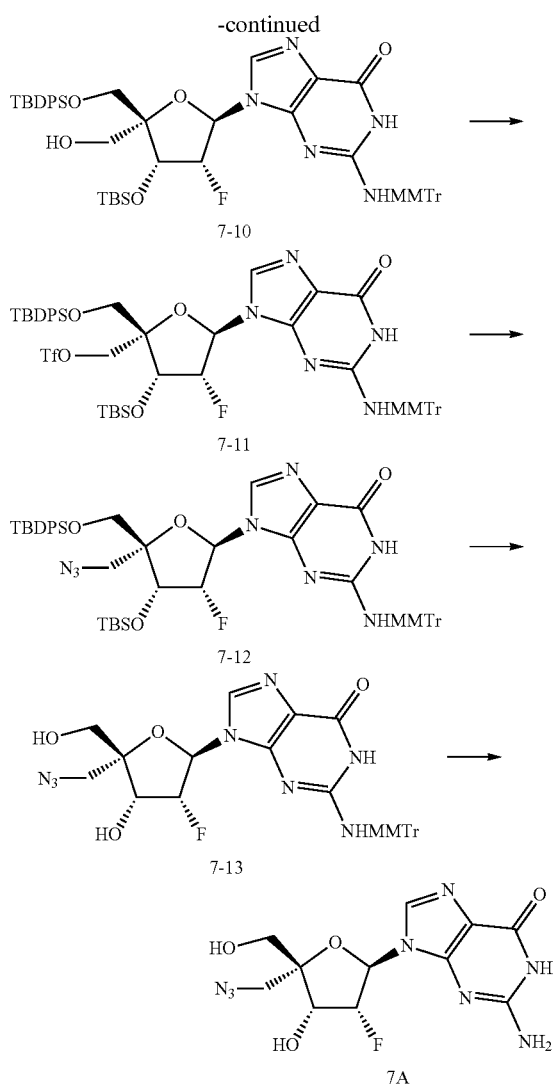

7-10

7-11

7-12

7-13

7A

Preparation of (7-2)

To a solution of 7-1 (20.0 g, 70.1 mmol) in anhydrous pyridine (230 mL) was added imidazole (19.1 g, 280.7 mmol) and TBSCl (42.1 g, 280.7 mmol) at 25° C. The solution was stirred at 25° C. for 15 h. The mixture was concentrated to dryness under reduced pressure, and the residue was dissolved in EA. A white solid was obtained and filtered. The filter cake was concentrated to dryness to give 7-2 (30.1 g, 83%) as a white solid.

Preparation of (7-3)

7-2 (30.1 g, 58.7 mmol) was dissolved in THF (120 mL) and $H_2O$ (80 mL). HOAc (260 mL) was added, and was then stirred at 80° C. for 13 h. The mixture was cooled to R.T., and concentrated to dryness under reduced pressure. The residue was dissolved in EA and filtered. The filter cake was concentrated to dryness to give 7-3 (20.1 g, 86%) as a white solid.

Preparation of (7-4)

7-3 (20.1 g, 50.4 mmol) was dissolved in anhydrous pyridine (200 mL). $Ac_2O$ (7.7 g, 75.5 mmol) was added and was then stirred at 25° C. for 18 h. MMTrCl (46.5 g, 151.1 mmol) and $AgNO_3$ (25.5 g, 151.1 mmol) were added. The solution was stirred at 25° C. for 15 h. The reaction was quenched with water. The mixture was concentrated to dryness under reduced pressure, and the residue was dissolved in EA. The solution was washed with brine. The organic layer was dried over $Na_2SO_4$ and filtered. The filtrate was concentrated in vacuum to dryness. The residue was purified on silica gel column (2% MeOH in DCM) to give 7-4 (21.5 g, 60%) as a white foam.

Preparation of (7-5)

7-4 (4.3 g, 6.0 mmol) was dissolved in $NH_3$/MeOH (40 mL). The mixture was stirred at 25° C. for 20 h. The solution was evaporated to dryness. The residue was purified on silica gel column (2% MeOH in DCM) to give 7-5 (3.1 g, 76.5%) as a yellow solid.

Preparation of (7-6)

To a solution of 7-5 (3.1 g, 4.6 mmol) in anhydrous DCM (50 mL) was added Dess-Martin reagent (3.5 g, 8.2 mmol) at 0° C. The mixture was stirred at 0° C. for 2 h, and then stirred at R.T. for 2 h. The reaction was quenched with saturated $NaHCO_3$ and $Na_2S_2O_3$ solution. The organic layer was washed with brine (2×) and dried over anhydrous $Na_2SO_4$. The solvent was evaporated to give crude 7-6 (2.8 g) as a yellow foam.

Preparation of (7-7)

To a solution of 7-6 (2.8 g, 4.2 mmol) in 1,4-dioxane (40 mL) was added 37% HCHO (2.7 g, 33.5 mmol) and 2.0 N NaOH aqueous solution (3.0 mL, 6.0 mmol). The mixture was stirred for 12 h at 25° C. The mixture was treated with EtOH (20 mL) and $NaBH_4$ (2.5 g, 66.9 mmol) and stirred for 30 mins. The reaction was quenched with sat. aq. $NH_4Cl$ and extracted with EA (50 mL). The organic layer was dried over $Na_2SO_4$. The concentrated organic phase was purified on silica gel column (2% MeOH in DCM) to give 7-7 (2.1 g, 72.4%) as a yellow solid.

Preparation of (7-8)

To a solution of 7-7 (2.1 g, 3.0 mmol) in DCM (20 mL) was added pyridine (5 mL) and DMTrCl (1.0 g, 3.0 mmol) at 0° C. The solution was stirred at 25° C. for 1 h. The mixture was treated with MeOH (8 mL), and concentrated under reduced pressure. The residue was purified on silica gel column (2% MeOH in DCM) to give 7-8 (1.1 g, 36.7%) as a yellow solid.

Preparation of (7-9)

To a solution of 7-8 (1.1 g, 1.1 mmol) in anhydrous pyridine (10 mL) was added TBDPSCl (0.9 g, 3.3 mmol) and $AgNO_3$ (0.6 g, 3.3 mmol). The mixture was stirred at 25° C. for 15 h. The solid was removed by filtration, and the filtrate was concentrated at low pressure. The residue was dissolved in EA. The resulting solution was washed with brine. The organic layer was dried over $Na_2SO_4$ and concentrated at low pressure. The residue was purified by column chromatography (2% MeOH in DCM) to give 7-9 (1.2 g, 88.2%) as a white foam.

Preparation of (7-10)

To a solution of 7-9 (1.2 g, 1.0 mmol) in anhydrous DCM (15 mL) was added $Cl_2CHCOOH$ (0.6 mL) at −78° C. The mixture was stirred at −20° C. for 1 h. The reaction was quenched with sat. aq. NaHCO₃ and extracted with DCM. The organic layer was dried over Na₂SO₄ and concentrated at low pressure. The residue was purified on silica gel column (2% MeOH in DCM) to give 7-10 (693 mg, 76.3%) as a white foam.

Preparation of (7-11)

To a solution of 7-10 (693 mg, 0.74 mmol) in anhydrous DCM (25 mL) and pyridine (291 mg, 3.70 mmol) was added Tf₂O (312 mg, 1.1 mmol) in DCM (1 mL) dropwise at 0° C. The mixture was stirred at 0° C. for 15 mins. The reaction was quenched with ice water. The organic layer was separated and washed with brine. The organic layer was dried over anhydrous Na₂SO₄ and evaporated to give 7-11 (442 mg, crude) as a yellow foam.

Preparation of (7-12)

To a solution of 7-11 (442 mg, 0.41 mmol) in anhydrous DMF (5 mL) was added NaN₃ (134 mg, 2.1 mmol). The mixture was stirred at R.T. for 12 h. The reaction was quenched with water and extracted with EA (20 mL, 2×). The organic layer were washed with brine, dried over anhydrous Na₂SO₄, and concentrated at low pressure. The residue was purified on a silica gel column (1% MeOH in DCM) to give pure 7-12 (313 mg, 78.6%) as a white foam.

Preparation of (7-13)

A mixture of 7-12 (313 mg, 0.32 mmol) and NH₄F (240 mg, 6.5 mmol) in MeOH (10 mL) was stirred at 80° C. for 12 h. The mixture was cooled down to R.T. The solid was removed by filtration. The solvent was removed under reduced pressure, and the residue was purified on a silica gel column (5% MeOH in DCM) to give 7-13 (102 mg, 52%) as a white foam.

Preparation of (7A)

7-13 (102 mg, 0.17 mmol) was dissolved in CH₃COOH (80%). The mixture was stirred at 60° C. for 2 h and then cooled to R.T. The mixture was concentrated to dryness under reduced pressure. The residue was purified on silica gel column (5% to 10% MeOH in DCM) to give the crude product (67 mg). The crude product was purified by prep-HPLC (0.1% NH₄HCO₃ in water and CH₃CN) to give 7A (37.5 mg, 66%) as a white solid. MS: m/z 341[M+H]⁺.

Example 22

Preparation of Compound 31A

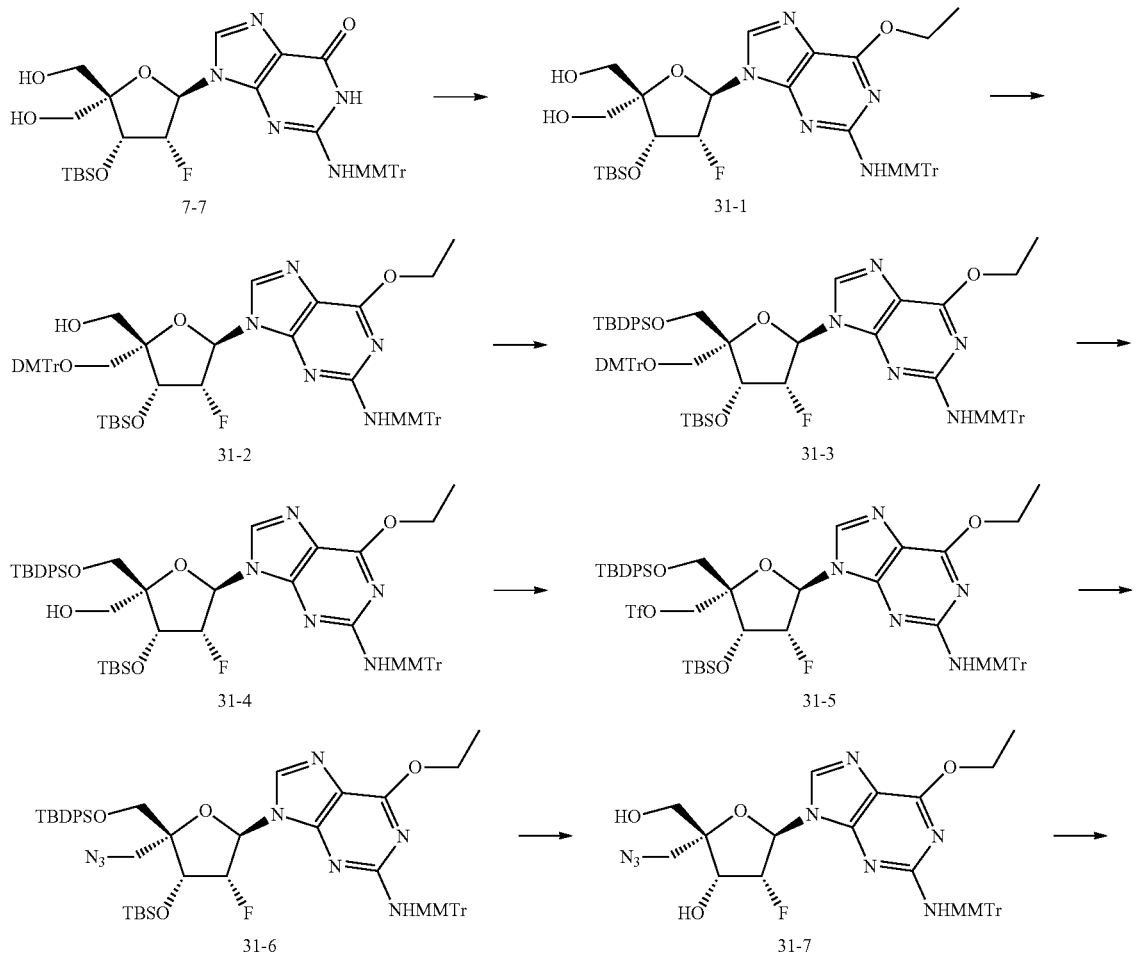

-continued

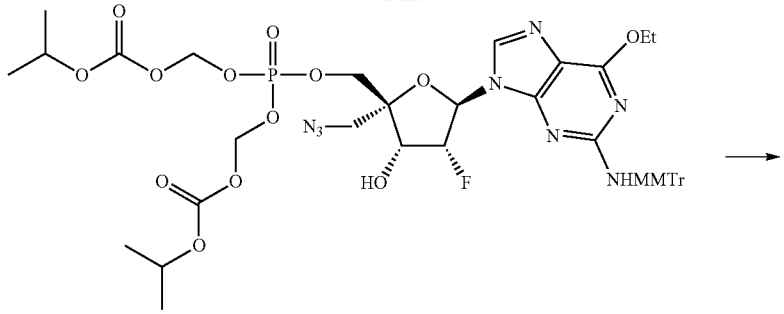

31-8

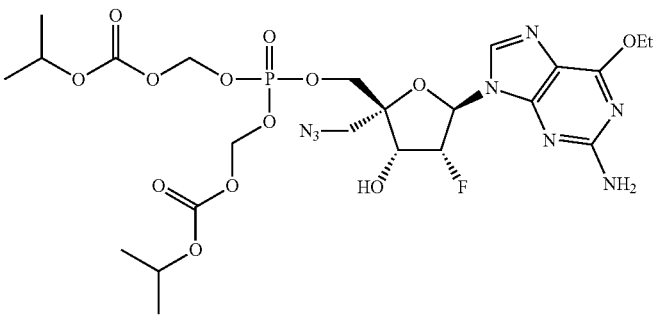

31A

Preparation of (31-2)

To a stirred solution of 7-7 (1.92 g, 27.3 mmol), PPh₃ (1.43 g, 54.7 mmol), EtOH (0.25 g, 54.7 mmol) in anhydrous dioxane (20 mL) was added DIAD (1.11 g, 54.7 mmol) dropwise at 0° C. The solution was stirred at 25° C. for 15 h. The reaction was quenched with water and extracted with EA. The mixture was washed with water and brine. The organic layer was dried over Na₂SO₄ and filtered. The filtrate was concentrated in vacuum to dryness, and the residue was purified on a silica gel column (2% to 5% MeOH in DCM) to give 31-1 (1.43 g, 71%) as a white foam.

Preparation of (31-2)

To a stirred solution of 31-1 (1.43 g, 19.6 mmol) in DMF (15 mL) was added TEA (0.59 g, 58.8 mmol) and DMTrCl (0.99 g, 29.4 mmol) at 0° C. The solution was stirred at 25° C. for 12 h. The mixture was treated with MeOH (1 mL), and diluted with EA. The solution was washed with water and brine. The organic layer was dried over anhydrous NaSO₄, and concentrated to dryness. The residue was purified on a silica gel column (2% MeOH in DCM) to give 31-2 (1.13 g, 56%) as a yellow solid.

Preparation of (31-3)

To a stirred solution of 31-2 (1.13 g, 1.1 mmol) in anhydrous pyridine (10 mL) was added TBDPSCl (0.91 g, 3.3 mmol) and AgNO₃ (0.61 g, 3.3 mmol). The mixture was stirred at 25° C. for 15 h. The solid was removed by filtration, and the filtrate was diluted with EA (50 mL). The solution was washed with brine. The organic layer was dried over anhydrous Na₂SO₄, and concentrated at low pressure. The residue was purified on a silica gel column (2% MeOH in DCM) to give 31-3 (1.22 g, 88%) as a white foam.

Preparation of (31-4)

To a stirred solution of 31-3 (1.22 g, 1.0 mmol) in anhydrous DCM (15 mL) was added Cl₂CHCOOH (0.6 mL) at −78° C. The mixture was stirred at −20° C. for 1 h. The reaction was quenched with sat. aq. NaHCO₃ and extracted with DCM. The organic layer was dried over anhydrous Na₂SO₄, and concentrated at low pressure. The residue was purified by column chromatography (2% MeOH in DCM) to give 31-4 (0.52 g, 56%) as a white foam.

Preparation of (31-5)

To a stirred solution of 31-4 (0.52 g, 0.5 mmol) in anhydrous DCM (15 mL) and pyridine (0.21 g, 2.5 mmol) was added Tf₂O (0.30 g, 1.0 mmol) in DCM (1 mL) dropwise at 0° C. The mixture was stirred at 0° C. for 15 mins. The reaction was quenched with ice water. The organic layer was separated and washed with water. The organic layer was dried over anhydrous Na₂SO₄ and concentrated at low pressure to give 31-5 (442 mg crude) as a yellow foam.

Preparation of (31-6)

To a stirred solution of 31-5 (442 mg, 0.4 mmol) in anhydrous DMF (5 mL) was added NaN₃ (131 mg, 2.0 mmol). The mixture was stirred at RT for 12 h. The reaction was quenched with water and extracted by EA (20 Ml, 2×). The organic layer was washed with water and dried over Na₂SO₄. The organic phase was evaporated to dryness under reduced pressure. The residue was purified on a silica gel column (1% MeOH in DCM) to give 31-6 (352 mg, 88%) as a white foam.

Preparation of (31-7)

A mixture of 31-6 (352 mg, 0.35 mmol) and NH₄F (392 mg, 10.6 mmol) in MeOH (10 mL) was stirred at 80° C. for 12 h. The mixture was cooled to R.T. The solid was removed by filtration. The solvent was concentrated under reduced pressure. The residue was purified on a silica gel column (2% to 5% MeOH in DCM) to give crude 31-7 (151 mg). The crude product was purified by prep-HPLC (0.1% NH$_4$HCO$_3$ in water and CH$_3$CN) to give 31-7 (71.5 mg, 32%) as a white solid. MS: m/z 641 [M+H]$^+$.

Preparation of (31-8)

A mixture of 31-7 (64 mg, 0.1 mmol) and bis(pivaloyloxymethyl)phosphate, after rendered anhydrous by evaporating with toluene, was dissolved in CH$_3$CN (1 mL) and cooled to 0° C. BopCl (40 mg, 0.15 mmol) and NMI (40 μL, 0.5 mmol) were added. The mixture was stirred at 0° C. for 2 h. EtOAc was added, and the mixture was washed with 0.5 N aq. citric acid, sat. aq. NaHCO$_3$ and brine, and then dried with Na$_2$SO$_4$. The solvents were removed, and the residue was purified on a silica gel column with 3% i-PrOH in CH$_2$Cl$_2$ to 31-8 (38 mg, 40%).

Preparation of (31A)

A solution of 31-8 (30 mg, 0.03 mmol) in CH$_3$CN (0.3 mL) and HCl (30 μL; 4 N dioxane) was stirred at R.T. for 100 mins. The reaction was quenched with EtOH, and the mixture was evaporated. The crude residue was purified on a silica gel column with i-PrOH/CH$_2$Cl$_2$ (3-10% gradient) to yield 31A (10 mg, 50%). ESI-LCMS: m/z=681 [M+H]$^+$.

Example 23

Preparation of Compound 32A

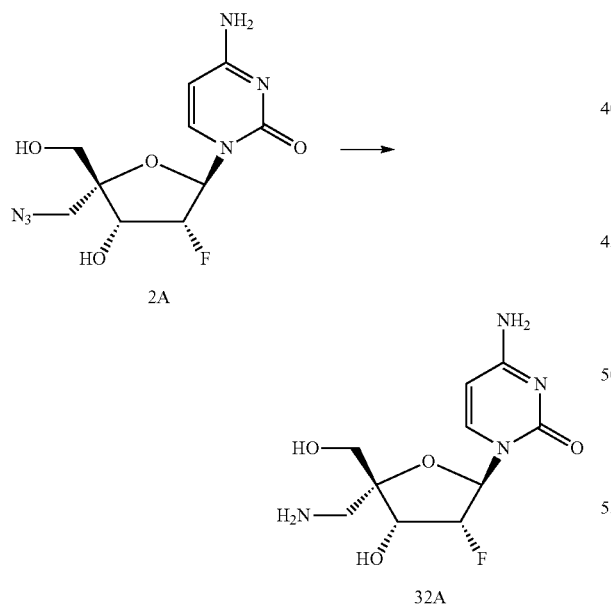

2A (30 mg, 0.1 mmol) was hydrogenated in MeOH over 10% Pd/C at normal pressure. The catalyst was filtered off, and the filtrate was purified by RP HPLC on Synergy 4 micron Hydro-RP column (Phenominex). A linear gradient of MeOH from 0 to 20% in 50 mM triethylammonium acetate buffer (pH 7.5) was used for elution. The corresponding fractions were combined, concentrated and lyophilized (3×) to remove excess of buffer to yield 32A (17 mg, 63%). ESI-LCMS: m/z=275.2 [M+H]$^+$, 297.1 [M+Na]$^+$.

Example 24

Preparation of Compound 8A

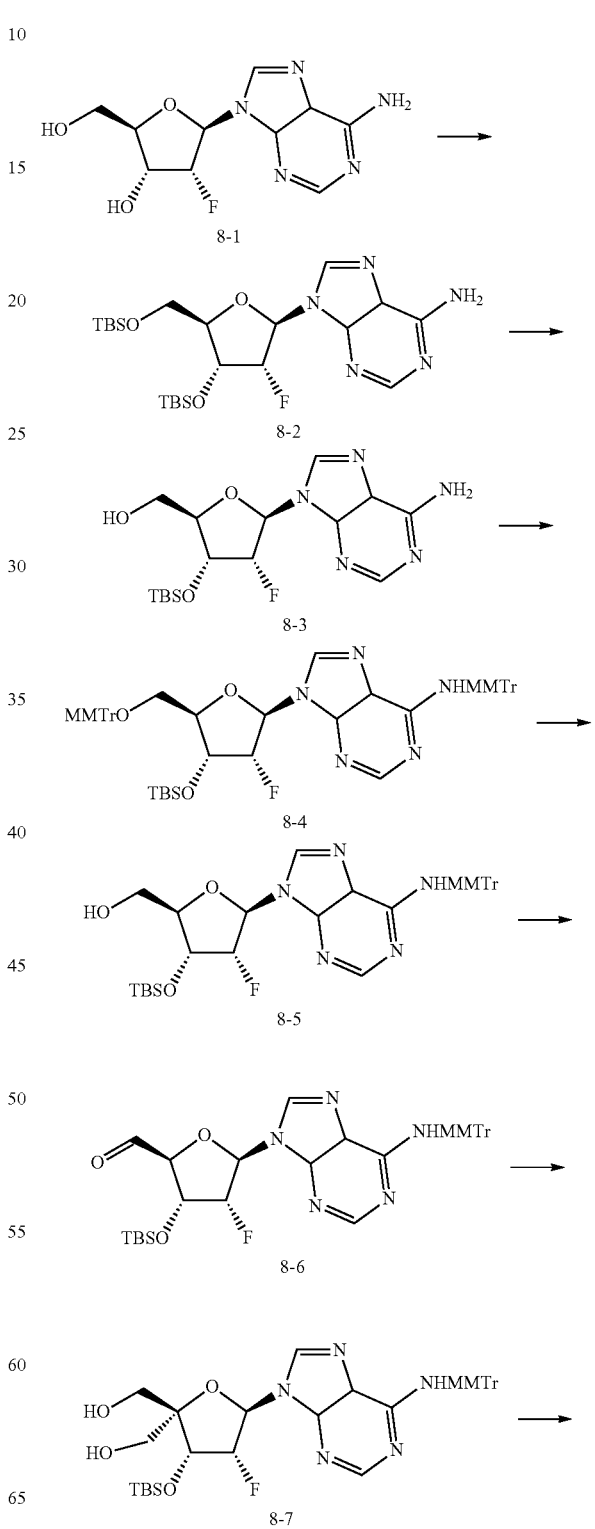

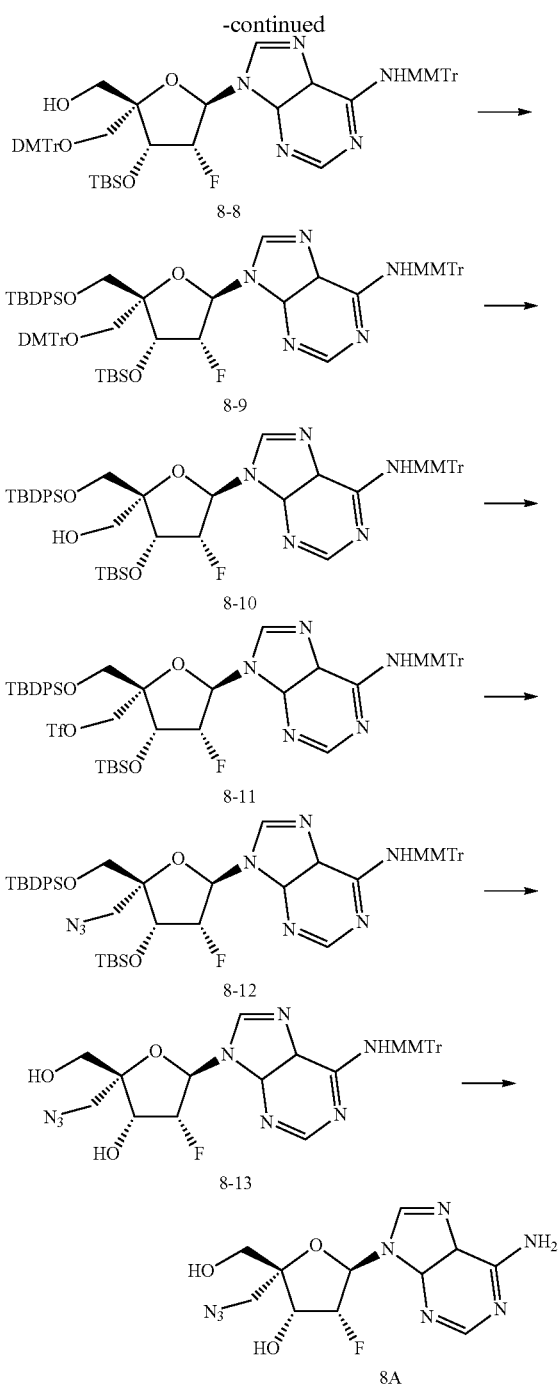

Preparation of (8-3)

To a stirred solution of 8-2 (3.5 g, 7.04 mmol) in a mixture of EA and EtOH (1:1, 55 mL) was added TsOH (10.7 g, 56.34 mmol) at 0° C. The mixture was stirred at 30° C. for 8 h. Water (30 mL) was added, and the solution was removed to dryness. The residue was purified on a silica gel column (10% MeOH in DCM) to give 8-3 (1.75 g, 65%) as a white foam.

Preparation of (8-4)

To a solution of 8-3 (3.4 g, 8.88 mmol) in anhydrous pyridine (17 mL) was added collidine (4.3 g, 35.51 mmol), AgNO$_3$ (5.50 g, 35.51 mmol) and MMTrCl (8.02 g, 26.63 mmol) at 25° C. under N$_2$. The mixture was stirred at 25° C. for 12 h. MeOH (20 mL) was added, and the solvent was removed to dryness at low pressure. The residue was purified on a silica gel column (10% EA in PE) to give 8-4 (5.76 g, 70%) as a white foam.

Preparation of (8-5)

To a solution of 8-4 (2.0 g, 2.16 mmol) in anhydrous DCM (10 mL) was added Cl$_2$CHCOOH (2.8 g, 21.57 mmol) dropwise at −78° C. The mixture was warmed to −10° C. and stirred at this temperature for 20 mins. The reaction was quenched with sat. NaHCO$_3$ at −10° C. The mixture was extracted with DCM, washed with brine, and dried over anhydrous MgSO$_4$. The solution was concentrated at low pressure. The residue was purified on silica gel column (10% EA in PE) to give 8-5 (0.99 g, 70%) as a white foam.

Preparation of (8-6)

To a stirred solution of 8-5 (3.5 g, 5.34 mmol) in anhydrous DMSO (35 mL) was added DCC (3.30 g, 16.03 mmol) and Py.TFA (1.03 g, 5.34 mmol). The mixture was stirred at 30° C. for 1 h. The reaction was quenched with cold water at 0° C., and extracted with EA (3×60 mL). The precipitate was filtered. The organic layers were washed with brine (3×) and dried over anhydrous MgSO$_4$. The organic phase was concentrated at low pressure to give crude 8-6 (3.5 g) as a yellow oil.

Preparation of (8-7)

To a stirred solution of 8-6 (3.5 g, 5.34 mmol) in MeCN (35 mL) was added 37% HCHO (11.1 mL) and TEA (4.33 g, 42.7 mmol). The mixture was stirred at 25° C. for 12 h. The mixture was treated with EtOH (26 mL) and NaBH$_4$ (3.25 g, 85.5 mmol) and then stirred for 30 mins. The reaction was quenched with sat. aq. NH$_4$Cl and extracted with EA (3×60 mL). The organic layer was dried over anhydrous MgSO$_4$, and concentrated at low pressure. The residue was purified by column chromatography (from 10% EA in PE to 50% DCM in PE) to give 8-7 (1.46 g, 40%) as a white solid.

Preparation of (8-8)

To a stirred solution of 8-7 (1.85 g, 2.7 mmol) in pyridine (24 mL) and DCM (9.6 mL) was added DMTrCl (1.3 g, 3.9 mmol) at −35° C. under N$_2$ atmosphere. The solution was stirred at 25° C. for 16 h. The mixture was treated with MeOH (15 mL) and concentrated at low pressure. The Preparation of (8-2)

To a solution of 8-1 (3.0 g, 11.15 mmol) in anhydrous pyridine (90 mL) was added imidazole (3.03 g, 44.59 mmol) and TBSCl (6.69 g, 44.59 mmol) at 25° C. under N$_2$ atmosphere. The solution was stirred at 25° C. for 15 h. The solution was concentrated to dryness under reduced pressure. The residue was dissolved in EA. The solution was washed with sat. NaHCO$_3$ and brine, and dried over anhydrous MgSO$_4$. The solvent was removed at low pressure to give crude 8-2 (4.49 g, 90%) as a white solid.

residue was purified by column chromatography (EA in PE from 10% to 30%) to give 8-8 (1.60 g, 60%) as a white solid.

Preparation of (8-9)

To a solution of 8-8 (1.07 g, 1.08 mmol) in anhydrous pyridine (5 mL) was added AgNO$_3$ (0.65 g, 3.79 mmol) and TBDPSCl (1.04 g, 3.79 mmol). The mixture was stirred at 25° C. for 16 h. The solvent was removed under reduced pressure. The residue was dissolved in EA (50 mL). The resulting solution was washed with brine. The organic layer was dried over anhydrous MgSO$_4$, and concentrated at low pressure. The residue was purified on a silica gel column (10% EA in PE) to give 8-9 (0.93 g, 70%) as a white foam.

Preparation of (8-10)

To a stirred solution of 8-9 (1 g, 0.82 mmol) in anhydrous DCM (13.43 mL) was added Cl$_2$CHCOOH (2.69 mL) at −78° C. The mixture was stirred at −10° C. for 20 mins. The reaction was quenched with sat. aq. NaHCO$_3$ and extracted with DCM. The organic layer was dried over anhydrous Na$_2$SO$_4$, and concentrated at low pressure. The organic phase was purified by column chromatography (MeOH in DCM form 0.5% to 2%) to give 8-10 (0.48 g, 65%) as a solid.

Preparation of (8-11)

To an ice cold solution of 8-10 (0.4 g, 0.433 mmol) in anhydrous DCM (2.7 mL) was added pyridine (171 mg, 2.17 mmol) and Tf$_2$O (183 mg, 0.65 mmol) by dropwise at −35° C. The mixture was stirred at −10° C. for 20 mins. The reaction was quenched with ice water and stirred for 30 mins. The mixture was extracted with DCM (3×20 mL). The organic phase was washed with brine (100 mL), dried over anhydrous Na$_2$SO$_4$, and concentrated at low pressure to give crude 8-11 (0.46 g), which was used for next step without further purification.

Preparation of (8-12)

To a solution of 8-11 (0.46 g, 0.43 mmol) in anhydrous DMF (2.5 mL) was added NaN$_3$ (42 mg, 0.65 mmol). The mixture was stirred at 30° C. for 16 h. The solution was diluted with water and extracted with EA (3×30 mL). The combined organic layers were dried over anhydrous Na$_2$SO$_4$, and concentrated at low pressure. The residue was purified on a silica gel column (EA in PE from 5% to 15%) to give 8-12 (0.31 g, 70%) as a solid.

Preparation of (8-13)

To a solution of 8-12 (0.31 g, 0.33 mmol) in MeOH (5 mL) was added NH$_4$F (0.36 g, 9.81 mmol) at 70° C. The mixture was stirred at this temperature for 24 h. The mixture was evaporated to dryness. The residue was purified on silica gel column (MeOH in DCM from 0.5% to 2.5%) to give 8-13 (117 mg, 60%) as a white solid.

Preparation of (8A)

8-13 (300 mg, 0.50 mmol) was dissolved in 80% of HOAc (20 mL). The mixture was stirred at 55° C. for 1 h. The reaction was quenched with MeOH and concentrated at low pressure. The residue was purified by prep-HPLC to give 8A (100 mg, 61.3%) as a white solid. ESI-LCMS: m/z 325.1 [M+H]$^+$.

Example 25

Preparation of Compound 33A

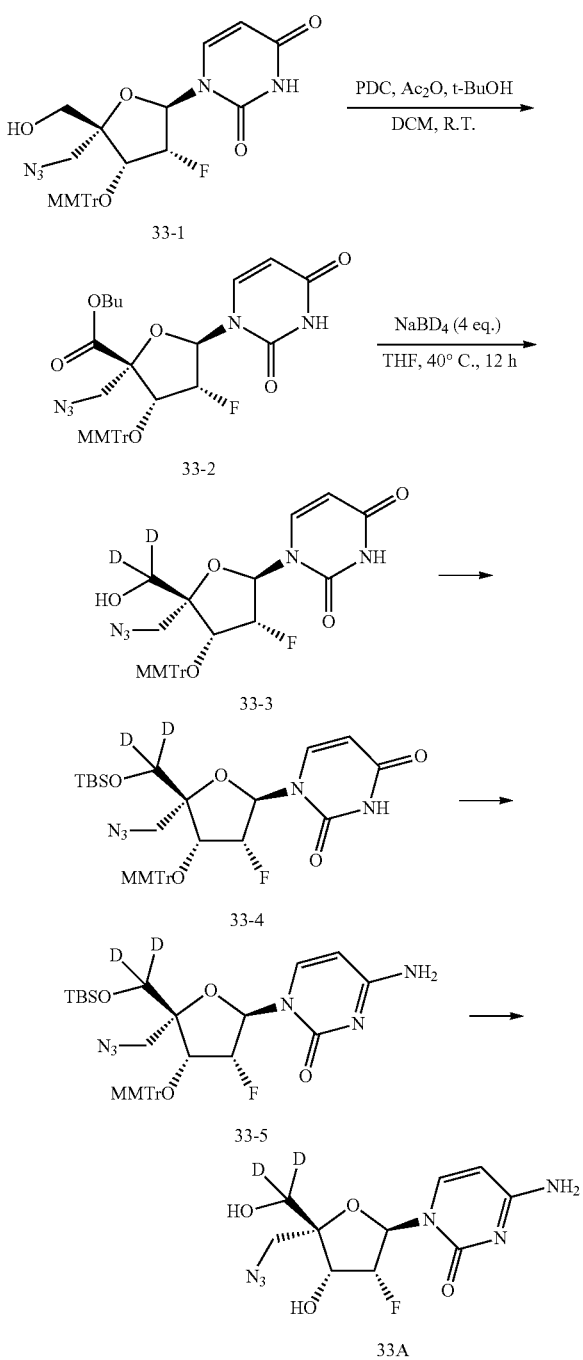

Compound 33-3 was prepared according to the scheme provided above. Compound 33A can be obtained using methods known to those skilled in the art, including those described in U.S. Publication No. 2012/0071434, filed Sep. 19, 2011.

Example 26

Preparation of Triphosphate Compounds

Compounds 3A, 4A, 9A and 11A

Dry nucleoside (0.05 mmol) was dissolved in a mixture of $PO(OMe)_3$ (0.7 mL) and pyridine (0.3 mL). The mixture was evaporated in vacuum for 15 mins at a bath temperature of 42° C., and then cooled down to R.T. N-Methylimidazole (0.009 mL, 0.11 mmol) was added followed by $POCl_3$ (9 μL, 0.11 mmol), and the mixture was kept at R.T. for 40 mins. The reaction was controlled by LCMS and monitored by the appearance of the corresponding nucleoside 5'-monophosphate. After more than 50% of transformation was achieved, tetrabutylammonium salt of pyrophosphate (150 mg) was added, followed by DMF (0.5 mL) to get a homogeneous solution. After 1.5 hours at ambient temperature, the reaction was diluted with water (10 mL) and loaded on the column HiLoad 16/10 with Q Sepharose High Performance. Separation was done in a linear gradient of NaCl from 0 to 1N in 50 mM TRIS-buffer (pH7.5). Triphosphate was eluted at 75-80% B. Corresponding fractions were concentrated. Desalting was achieved by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer.

Compounds 5A, 6A, 10A and 12A

Nucleoside 5'-triphosphates with a 4'-azidoalkyl group were dissolved in water (0.1 mL), methanol (3 mL) was added followed by 10% Pd/C (3 mg). Hydrogen was bubbled through the solution for 2 h. The catalyst was filtered off, and the filtrate was purified by RP HPLC on Synergy 4 micron Hydro-RP column (Phenominex). A linear gradient of methanol from 0 to 20% in 50 mM triethylammonium acetate buffer (pH 7.5) was used for elution. The corresponding fractions were combined, concentrated and lyophilized 3 times to remove excess of buffer.

TABLE 1

Triphosphates obtained from Example 25

| Compound | $^{31}P$ NMR Pα | $^{31}P$ NMR Pβ | $^{31}P$ NMR Pγ | MS (M-1) |
|---|---|---|---|---|
| 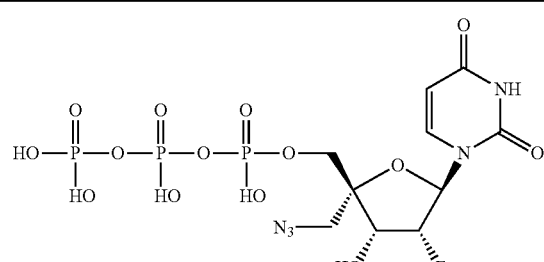<br>3A | −10.95(d) | −23.38(t) | −11.97(d) | 540.4 |
| 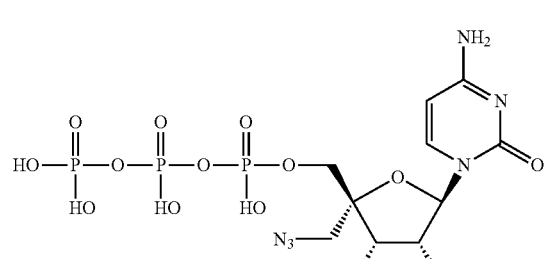<br>4A | −5.36(d) | −20.72(t) | −11.40(d) | 539.3 |
| 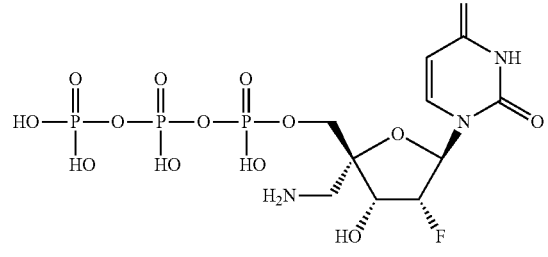<br>5A | −6.68<br>−6.81(d) | −22.25(t) | −11.79<br>−11.92(d) | 514.0 |

TABLE 1-continued

Triphosphates obtained from Example 25

| Compound | $^{31}$P NMR Pα | $^{31}$P NMR Pβ | $^{31}$P NMR Pγ | MS (M-1) |
|---|---|---|---|---|
| 6A | −5.95<br>−6.06(d) | −21.38(t) | −11.53<br>−11.65(d) | 513 |
| 9A | −10.31<br>−10.44(d) | −23.08(t) | −11.62<br>−11.84(d) | 579 |
| 10A | −9.94<br>−10.06(d) | −23.83(t) | −11.77<br>−11.89(d) | 553 |
| 11A | −10.79<br>−10.91(d) | −23.24(t) | −11.80<br>−11.92(d) | 563.0 |
| 12A | −6.48<br>−6.60(d) | −22.13(t) | −11.76<br>−11.88(d) | 537.0 |

Example 27

Additional Compounds

The foregoing syntheses are exemplary and can be used as a starting point to prepare a large number of additional compounds. Examples of compounds of Formula (I) that can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

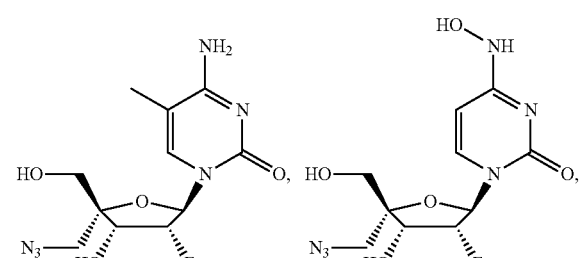

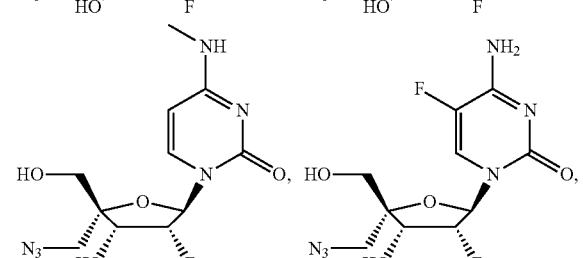

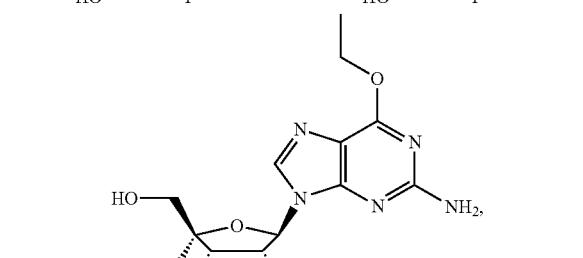

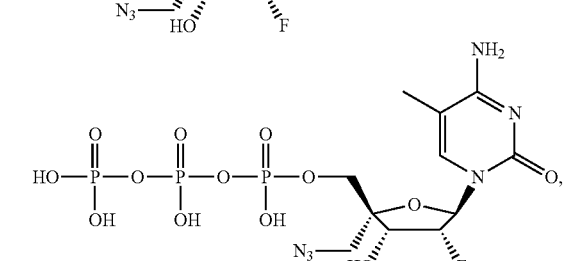

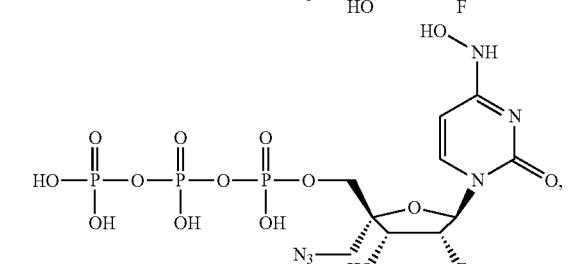

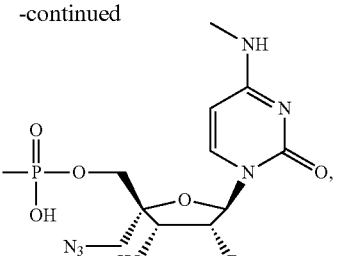

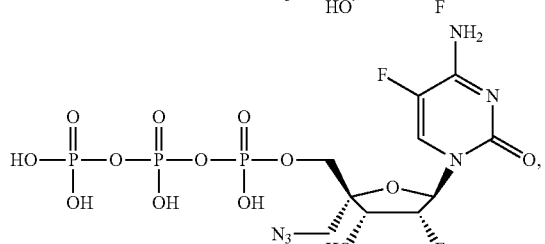

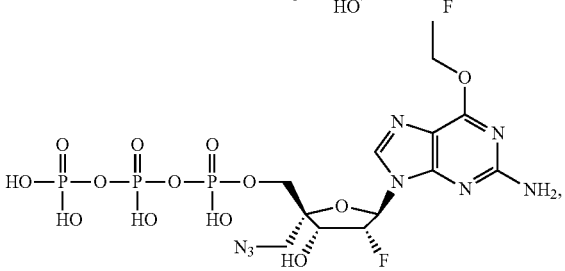

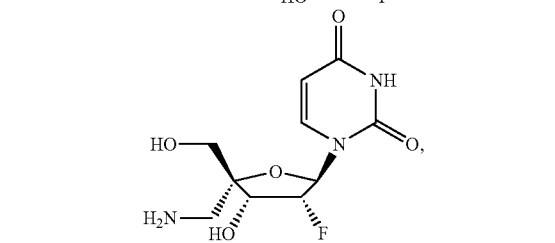

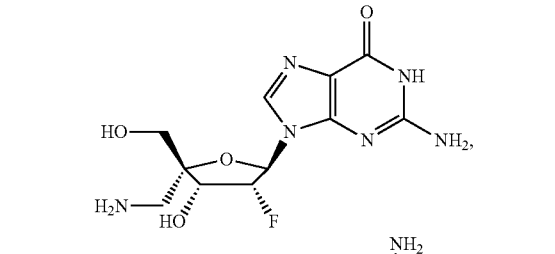

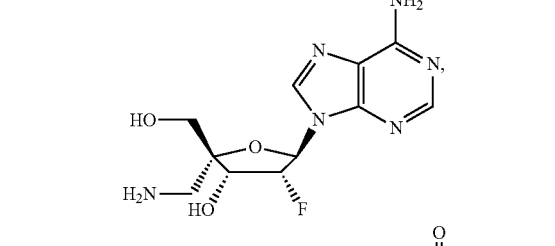

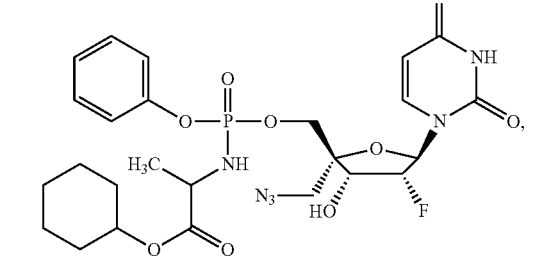

-continued

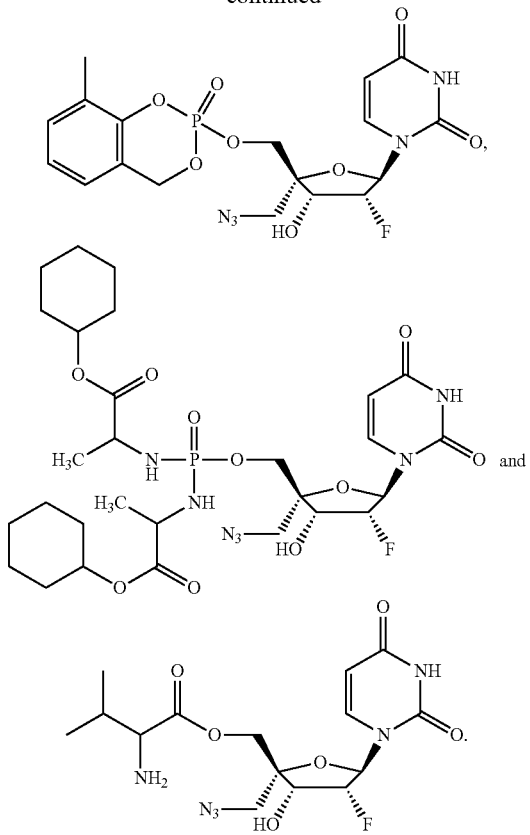

Example 28

RSV Assay

The RSV subgenomic replicon 395 HeLa was licensed from Apath (Brooklyn, N.Y.) and was originally developed by Dr. Mark Meeples of Center for Vaccines & Immunity, the Research Institute at Nationwide Children's Hospital in Columbus, Ohio. To generate subgenomic RSV replicon, three glycoprotein genes, those for SH, G, and F, from a full-length recombinant GFP-expressing (rg) RSV antigenomic cDNA were deleted. In their place, a blasticidin S deaminase (bsd) gene was inserted. Through multiple steps, the RSV replicon was established in HeLa cells. The 395 HeLa cells were cultured in Dulbecco's Modified Eagle Medium (DMEM) containing 4500 mg/L D-glucose, L-glutamine, and 110 mg/L sodium pyruvate (Invitrogen, Cat. #11995-040). The medium was further supplemented with 10% (v/v) fetal bovine serum (FBS) (Mediatech, Cat. #35-010-CV), 1% (v/v) penicillin/streptomycin (Mediatech, Cat. #30-002-CI), and 10 µg/mL of Blasticidin (BSD) (Invivogen, Cat. code ant-b1-1). Cells were maintained at 37° C. in a humidified 5% $CO_2$ atmosphere.

Determination of 50% inhibitory concentration ($EC_{50}$), 90% inhibitory concentration ($EC_{90}$) and 50% cytotoxic concentration ($CC_{50}$) in RSV replicon cells were performed by the following procedure. On the first day, 5000 RSV replicon cells per well were plated in a 96-well plate. On the following day, compounds to be tested were solubilized in 100% DMSO to 100× the desired final testing concentration. Each compound was serially diluted (1:3) up to 9 distinct concentrations. Compounds in 100% DMSO were reduced to 10% (v/v) DMSO by diluting 1:10 in cell culture media. A 10 µL sample of the compounds diluted to 10% (v/v) DMSO with cell culture media was used to treat the RSV replicon cells in 96-well format. The final DMSO concentration was 1% (v/v). Cells were incubated with compounds for 7 days at 37° C. in a 5% $CO_2$ atmosphere. In each assay, positive control that was previously characterized in the RSV replicon assay was included.

The *Renilla* Luciferase Assay System (Promega, Cat. #E2820) was used to measure anti-RSV replicon activity. Assay plates were set up as stated above. Luminescence was recorded using a Perkin Elmer multilabel counter Victor3V. $EC_{50}$, the concentration of the drug required for reducing RSV replicon RNA by 50% in relation to the untreated cell control value, was calculated from the plot of percentage reductions of the optical density (OD) value against the drug concentrations using the Microsoft Excel forecast function.

395 HeLa cell proliferation assay (Promega; CellTiter-Glo Luminescent Cell Viability Assay, Cat. #G7572) was used to measure cell viability. The CellTiter-Glo® Luminescent Cell Viability Assay is a homogeneous method to determine the number of viable cells in culture based on quantitation of the ATP present, which signals the presence of metabolically active cells. Assay plates were set up in the same format as noted above for the replicon assay. CellTiter-Glo reagent (100 µL) was added to each well and incubated at room temperature for 8 minutes. Luminescence was recorded using a Perkin Elmer multilabel counter Victor3V. The $CC_{50}$, the concentration of the drug required for reducing viable cells by 50% in relation to the untreated cell control value, was calculated from the plot of percentage reductions of the luminescence value against the drug concentrations using the Microsoft Excel forecast function.

Table A1 includes compounds with an $EC_{50}$ value that is less than 1 µM. Table A2 includes compounds with an $EC_{50}$ value that is equal to or higher than 1 µM and less than 50 µM. Other tested compounds disclosed herein had an $EC_{50}$ value of 50 µM or greater.

TABLE A1

| Compound |
| --- |
| 2A |
| 13A |
| 14A |
| 15A |
| 16A |

TABLE A2

| Compound |
| --- |
| 7A |
| 17A |
| 18A |
| 19A |
| 20A |
| 21A |
| 22A |
| 23A |
| 28A |

Standard RSV polymerase assays were conducted in the presence of 3 µL extract of RSV-infected cells in a reaction buffer containing 50 mM tris-acetate pH 8, 120 mM K-acetate, 4.5 mM $MgCl_2$, 5% glycerol, 2 mM EDTA, 50 ug/mL BSA, and 3 mM DTT. Varying concentration of test compounds were used to initiate RNA synthesis for 120 mins at 30° C., and radioactive 33P GTP (15 uCi) was used as tracer. The reaction was stopped by adding 50 mM EDTA, and RNA samples were purified through G-50 size exclusion spin columns and phenol-chloroform extraction. The radiolabeled RNA products were resolved by electrophoresis on a 6% polyacrylamide TBE gel, and visualized and quantitated after being exposed on a phosphorImager screen. Polymerase inhibition experiments ($IC_{50}$) were conducted the same way in the presence of increasing concentration of test compounds.

Table A3 includes compounds with an $IC_{50}$ value that is less than 1 µM against the polymerase. Table A4 includes compounds with an $IC_{50}$ value that is equal to or higher than 1 µM and less than 50 µM against the polymerase. Other tested compounds disclosed herein had an $IC_{50}$ value of 50 µM or greater against the polymerase.

TABLE A3

| Compound |
| --- |
| 3A |
| 4A |
| 11A |
| 12A |

TABLE A4

| Compound |
| --- |
| 5A |
| 6A |

Example 29

Parainfluenza Virus-3 (PIV-3) Plaque Assay

MA-104 cells were grown in 24-well plates to a confluency of 90% in the presence of minimal essential medium (MEM) supplemented with 10% fetal bovine serum and antibiotics (C-EMEM). The cells were then washed twice with non-complete minimal essential medium (NC-EMEM). Test articles were dissolved in DMSO to a stock concentration of 10 mM.

An aliquot of 0.5 mL of the test article at various concentrations was then inoculated in triplicate wells and incubated for 60 mins at 37° C. with 5% $CO_2$ for the diffusion of test article into MA-104 cells. After the incubation period, a stock of human PIV type 3 was thawed and diluted with NC-EMEM to achieve a viral concentration of $10^4$ pfu/mL. An aliquot of 0.1 mL was then inoculated into all the wells except for the negative and test article toxicity control wells. Upon infection, the plates were incubated for 72 h at 37° C. at 5% $CO_2$. After incubation, the plates were examined under microscopy to record cytotoxicity. The supernatants collected for viral quantification using a standard plaque assay using MA-104 cells as the indicator cells.

To perform the plaques assay, MA-104 cells were grown to confluence in 24-well plates. The cells were washed with serum-free medium prior to inoculation of duplicate wells with serial 10-fold dilutions of supernatant sample. After 1 h incubation at 37° C., the samples were aspirated and 1.0 mL of methyl cellulose overlay media was added to each well. After 6 days of culture, the cells were fixed and stained with 0.06% crystal violet in 1% glutaraldehyde and viral plaques enumerated. The data was analyzed with Prism software with $EC_{50}$ defined as drug concentration that reduced the viral load 50% from the viral control (VC). Table B1 provides a listing of compounds of Formula (I) that are active against PIV-3 with an $EC_{50}$<20 µM.

TABLE B1

| No. |
| --- |
| 2A |
| 14A |
| 15A |
| 16A |
| 17A |
| 18A |
| 19A |
| 28A |

Example 30

Human Metapneumovirus (hMPV) $TCID_{50}$ Assay

LLC-MK2 cells were grown in 24-well plates to a confluency of 90% in the presence of minimal essential medium (MEM) supplemented with 10% fetal bovine serum and antibiotics (C-EMEM). The cells were then washed twice with non-complete minimal essential medium (NC-EMEM). Test articles were dissolved in DMSO to a stock concentration of 10 mM.

An aliquot of 0.5 mL of the test article at various concentrations was then inoculated in triplicate wells and incubated for 60 mins at 37° C. with 5% $CO_2$ for the diffusion of test article into LLC-MK2 cells. After the incubation period, a stock of human metapneumovirus was thawed and diluted with NC-EMEM to achieve a viral concentration of $10^4$ pfu/mL. An aliquot of 0.1 mL was then inoculated into all the wells except for the negative and test article toxicity control wells. Upon infection, the plates were incubated for 7 days at 37° C. at 5% $CO_2$. After incubation, the plates were examined under microscopy to record cytotoxicity. The supernatants collected for viral quantification using a standard $TCID_{50}$ assay using LLC-MK2 cells as the indicator cells. The data was analyzed with Prism software with $EC_{50}$ defined as drug concentration that reduced the viral load 50% from the viral control (VC). Table C1 provides a listing of compounds of Formula (I) that are active against human metapneumovirus, with an $EC_{50}$<20 µM.

TABLE C1

| No. |
| --- |
| 2A |
| 7A |
| 8A |
| 13A |
| 14A |
| 15A |
| 16A |
| 17A |
| 18A |
| 19A |
| 28A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof,

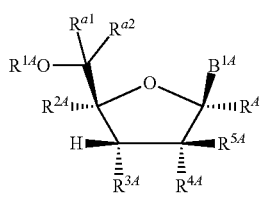
(I)

wherein:

$B^{1A}$ is an optionally substituted heterocyclic base or an optionally substituted heterocyclic base with a protected amino group;

$R^A$ is hydrogen or deuterium;

$R^{1A}$ is selected from the group consisting of hydrogen, an optionally substituted acyl, an optionally substituted O-linked amino acid,

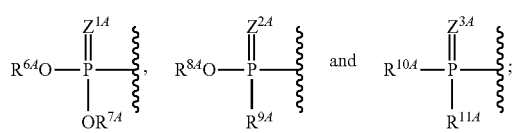

$R^{a1}$ and $R^{a2}$ are independently hydrogen or deuterium;

$R^{2A}$ is a $C_{1-6}$ azidoalkyl;

$R^{3A}$ is selected from the group consisting of OH, —OC(=O)$R^{iiiA}$ and an optionally substituted O-linked amino acid;

$R^{4A}$ is halogen;

$R^{5A}$ is hydrogen or halogen;

$R^{6A}$, $R^{7A}$ and $R^{8A}$ are independently selected from the group consisting of absent, hydrogen, an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—(CR$^{15A}$R$^{16A}$)$_p$—O—C$_{1-24}$ alkyl, an optionally substituted *—(CR$^{17A}$R$^{18A}$)$_q$—O—C$_{1-24}$ alkenyl,

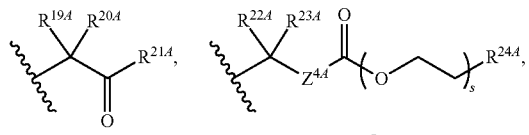

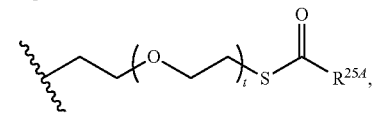

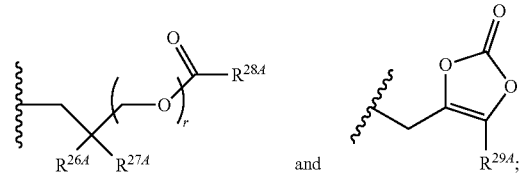

or $R^{6A}$ is

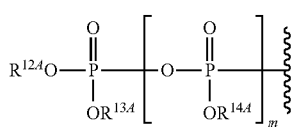

and $R^{7A}$ is absent or hydrogen; or $R^{6A}$ and $R^{7A}$ are taken together to form a moiety selected from the group consisting of an optionally substituted

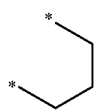

and an optionally substituted

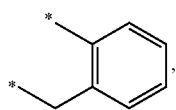, wherein the oxygens connected to $R^{6A}$ and $R^{7A}$, the phosphorus and the moiety form a six-membered to ten-membered ring system;

$R^{9A}$ is independently selected from the group consisting of an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{30A}R^{31A}$, an optionally substituted N-linked amino acid and an optionally substituted N-linked amino acid ester derivative;

$R^{10A}$ and $R^{11A}$ are independently an optionally substituted N-linked amino acid or an optionally substituted N-linked amino acid ester derivative;

$R^{12A}$, $R^{13A}$ and $R^{14A}$ are independently absent or hydrogen;

each $R^{15A}$, each $R^{16A}$, each $R^{17A}$ and each $R^{18A}$ are independently hydrogen, an optionally substituted $C_{1-24}$ alkyl or alkoxy;

$R^{19A}$, $R^{20A}$, $R^{22A}$ and $R^{23A}$ are independently selected from the group consisting of hydrogen, an optionally substituted $C_{1-24}$ alkyl and an optionally substituted aryl;

$R^{21A}$ and $R^{24A}$ are independently selected from the group consisting of hydrogen, an optionally substituted $C_{1-24}$ alkyl, an optionally substituted aryl, an optionally substituted —O—$C_{1-24}$ alkyl, an optionally substituted —O-aryl an optionally substituted —O-heteroaryl, an optionally substituted —O-monocyclic heterocyclyl and

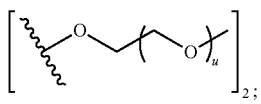

$R^{25A}$ and $R^{29A}$ are independently selected from the group consisting of hydrogen, an optionally substituted $C_{1-24}$ alkyl and an optionally substituted aryl;

$R^{26A}$ and $R^{27A}$ are independently —C≡N or an optionally substituted substituent selected from the group consisting of $C_{2-8}$ organylcarbonyl, $C_{2-8}$ alkoxycarbonyl and $C_{2-8}$ organylaminocarbonyl;

$R^{28A}$ is selected from the group consisting of hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl;

$R^{30A}$ and $R^{31A}$ are independently selected from the group consisting of hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl;

$R''^{A}$ is an optionally substituted $C_{1-24}$-alkyl;

m and t are independently 0 or 1;

p and q are independently selected from the group consisting of 1, 2 and 3;

r is 1 or 2;

s is 0, 1, 2 or 3;

u is 1 or 2; and $Z^{1A}$, $Z^{2A}$, $Z^{3A}$ and $Z^{4A}$ are independently O or S.

2. The compound of claim 1, wherein $R^{2A}$ is azidomethyl.

3. The compound of claim 1, wherein $R^{2A}$ is aminomethyl.

4. The compound of claim 1, wherein $R^{1A}$ is

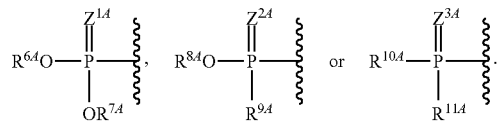

5. The compound of claim 4, wherein $R^{6A}$ and $R^{7A}$ are both hydrogen or absent.

6. The compound of claim 4, wherein both $R^{6A}$ and $R^{7A}$ are independently selected from the group consisting of an optionally substituted $C_{1-24}$ alkyl, an optionally substituted $C_{3-24}$ alkenyl, an optionally substituted $C_{3-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl),

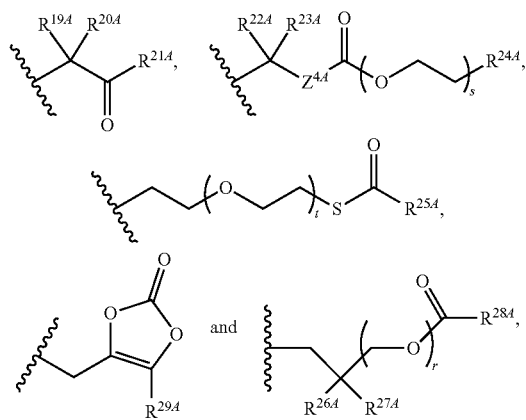

or $R^{6A}$ and $R^{7A}$ are taken to ether to form a moiety selected from the group consisting of an optionally substituted

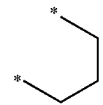

and an optionally substituted

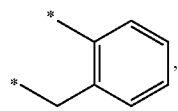

wherein the oxygens connected to $R^{6A}$ and $R^{7A}$, the phosphorus and the moiety form a six-membered to ten-membered ring system.

7. The compound of claim 4, wherein $R^{8A}$ is an optionally substituted aryl; and $R^{9A}$ is an optionally substituted N-linked amino acid or an optionally substituted N-linked amino acid ester derivative.

8. The compound of claim 4, wherein $R^{10A}$ and $R^{11A}$ are both an optionally substituted N-linked amino acid or an optionally substituted N-linked amino acid ester derivative.

9. The compound of claim 1, wherein $R^{1A}$ is

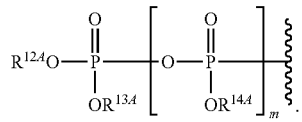

10. The compound of claim 9, wherein m is 0, and $R^{12A}$ and $R^{13A}$ are independently absent or hydrogen.

11. The compound of claim 9, wherein m is 1, and $R^{12A}$, $R^{13A}$ and $R^{14A}$ are independently absent or hydrogen.

12. The compound of claim 1, wherein $R^{1A}$ is H.

13. The compound of claim 1, wherein $R^{1A}$ is an optionally substituted acyl.

14. The compound of claim 1, wherein $R^{1A}$ is an optionally substituted O-linked amino acid.

15. The compound of claim 1, wherein $B^{1A}$ is selected from the group consisting of:

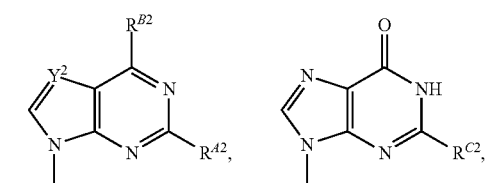

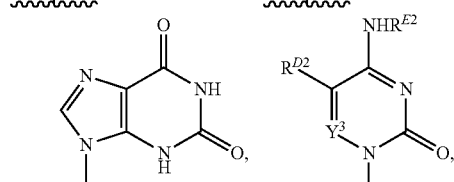

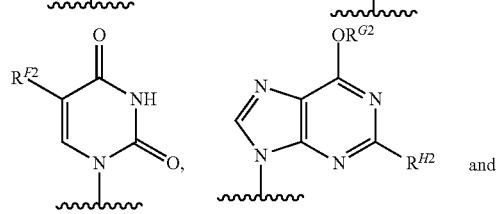

and

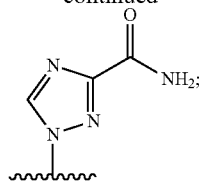

wherein:
$R^{A2}$ is selected from the group consisting of hydrogen, halogen and $NHR^{J2}$, wherein $R^{J2}$ is selected from the group consisting of hydrogen, —C(=O)$R^{K2}$ and —C(=O)O$R^{L2}$;

$R^{B2}$ is halogen or $NHR^{W2}$, wherein $R^{W2}$ is selected from the group consisting of hydrogen, an optionally substituted $C_{1-6}$ alkyl, an optionally substituted $C_{2-6}$ alkenyl, an optionally substituted $C_{3-8}$ cycloalkyl, —C(=O)$R^{M2}$ and —C(=O)O$R^{N2}$;

$R^{C2}$ is hydrogen or $NHR^{O2}$, wherein $R^{O2}$ is selected from the group consisting of hydrogen, —C(=O)$R^{P2}$ and —C(=O)O$R^{Q2}$;

$R^{D2}$ is selected from the group consisting of hydrogen, deuterium, halogen, an optionally substituted $C_{1-6}$ alkyl, an optionally substituted $C_{2-6}$ alkenyl and an optionally substituted $C_{2-6}$ alkynyl;

$R^{E2}$ is selected from the group consisting of hydrogen, hydroxy, an optionally substituted $C_{1-6}$ alkyl, an optionally substituted $C_{3-8}$ cycloalkyl, —C(=O)$R^{R2}$ and —C(=O)O$R^{S2}$;

$R^{F2}$ is selected from the group consisting of hydrogen, halogen, an optionally substituted $C_{1-6}$ alkyl, an optionally substituted $C_{2-6}$ alkenyl and an optionally substituted $C_{2-6}$ alkynyl;

$Y^2$ and $Y^3$ are independently N or $CR^{I2}$, wherein $R^{I2}$ is selected from the group consisting of hydrogen, halogen, an optionally substituted $C_{1-6}$-alkyl, an optionally substituted $C_{2-6}$-alkenyl and an optionally substituted $C_{2-6}$-alkynyl;

$R^{G2}$ is an optionally substituted $C_{1-6}$ alkyl;

$R^{H2}$ is hydrogen or $NHR^{T2}$, wherein $R^{T2}$ is independently selected from the group consisting of hydrogen, —C(=O)$R^{U2}$ and —C(=O)O$R^{V2}$; and $R^{K2}$, $R^{L2}$, $R^{M2}$, $R^{N2}$, $R^{P2}$, $R^{Q2}$ $R^{R2}$, $R^{S2}$, $R^{U2}$ and $R^{V2}$ are independently selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heterocyclyl, aryl($C_{1-6}$ alkyl), heteroaryl($C_{1-6}$ alkyl) and heterocyclyl ($C_{1-6}$ alkyl).

16. The compound of claim 15, wherein $B^{1A}$ is

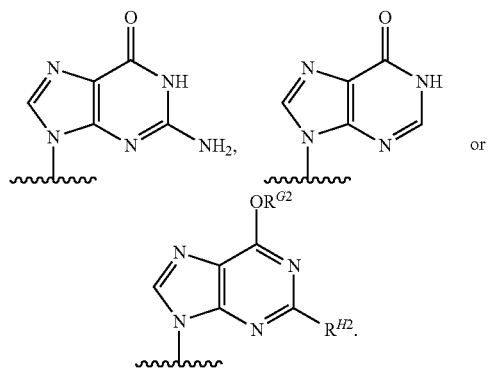

17. The compound of claim 15, wherein B^{1A} is

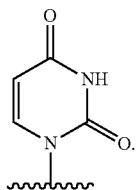

18. The compound of claim 15, wherein B^{1A} is

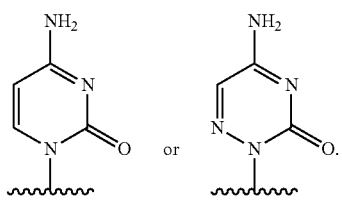 or

19. The compound of claim 1, wherein $R^{3A}$ is OH.
20. The compound of claim 1, wherein $R^{3A}$ is —OC(=O) $R''^A$.
21. The compound of claim 1, wherein $R^{3A}$ is O-linked amino acid.
22. The compound of claim 1, wherein $R^{5A}$ is hydrogen.
23. The compound of claim 1, wherein $R^{4A}$ is fluoro.
24. The compound of claim 1, wherein the compound of Formula (I) is:

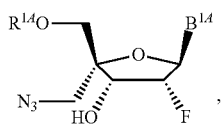

or a pharmaceutically acceptable salt thereof.

25. The compound of claim 1, wherein the compound of Formula (I) is:

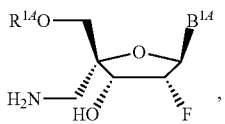

or a pharmaceutically acceptable salt thereof.

26. The compound of claim 1, wherein the compound of Formula (I) is selected from the group consisting of:

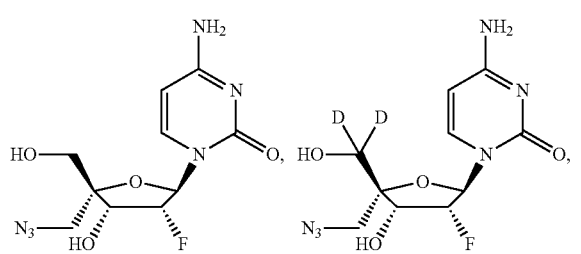

-continued

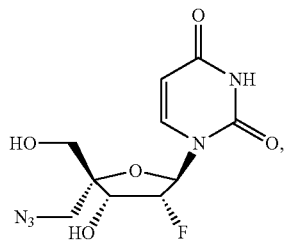

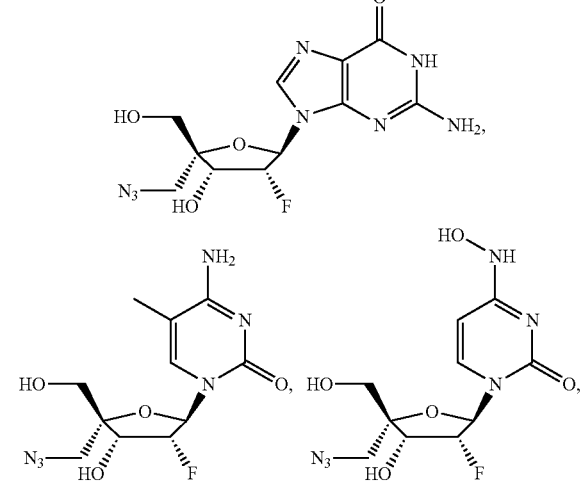

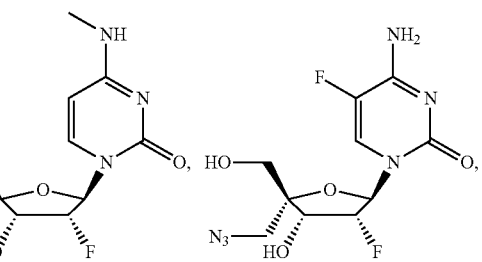

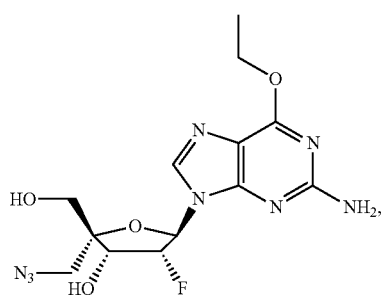

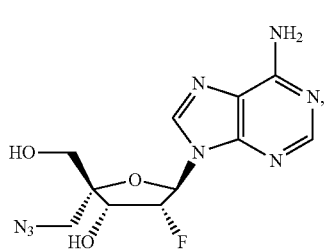

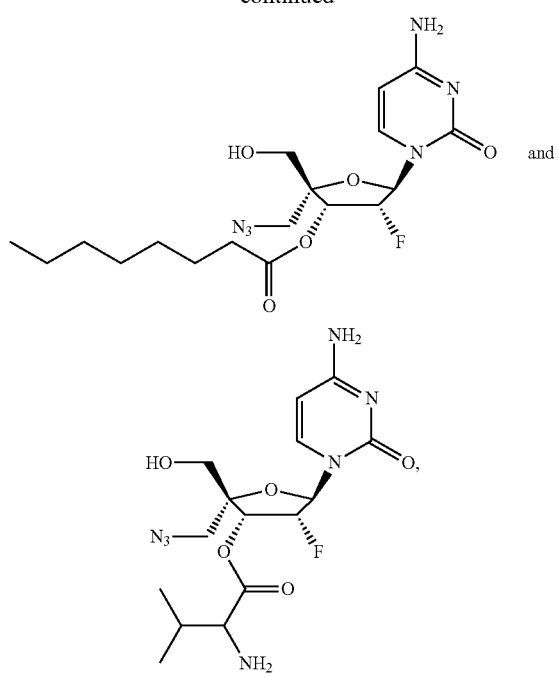
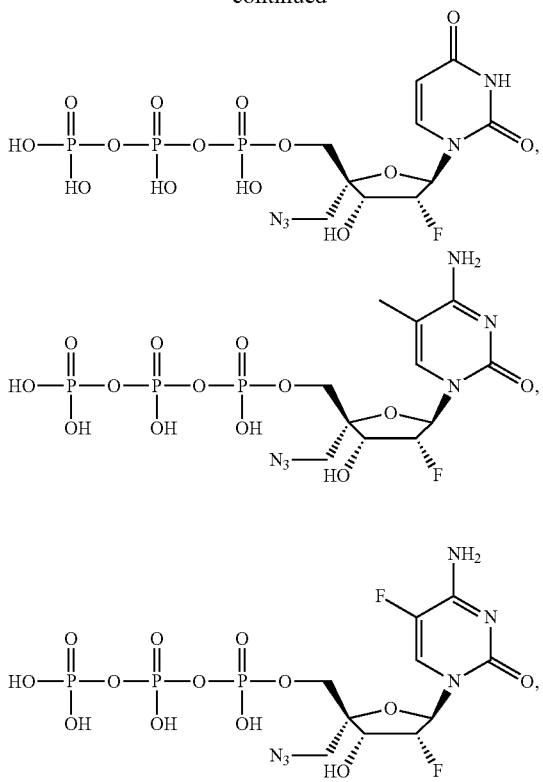
or a pharmaceutically acceptable salt of the foregoing.
27. The compound of claim 1, wherein the compound of Formula (I) is selected from the group consisting of:
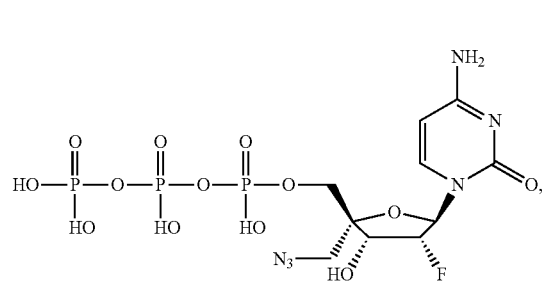
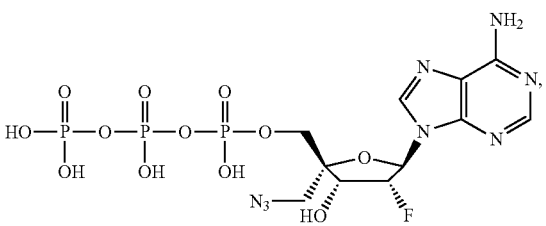
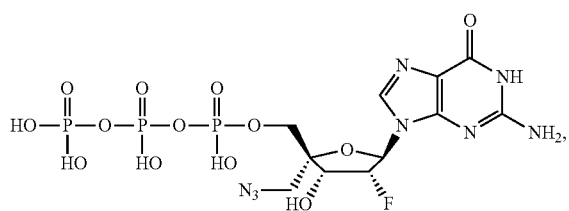
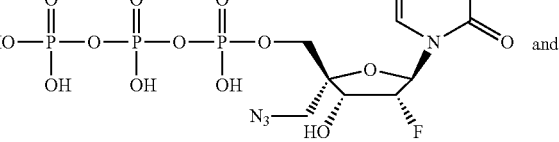
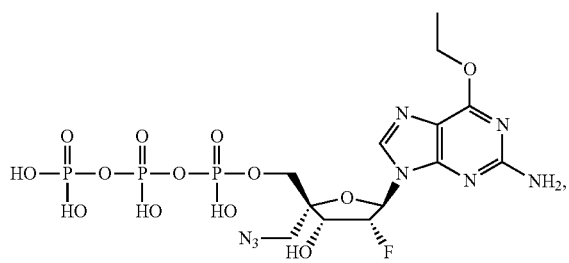
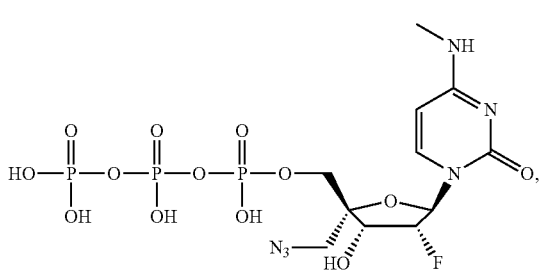
or a pharmaceutically acceptable salt of the foregoing.

28. The compound of claim 1, wherein the compound of Formula (I) is selected from the group consisting of:
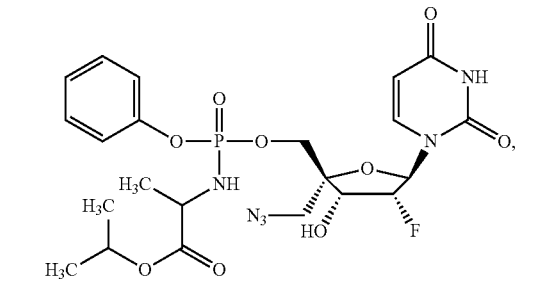
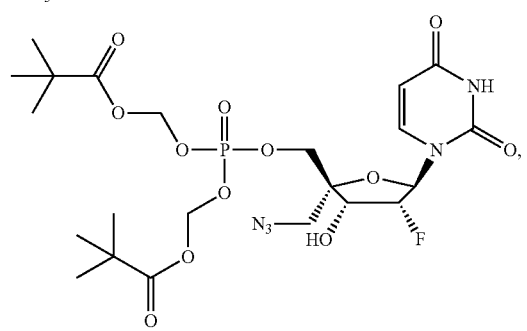
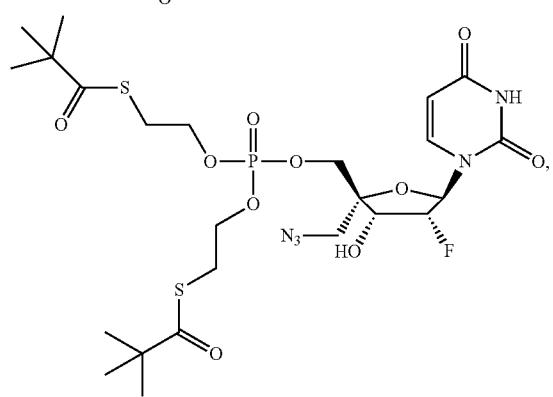
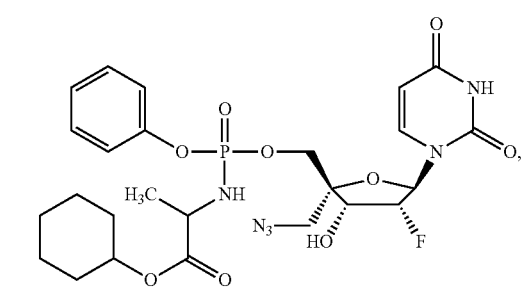
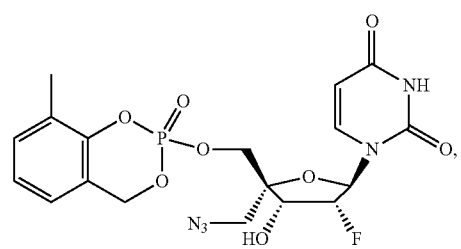
-continued
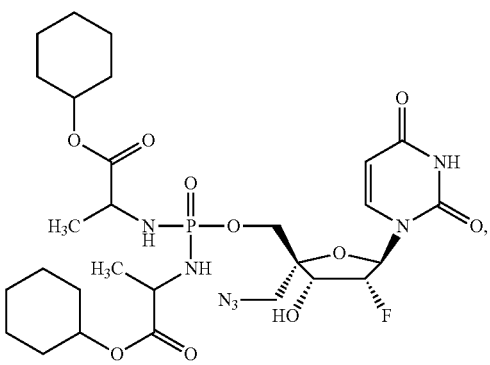
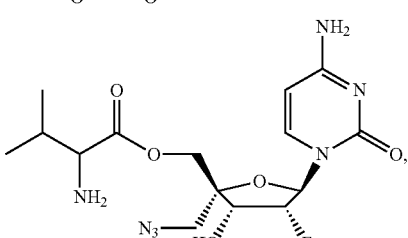
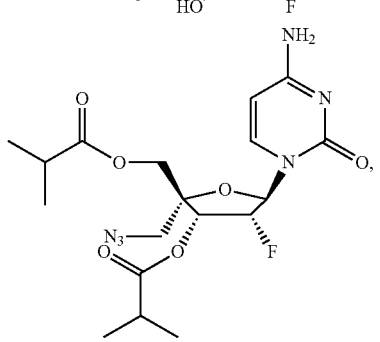
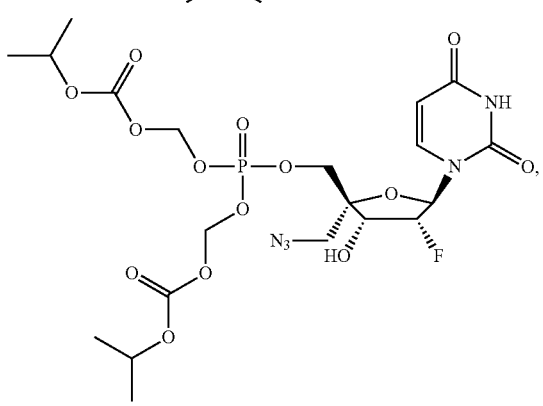
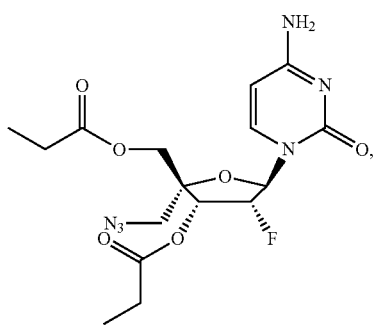

127
-continued
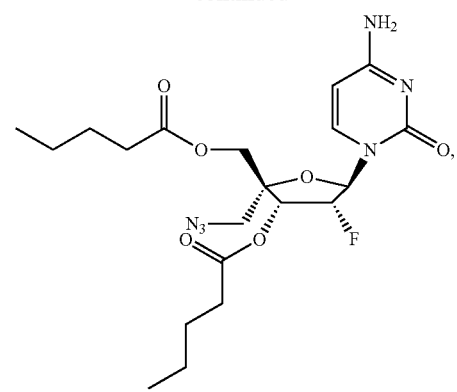
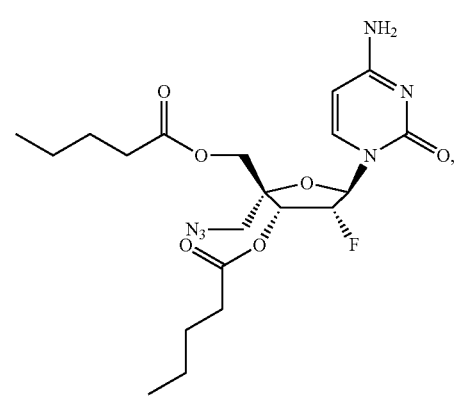
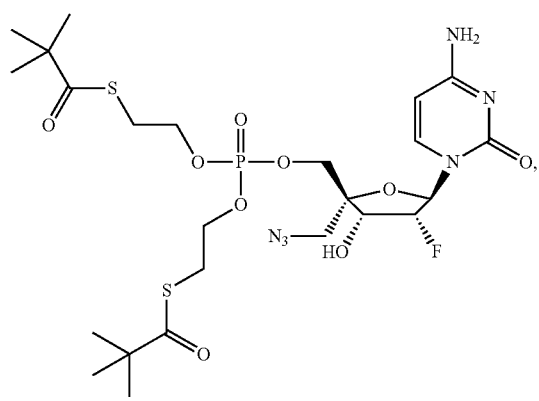
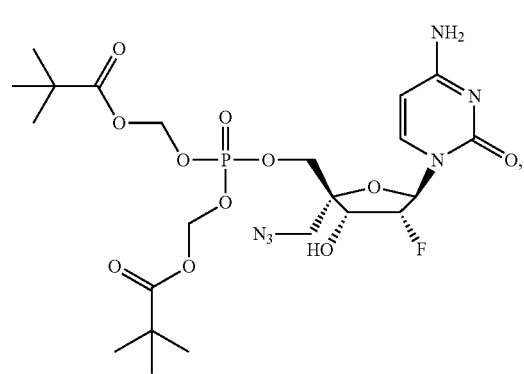
128
-continued
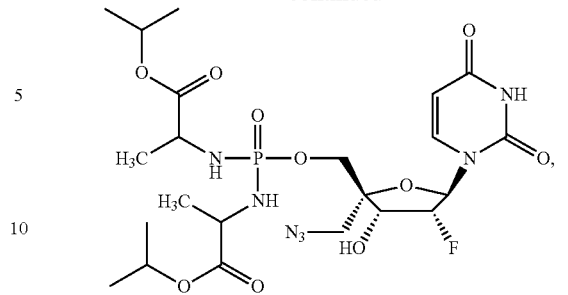
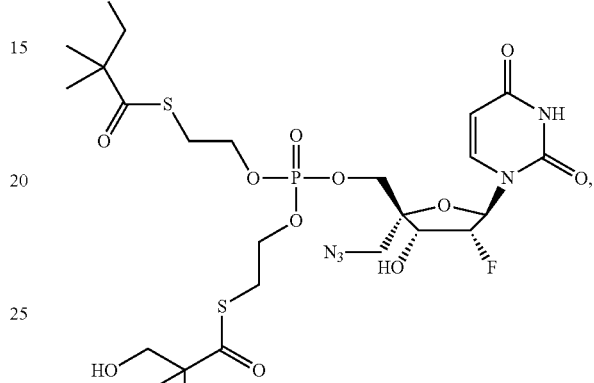
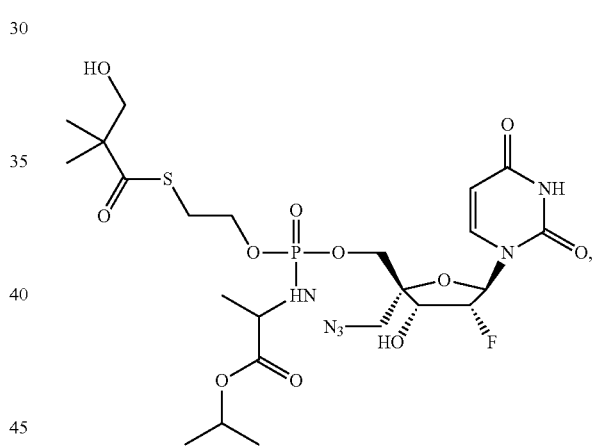
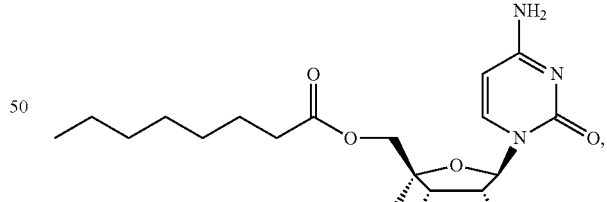
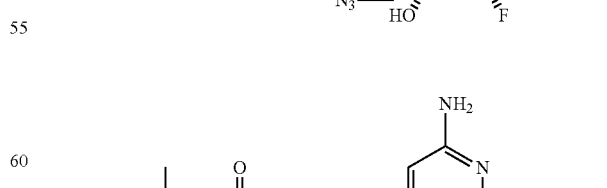
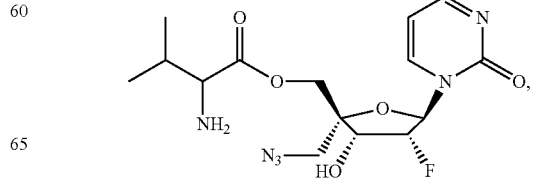

-continued

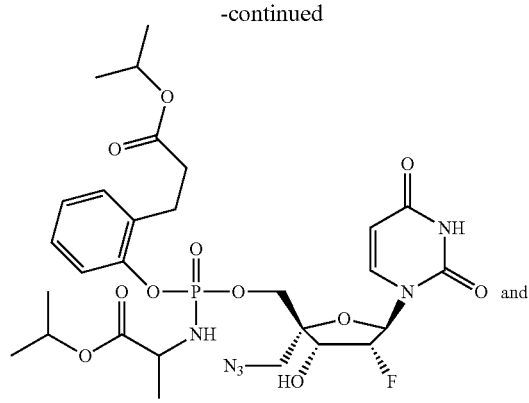

or a pharmaceutically acceptable salt of the foregoing.

29. A pharmaceutical composition comprising an effective amount of a compound of claim 1, or a pharmaceutically acceptable salt thereof, and a pharmaceutically acceptable carrier, diluent, excipient, or combination thereof.

30. A method for ameliorating or treating a paramyxovirus viral infection comprising administering to a subject identified as suffering from the paramyxovirus viral infection an effective amount of a compound of claim 1, or a pharmaceutically acceptable salt thereof.

31. A method for ameliorating or treating a paramyxovirus viral infection comprising contacting a cell infected with the paramyxovirus in a subject identified as suffering from the viral infection with an effective amount of a compound of claim 1, or a pharmaceutically acceptable salt thereof.

32. A method for ameliorating or treating a paramyxovirus viral infection in combination with one or more agents comprising administering to or contacting a cell in a subject identified as suffering from the paramyxovirus viral infection with an effective amount of a compound of claim 1, or a pharmaceutically acceptable salt thereof.

33. The method of claim 31, wherein the paramyxovirus viral infection is a human respiratory syncytial virus infection.

34. The method of claim 32, wherein the paramyxovirus viral infection is a human respiratory syncytial virus infection; and wherein the one or more agents is selected from the group consisting of ribavirin, palivizumab, RSV-IGIV, ALN-RSV01, BMS-433771, RFI-641, RSV604, MDT-637, BTA9881, TMC-353121, MBX-300, YM-53403, RV568 and a RSV-F Particle Vaccine.

35. The compound of claim 1, wherein the compound of Formula (I) is

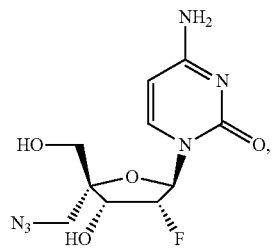

or a pharmaceutically acceptable salt thereof.

36. The compound of claim 1, wherein the compound of Formula (I) is

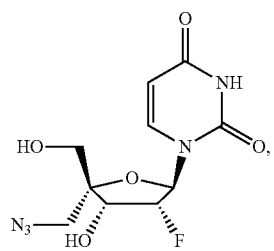

or a pharmaceutically acceptable salt thereof.

37. The compound of claim 1, wherein the compound of Formula (I) is

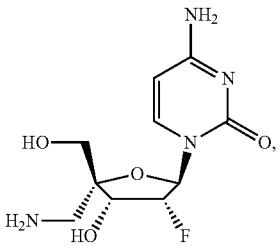

or a pharmaceutically acceptable salt thereof.

38. The compound of claim 1, wherein the compound of Formula (I) is

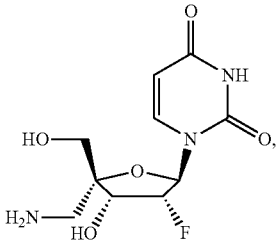

or a pharmaceutically acceptable salt thereof.

39. The compound of claim 1, wherein the compound of Formula (I) is

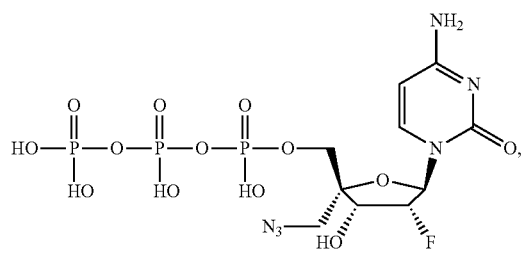

or a pharmaceutically acceptable salt thereof.

40. The compound of claim 1, wherein the compound of Formula (I) is

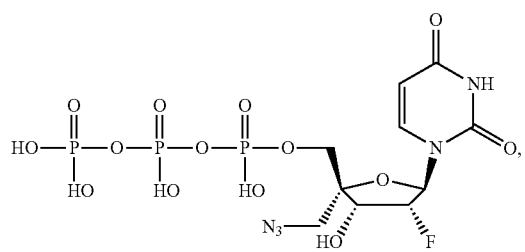

or a pharmaceutically acceptable salt thereof.

41. The compound of claim 1, wherein the compound of Formula (I) is

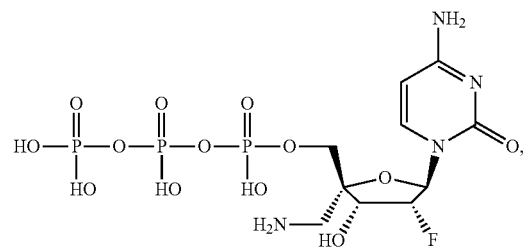

or a pharmaceutically acceptable salt thereof.

42. The compound of claim 1, wherein the compound of Formula (I) is

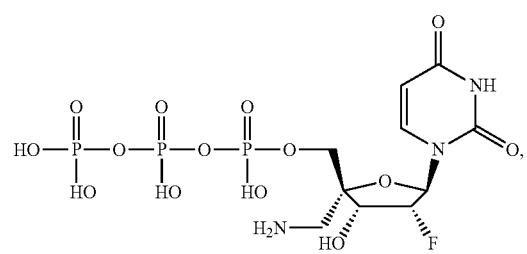

or a pharmaceutically acceptable salt thereof.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Combined DNA/RNA Molecule: Synthetic
      oligonucleotide

<400> SEQUENCE: 1
ggcucuuagc aaagucaagt t                                              21

<210> SEQ ID NO 2
<211> LENGTH: 21
<212> TYPE: DNA
<213> ORGANISM: Artificial Sequence
<220> FEATURE:
<223> OTHER INFORMATION: Combined DNA/RNA Molecule: Synthetic
      oligonucleotide

<400> SEQUENCE: 2
cuugacuuug cuaagagcct t                                              21